US010792038B2

(12) United States Patent
Becerra et al.

(10) Patent No.: US 10,792,038 B2
(45) Date of Patent: Oct. 6, 2020

(54) SURGICAL STAPLER WITH SELF-ADJUSTING STAPLE HEIGHT

(71) Applicant: Applied Medical Resources Corporation, Rancho Santa Margarita, CA (US)

(72) Inventors: Matthew M. Becerra, Lake Forest, CA (US); Steven E. Decker, Anaheim, CA (US); Timothy M. Hopkins, Rancho Santa Margarita, CA (US); Atal C. Patel, Mission Viejo, CA (US); Babak D. Jasemian, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 465 days.

(21) Appl. No.: 15/263,552

(22) Filed: Sep. 13, 2016

(65) Prior Publication Data

US 2016/0374678 A1  Dec. 29, 2016

Related U.S. Application Data

(63) Continuation of application No. PCT/US2015/050103, filed on Sep. 15, 2015.
(Continued)

(51) Int. Cl.
*A61B 17/072* (2006.01)
*A61B 90/00* (2016.01)
(Continued)

(52) U.S. Cl.
CPC .......... *A61B 17/07207* (2013.01); *A61B 2017/00407* (2013.01); *A61B 2017/0725* (2013.01);
(Continued)

(58) Field of Classification Search
CPC .... A61B 17/07207; A61B 2017/07207; A61B 2017/00407; A61B 2017/0725;
(Continued)

(56) References Cited

U.S. PATENT DOCUMENTS 2,073,960 A   3/1937   Crosby
2,140,593 A  12/1938   Pankonin
(Continued)

FOREIGN PATENT DOCUMENTS

EP   0 251 444 A1   1/1988
EP   0 492 283 A1   7/1992
(Continued)

OTHER PUBLICATIONS

The International Bureau of WIPO, International Preliminary Report on Patentability for International Application No. PCT/US2015/050103, titled "Surgical Stapler With Self-Adjusting Staple Height," dated Mar. 30, 2017, 12 pgs.
(Continued)

*Primary Examiner* — Dariush Seif
(74) *Attorney, Agent, or Firm* — John F. Heal

(57) ABSTRACT

A surgical stapler is provided that includes a spring loaded lift that automatically adjusts a staple cartridge and/or staple formation between a range of sizes. The lift is automatically released as the staple firing mechanism begins its forward translation of the firing sequence. The automatic one-way adjustment also adjusts the staple cartridge while maintaining the cartridge parallel to the anvil to provide consistent staple formations.

21 Claims, 79 Drawing Sheets

Related U.S. Application Data

(60) Provisional application No. 62/050,513, filed on Sep. 15, 2014.

(51) Int. Cl.
*A61B 17/29* (2006.01)
*A61B 17/00* (2006.01)

(52) U.S. Cl.
CPC .............. *A61B 2017/07271* (2013.01); *A61B 2017/07278* (2013.01); *A61B 2017/2923* (2013.01); *A61B 2090/0814* (2016.02)

(58) Field of Classification Search
CPC .......... A61B 2017/07271; A61B 2017/07278; A61B 2017/2923; A61B 17/0644; A61B 17/0682; A61B 17/07292; A61B 17/115; A61B 17/1155
USPC .............. 227/175.1–182.1; 606/75, 219, 220
See application file for complete search history.

(56) References Cited

U.S. PATENT DOCUMENTS

| | | | |
|---|---|---|---|
| 2,351,608 A | 6/1944 | Greenwood | |
| 2,487,565 A | 11/1949 | Leber et al. | |
| 2,641,154 A | 6/1953 | Heller | |
| 3,076,373 A | 2/1963 | Matthews | |
| 3,077,812 A | 2/1963 | Dietrich | |
| 3,080,564 A | 3/1963 | Strekopitov et al. | |
| 3,203,220 A | 8/1965 | Kaepernik | |
| 3,252,643 A | 5/1966 | Strekopitov et al. | |
| 3,273,562 A | 9/1966 | Brown | |
| 3,373,646 A | 3/1968 | Ehlert | |
| 3,459,187 A | 8/1969 | Pallotta | |
| 3,494,533 A | 2/1970 | Green et al. | |
| 3,662,939 A | 5/1972 | Bryan | |
| 3,675,688 A | 7/1972 | Bryan et al. | |
| 3,692,224 A | 9/1972 | Astafiev et al. | |
| 4,261,244 A | 4/1981 | Becht et al. | |
| 4,281,785 A | 8/1981 | Brooks | |
| 4,304,236 A | 12/1981 | Conta et al. | |
| 4,312,363 A | 1/1982 | Rothfuss et al. | |
| 4,317,451 A | 3/1982 | Cerwin et al. | |
| 4,407,286 A | 10/1983 | Noiles et al. | |
| 4,434,796 A | 3/1984 | Karapetian et al. | |
| 4,442,964 A | 4/1984 | Becht | |
| 4,454,875 A | 6/1984 | Pratt et al. | |
| 4,522,327 A | 6/1985 | Korthoff et al. | |
| 4,527,724 A | 7/1985 | Chow et al. | |
| 4,589,582 A | 5/1986 | Bilotti | |
| 4,591,085 A | 5/1986 | Di Giovanni | |
| 4,605,001 A | 8/1986 | Rothfuss et al. | |
| 4,606,344 A | 8/1986 | Di Giovanni | |
| 4,608,981 A | 9/1986 | Rothfuss et al. | |
| 4,610,383 A | 9/1986 | Rothfuss et al. | |
| 4,728,020 A | 3/1988 | Green et al. | |
| 4,805,823 A | 2/1989 | Rothfuss | |
| 4,892,244 A | 1/1990 | Fox et al. | |
| 4,923,350 A | 5/1990 | Hinksman et al. | |
| 4,941,623 A | 7/1990 | Pruitt | |
| 4,955,959 A | 9/1990 | Tompkins et al. | |
| 4,978,049 A | 12/1990 | Green | |
| 5,031,814 A | 7/1991 | Tompkins et al. | |
| 5,065,929 A | 11/1991 | Schulze et al. | |
| 5,071,052 A | 12/1991 | Rodak et al. | |
| 5,106,008 A | 4/1992 | Tompkins et al. | |
| 5,116,349 A | 5/1992 | Aranyi | |
| 5,129,570 A | 7/1992 | Schulze et al. | |
| 5,201,746 A | 4/1993 | Shichman | |
| 5,219,111 A * | 6/1993 | Bilotti ................. | A61B 17/072 227/175.1 |
| 5,221,036 A | 6/1993 | Takase | |
| 5,236,440 A | 8/1993 | Hlavacek | |
| 5,240,163 A | 8/1993 | Stein et al. | |
| RE34,519 E | 1/1994 | Fox et al. | |
| 5,275,323 A | 1/1994 | Schulze et al. | |
| 5,289,963 A | 3/1994 | McGarry et al. | |
| D347,474 S | 5/1994 | Olson | |
| 5,307,976 A | 5/1994 | Olson et al. | |
| 5,308,576 A | 5/1994 | Green et al. | |
| 5,326,013 A | 7/1994 | Green et al. | |
| 5,336,232 A * | 8/1994 | Green .................... | A61B 17/29 227/181.1 |
| 5,350,400 A | 9/1994 | Esposito et al. | |
| 5,360,305 A | 11/1994 | Kerrigan | |
| 5,364,002 A | 11/1994 | Green et al. | |
| 5,366,479 A | 11/1994 | McGarry et al. | |
| 5,381,943 A | 1/1995 | Allen et al. | |
| 5,389,098 A | 2/1995 | Tsuruta et al. | |
| 5,395,034 A | 3/1995 | Allen et al. | |
| 5,397,046 A | 3/1995 | Savage et al. | |
| 5,413,267 A | 5/1995 | Solyntjes et al. | |
| 5,415,334 A | 5/1995 | Williamson, IV et al. | |
| 5,415,335 A | 5/1995 | Knodell, Jr. | |
| 5,439,155 A | 8/1995 | Viola | |
| 5,439,479 A | 8/1995 | Shichman et al. | |
| 5,445,304 A | 8/1995 | Plyley et al. | |
| 5,447,265 A | 9/1995 | Vidal et al. | |
| 5,452,836 A | 9/1995 | Huitema et al. | |
| 5,456,401 A | 10/1995 | Green et al. | |
| 5,458,279 A | 10/1995 | Plyley | |
| 5,462,215 A | 10/1995 | Viola et al. | |
| 5,464,144 A | 11/1995 | Guy et al. | |
| 5,465,895 A | 11/1995 | Knodel et al. | |
| 5,470,006 A | 11/1995 | Rodak | |
| 5,470,007 A | 11/1995 | Plyley et al. | |
| 5,470,008 A | 11/1995 | Rodak | |
| 5,470,009 A | 11/1995 | Rodak | |
| 5,472,132 A | 12/1995 | Savage et al. | |
| 5,480,089 A | 1/1996 | Blewett | |
| 5,485,952 A | 1/1996 | Fontayne | |
| 5,487,500 A | 1/1996 | Knodel et al. | |
| 5,489,058 A | 2/1996 | Plyley | |
| 5,497,933 A | 3/1996 | DeFonzo et al. | |
| 5,507,426 A | 4/1996 | Young et al. | |
| 5,507,773 A | 4/1996 | Huitema et al. | |
| 5,509,596 A | 4/1996 | Green et al. | |
| 5,509,920 A | 4/1996 | Phillips et al. | |
| 5,529,235 A | 6/1996 | Boiarski et al. | |
| 5,533,521 A * | 7/1996 | Granger ................. | A61B 90/06 600/587 |
| 5,547,117 A | 8/1996 | Hamblin et al. | |
| 5,553,765 A | 9/1996 | Knodel et al. | |
| 5,554,164 A | 9/1996 | Wilson et al. | |
| 5,558,266 A | 9/1996 | Green et al. | |
| 5,562,241 A | 10/1996 | Knodel et al. | |
| 5,562,700 A | 10/1996 | Huitema et al. | |
| 5,562,701 A | 10/1996 | Huitema et al. | |
| 5,562,702 A | 10/1996 | Huitema et al. | |
| 5,564,615 A | 10/1996 | Bishop et al. | |
| 5,571,285 A | 11/1996 | Chow et al. | |
| 5,579,978 A | 12/1996 | Green et al. | |
| 5,580,067 A | 12/1996 | Hamblin et al. | |
| 5,584,425 A | 12/1996 | Savage et al. | |
| 5,586,711 A | 12/1996 | Plyley et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,605,272 A | 2/1997 | Witt et al. | |
| 5,607,095 A | 3/1997 | Smith et al. | |
| 5,615,820 A | 4/1997 | Viola | |
| 5,626,587 A | 5/1997 | Bishop et al. | |
| 5,630,539 A | 5/1997 | Plyley et al. | |
| 5,634,584 A | 6/1997 | Okorocha et al. | |
| 5,636,779 A | 6/1997 | Palmer | |
| 5,657,921 A | 8/1997 | Young et al. | |
| 5,662,258 A | 9/1997 | Knodel et al. | |
| 5,662,662 A | 9/1997 | Bishop et al. | |
| 5,662,667 A | 9/1997 | Knodel | |
| 5,673,840 A | 10/1997 | Schulze et al. | |
| 5,673,841 A | 10/1997 | Schulze et al. | |
| 5,673,842 A | 10/1997 | Bittner et al. | |
| 5,676,674 A | 10/1997 | Bolanos et al. | |

(56) References Cited

U.S. PATENT DOCUMENTS

| | | | |
|---|---|---|---|
| 5,678,748 A | 10/1997 | Plyley | |
| 5,680,982 A | 10/1997 | Schulze et al. | |
| 5,680,983 A | 10/1997 | Plyley et al. | |
| 5,697,542 A | 12/1997 | Knodel et al. | |
| 5,697,543 A | 12/1997 | Burdorff | |
| 5,704,534 A | 1/1998 | Huitema et al. | |
| 5,704,898 A | 1/1998 | Kokish | |
| 5,706,998 A | 1/1998 | Blyley et al. | |
| 5,709,334 A | 1/1998 | Sorrentino et al. | |
| 5,713,505 A | 2/1998 | Huitema | |
| 5,715,988 A | 2/1998 | Palmer | |
| 5,718,359 A | 2/1998 | Palmer et al. | |
| 5,732,871 A | 3/1998 | Clark et al. | |
| 5,735,445 A | 4/1998 | Vidal et al. | |
| 5,762,255 A | 6/1998 | Chrisman et al. | |
| 5,762,256 A | 6/1998 | Mastri et al. | |
| 5,779,130 A | 7/1998 | Alesi et al. | |
| 5,782,396 A | 7/1998 | Mastri et al. | |
| 5,782,397 A | 7/1998 | Koukline | |
| 5,785,232 A | 7/1998 | Vidal et al. | |
| 5,794,834 A | 8/1998 | Hamblin et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,810,240 A | 9/1998 | Robertson | |
| 5,814,055 A | 9/1998 | Knodel et al. | |
| 5,820,009 A | 10/1998 | Melling et al. | |
| 5,829,662 A | 11/1998 | Allen et al. | |
| 5,860,995 A | 1/1999 | Berkelaar | |
| 5,865,361 A | 2/1999 | Milliman et al. | |
| 5,878,937 A | 3/1999 | Green et al. | |
| 5,878,938 A | 3/1999 | Bittner et al. | |
| 5,893,506 A | 4/1999 | Powell | |
| 5,894,979 A | 4/1999 | Powell | |
| 5,901,895 A | 5/1999 | Heaton et al. | |
| 5,918,791 A | 7/1999 | Sorrentino et al. | |
| 5,931,847 A | 8/1999 | Bittner et al. | |
| 5,954,259 A | 9/1999 | Viola et al. | |
| 5,964,394 A | 10/1999 | Robertson | |
| D416,089 S | 11/1999 | Barton et al. | |
| 5,988,479 A | 11/1999 | Palmer | |
| 6,032,849 A | 3/2000 | Mastri et al. | |
| 6,053,390 A | 4/2000 | Green et al. | |
| 6,079,606 A | 6/2000 | Milliman et al. | |
| 6,109,500 A | 8/2000 | Alli et al. | |
| 6,131,789 A | 10/2000 | Schulze et al. | |
| 6,155,473 A | 12/2000 | Tompkins et al. | |
| D441,865 S | 5/2001 | Racenet et al. | |
| 6,241,139 B1 | 6/2001 | Milliman et al. | |
| 6,250,532 B1 | 6/2001 | Green et al. | |
| 6,264,087 B1 | 7/2001 | Whitman | |
| 6,270,453 B1 | 8/2001 | Sakai | |
| 6,325,810 B1 | 12/2001 | Hamilton et al. | |
| 6,330,965 B1 | 12/2001 | Milliman et al. | |
| 6,488,196 B1 * | 12/2002 | Fenton, Jr. ............ | A61B 17/068 227/175.1 |
| 6,550,757 B2 | 4/2003 | Sesek | |
| 6,569,171 B2 | 5/2003 | DeGuillebon et al. | |
| 6,595,509 B2 | 7/2003 | Sesek | |
| 6,619,529 B2 | 9/2003 | Green et al. | |
| 6,644,532 B2 | 11/2003 | Green et al. | |
| 6,669,073 B2 | 12/2003 | Milliman et al. | |
| 6,716,233 B1 | 4/2004 | Whitman | |
| 6,786,382 B1 | 9/2004 | Hoffman | |
| 6,817,508 B1 | 11/2004 | Racenet et al. | |
| 6,821,282 B2 | 11/2004 | Perry et al. | |
| 6,835,199 B2 | 12/2004 | McGuckin, Jr. et al. | |
| 6,913,181 B2 | 7/2005 | Mochizuki et al. | |
| 6,923,360 B2 | 8/2005 | Sesek et al. | |
| 6,953,138 B1 | 10/2005 | Dworak et al. | |
| 6,953,139 B2 | 10/2005 | Milliman et al. | |
| 6,964,363 B2 | 11/2005 | Wales et al. | |
| 6,978,921 B2 | 12/2005 | Shelton, IV et al. | |
| 6,986,451 B1 | 1/2006 | Mastri et al. | |
| 6,988,649 B2 | 1/2006 | Shelton, IV et al. | |
| 7,000,818 B2 | 2/2006 | Shelton, IV et al. | |
| 7,044,352 B2 | 5/2006 | Shelton, IV et al. | |
| 7,044,353 B2 | 5/2006 | Mastri et al. | |
| 7,044,947 B2 | 5/2006 | de la Torre et al. | |
| 7,055,730 B2 | 6/2006 | Ehrenfels et al. | |
| 7,070,083 B2 | 7/2006 | Jankowski | |
| 7,097,089 B2 | 8/2006 | Marczyk | |
| 7,097,650 B2 | 8/2006 | Weller et al. | |
| 7,108,472 B2 | 9/2006 | Norris et al. | |
| 7,128,253 B2 | 10/2006 | Mastri et al. | |
| 7,140,527 B2 | 11/2006 | Ehrenfels et al. | |
| 7,140,528 B2 | 11/2006 | Shelton, IV | |
| 7,143,923 B2 | 12/2006 | Shelton, IV et al. | |
| 7,143,924 B2 | 12/2006 | Scirica et al. | |
| 7,147,139 B2 | 12/2006 | Schwemberger et al. | |
| 7,213,736 B2 | 5/2007 | Wales et al. | |
| 7,225,964 B2 | 6/2007 | Mastri et al. | |
| 7,237,708 B1 | 7/2007 | Guy et al. | |
| 7,258,262 B2 | 8/2007 | Mastri et al. | |
| 7,275,674 B2 | 10/2007 | Racenet et al. | |
| 7,278,562 B2 | 10/2007 | Mastri et al. | |
| 7,290,692 B2 | 11/2007 | Marks | |
| 7,293,685 B2 | 11/2007 | Ehrenfels et al. | |
| 7,303,107 B2 | 12/2007 | Milliman et al. | |
| 7,308,998 B2 | 12/2007 | Mastri et al. | |
| 7,328,828 B2 | 2/2008 | Ortiz et al. | |
| 7,334,717 B2 | 2/2008 | Rethy et al. | |
| 7,380,695 B2 | 6/2008 | Doll et al. | |
| 7,380,696 B2 | 6/2008 | Shelton, IV et al. | |
| 7,398,908 B2 | 7/2008 | Holsten et al. | |
| 7,399,310 B2 | 7/2008 | Edoga et al. | |
| 7,401,721 B2 | 7/2008 | Holsten et al. | |
| 7,404,508 B2 | 7/2008 | Smith et al. | |
| 7,407,075 B2 | 8/2008 | Holsten et al. | |
| 7,407,078 B2 | 8/2008 | Shelton, IV et al. | |
| 7,416,101 B2 | 8/2008 | Shelton, IV et al. | |
| RE40,514 E | 9/2008 | Mastri et al. | |
| 7,419,080 B2 | 9/2008 | Smith et al. | |
| 7,419,081 B2 | 9/2008 | Ehrenfels et al. | |
| 7,422,136 B1 | 9/2008 | Marczyk | |
| 7,422,139 B2 | 9/2008 | Shelton, IV et al. | |
| 7,431,188 B1 | 10/2008 | Marczyk | |
| 7,434,715 B2 | 10/2008 | Shelton, IV et al. | |
| 7,434,716 B2 | 10/2008 | Viola | |
| 7,455,208 B2 | 11/2008 | Wales et al. | |
| 7,455,676 B2 | 11/2008 | Holsten et al. | |
| 7,461,767 B2 | 12/2008 | Viola et al. | |
| 7,464,846 B2 | 12/2008 | Shelton, IV et al. | |
| 7,464,847 B2 | 12/2008 | Viola et al. | |
| 7,464,849 B2 | 12/2008 | Shelton, IV et al. | |
| 7,467,740 B2 * | 12/2008 | Shelton, IV ..... | A61B 17/07207 227/178.1 |
| 7,472,814 B2 | 1/2009 | Mastri et al. | |
| 7,472,815 B2 | 1/2009 | Shelton, IV et al. | |
| 7,472,816 B2 | 1/2009 | Holsten et al. | |
| 7,481,348 B2 | 1/2009 | Marczyk | |
| 7,481,349 B2 | 1/2009 | Holsten et al. | |
| 7,487,899 B2 | 2/2009 | Shelton, IV et al. | |
| 7,490,749 B2 | 2/2009 | Schall et al. | |
| 7,506,790 B2 | 3/2009 | Shelton, IV | |
| 7,506,791 B2 | 3/2009 | Omaits et al. | |
| 7,513,408 B2 | 4/2009 | Shelton, IV et al. | |
| 7,530,484 B1 | 5/2009 | Durrani | |
| 7,543,730 B1 | 6/2009 | Marczyk | |
| 7,543,731 B2 | 6/2009 | Green et al. | |
| 7,546,940 B2 | 6/2009 | Milliman et al. | |
| 7,549,564 B2 | 6/2009 | Boudreaux | |
| 7,552,854 B2 | 6/2009 | Wixey et al. | |
| 7,556,186 B2 | 7/2009 | Milliman | |
| 7,565,993 B2 | 7/2009 | Milliman et al. | |
| 7,568,604 B2 | 8/2009 | Ehrenfels et al. | |
| 7,588,174 B2 | 9/2009 | Holsten et al. | |
| 7,588,175 B2 | 9/2009 | Timm et al. | |
| 7,588,177 B2 | 9/2009 | Racenet | |
| 7,604,151 B2 | 10/2009 | Hess et al. | |
| 7,611,038 B2 | 11/2009 | Racenet et al. | |
| 7,617,961 B2 | 11/2009 | Viola | |
| 7,624,902 B2 | 12/2009 | Marczyk et al. | |
| 7,631,793 B2 | 12/2009 | Rethy et al. | |

(56) References Cited

U.S. PATENT DOCUMENTS

| | | |
|---|---|---|
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |

(56) References Cited

U.S. PATENT DOCUMENTS

| | | |
|---|---|---|
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,893,949 B2 * | 11/2014 | Shelton, IV ............ A61B 90/92 227/175.1 |
| 8,899,462 B2 | 12/2014 | Kostrzewski et al. |
| 8,899,463 B2 | 12/2014 | Schell et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 2002/0025243 A1 | 2/2002 | Heck |
| 2002/0029044 A1 | 3/2002 | Monassevitch et al. |

(56) References Cited

U.S. PATENT DOCUMENTS

| | | |
|---|---|---|
| 2002/0062136 A1 | 5/2002 | Hillstead et al. |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0234478 A1 | 10/2005 | Wixey et al. |
| 2006/0097026 A1 | 5/2006 | Shelton, IV |
| 2006/0180634 A1 | 8/2006 | Shelton, IV et al. |
| 2006/0289602 A1 | 12/2006 | Wales et al. |
| 2007/0034664 A1 | 2/2007 | Jiang |
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155787 A1 | 6/2011 | Laurent et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0168487 A1 | 7/2012 | Holsten et al. |
| 2012/0193396 A1 | 8/2012 | Zemlok et al. |
| 2012/0211542 A1 | 8/2012 | Racenet |
| 2012/0286022 A1 | 11/2012 | Olson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1* | 7/2013 | Hess .................... F16B 15/00 606/219 |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |

(56) References Cited

U.S. PATENT DOCUMENTS

| | | |
|---|---|---|
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0252064 A1* | 9/2014 | Mozdzierz ........... A61B 17/068 227/176.1 |
| 2014/0252068 A1* | 9/2014 | Shelton, IV ..... A61B 17/00234 227/178.1 |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0183948 A1 | 6/2016 | Shelton, IV et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0056008 A1* | 3/2017 | Shelton, IV ......... A61B 17/105 |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 005 902 A2 | 12/2008 |
| EP | 2 263 568 A2 | 12/2010 |
| EP | 2 361 562 A1 | 8/2011 |
| EP | 2 486 859 A2 | 8/2012 |
| EP | 2 772 192 A1 | 9/2014 |
| EP | 2 777 530 A1 | 9/2014 |
| EP | 2 923 661 A2 | 3/2015 |
| EP | 2 926 742 A1 | 10/2015 |
| EP | 3 238 639 A2 | 3/2017 |
| JP | 2001-087272 A | 4/2001 |
| RU | 2063710 | 7/1996 |
| WO | WO 83/02247 A1 | 7/1983 |
| WO | WO 02/30296 A2 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |
| WO | WO-2018019072 A1 * | 2/2018 ........... A61B 17/072 |

OTHER PUBLICATIONS

European Patent Office, European Search Report for European Application No. 07784007.2, entitled "Surgical Stapler," dated Jun. 15, 2012, 6 pgs.

Ethicon Endo Surgery, Inc., Contour Curved Cutter Stapler, 2014, 2 pgs.

Justright Surgical, JustRight Surgery, Dec. 31, 2014, 2 pgs.

European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.

European Patent Office, International Search Report and Written Opinion for International Application no. PCT/US2014/028211, entitled "Surgical Stapler with Partial Pockets," dated Sep. 8, 2014, 17 pgs.

International Searching Authority, U.S., The International Search Report and the Written Opinion of the International Searching

(56) References Cited

OTHER PUBLICATIONS authority for international application PCT/US2014/027768, titled "Surgical Stapler with Expandable Jaw", dated Jul. 25, 2014, 17 pgs.
The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.
International Searching Authority, U.S., The International Search Report and the Written Opinion of the International Searching authority for international application PCT/US2015/0035379, titled "Surgical Stapler with Circumferential Firing", dated Sep. 15, 2015, 22 pgs.
European Patent Office, International Search Report and Written Opinion for International Application No. PCT/US2015/050103 titled "Surgical Stapler with Self-Adjusting Staple Height" dated Feb. 17, 2016, 18 pgs.
The International Bureau of WIPO, International Preliminary Report on Patentability for International Application No. PCT/US2015/035379, entitled "Surgical Stapler with Circumferential Firing," dated Dec. 22, 2016, 14 pgs.
European Patent Office, European Search Report for European Application No. EP 14764812.5, entitled "Surgical Stapler Having Actuation Mechanism with Rotatable Shaft," dated Apr. 6, 2017, 6 pgs.
International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.
International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.
International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.
European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.
European Patent Office, The International Search Report and the Written Opinion of the International Searching Authority for International Application No. PCT/US2017/027213, entitled "Surgical Stapler Having a Powered Handle," dated Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.
European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.
European Patent Office, Partial European Search Report for European Application No. EP 14762896.0, entitled "Surgical Stapler with Expandable Jaw," dated Apr. 10, 2017, 6 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, Extended European Search Report for European Application No. EP 18186558.5, entitled "Surgical Stapler with Partial Pockets," dated Oct. 10, 2018, 9 pgs.
The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.
European Patent Office, Extended European Search Report for European Application No. EP 18189960.0, entitled "Surgical Stapler with Expandable Jaw," dated Dec. 13, 2018, 6 pgs.
International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.
European Patent Office, The International Search Report and the Written Opinion of the International Searching Authority for International Application No. PCT/US2019/019867, entitled "Surgical Stapler Having a Powered Handle," dated Jul. 19, 2019, 24 pgs.
European Patent Office, Extended European Search Report for European Application No. EP 19150575.9, entitled "Surgical Stapler Having Actuation Mechanism with Rotatable Shaft," dated Aug. 21, 2019, 5 pgs.

* cited by examiner

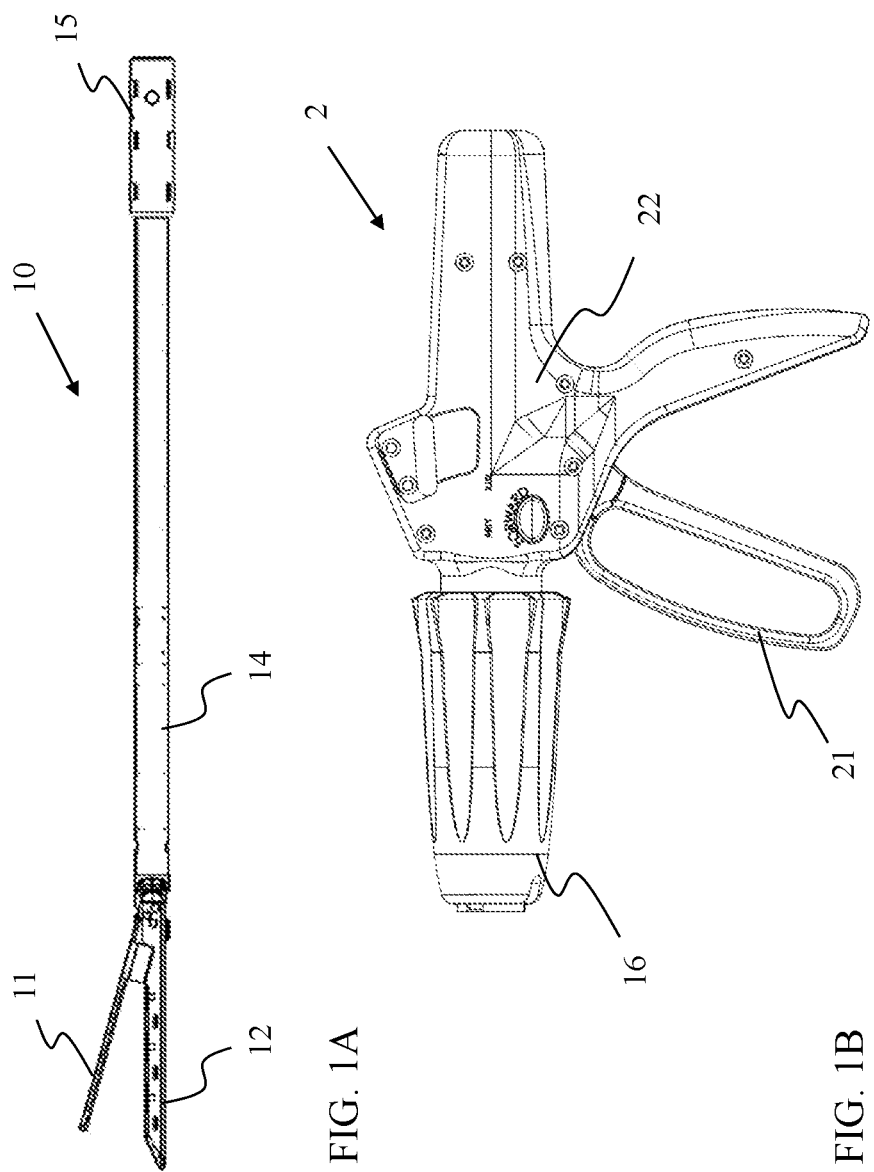

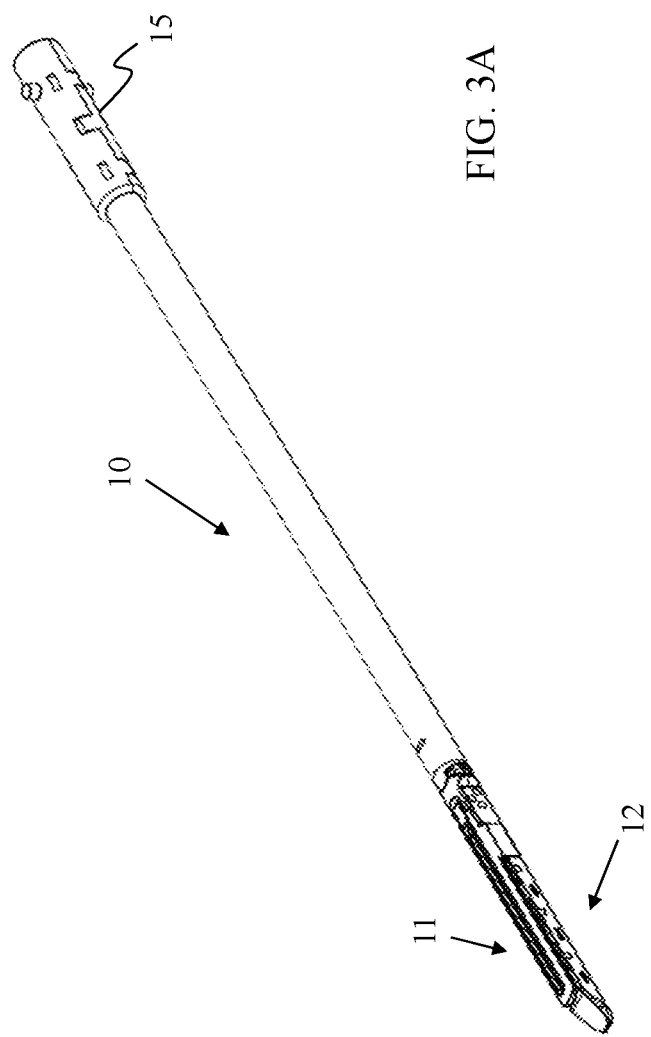
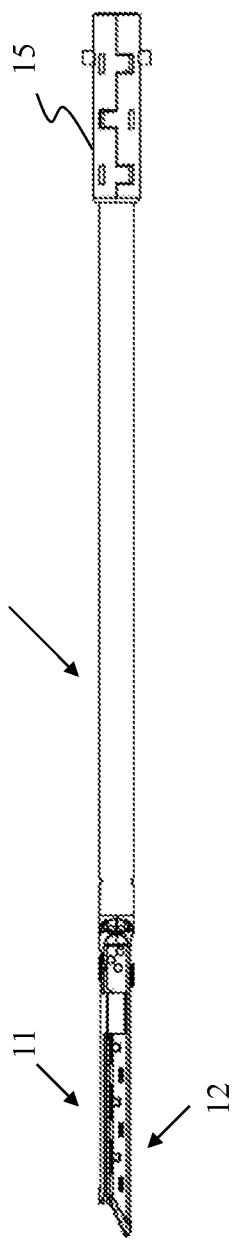
FIG. 3A
FIG. 3B

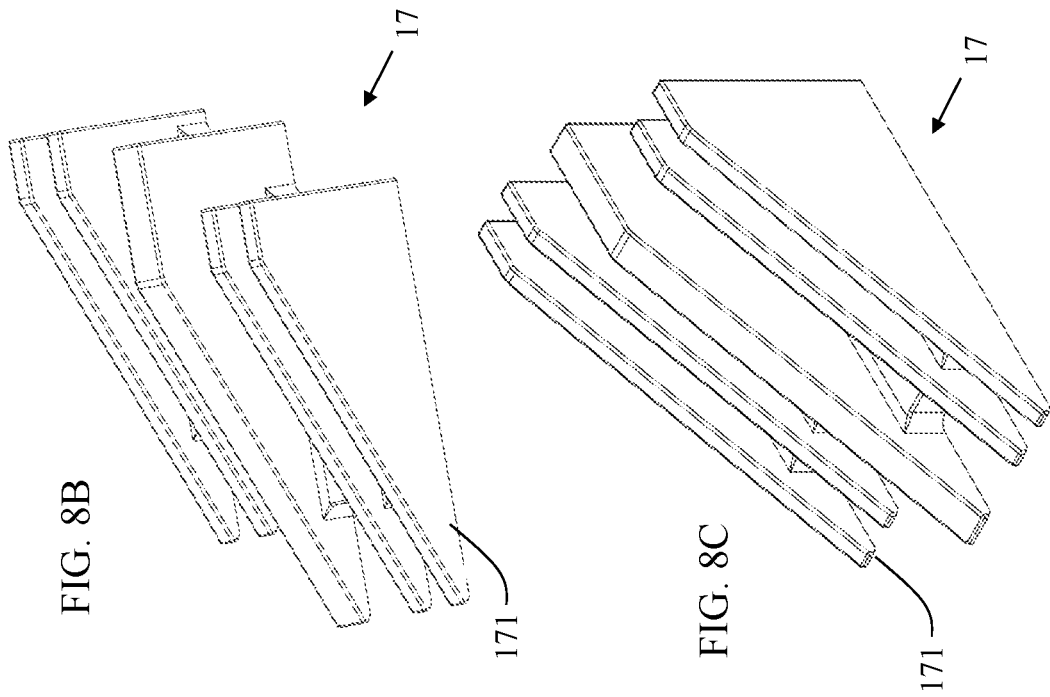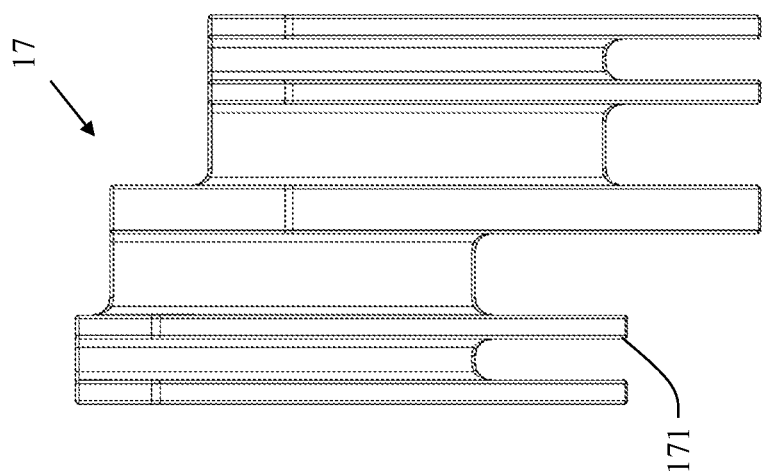

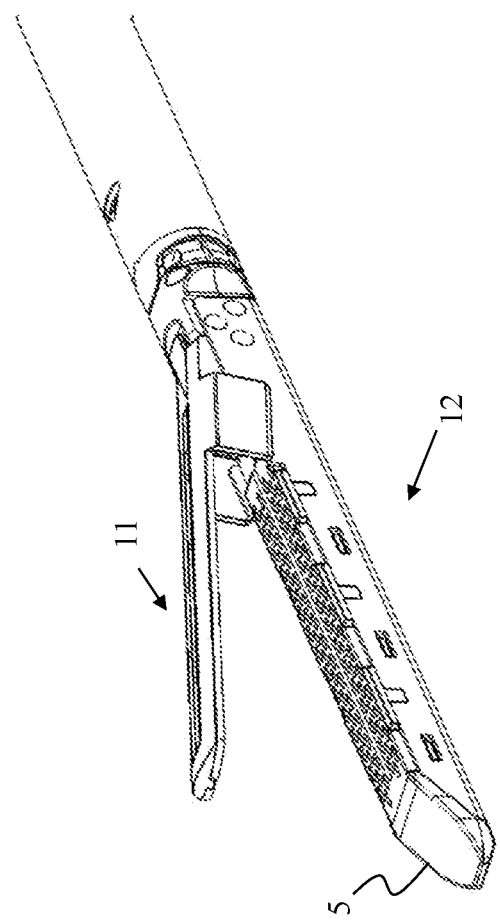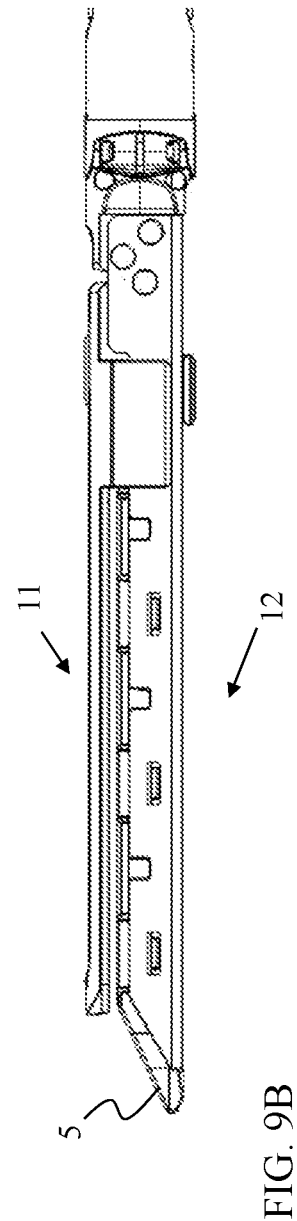
FIG. 9A
FIG. 9B

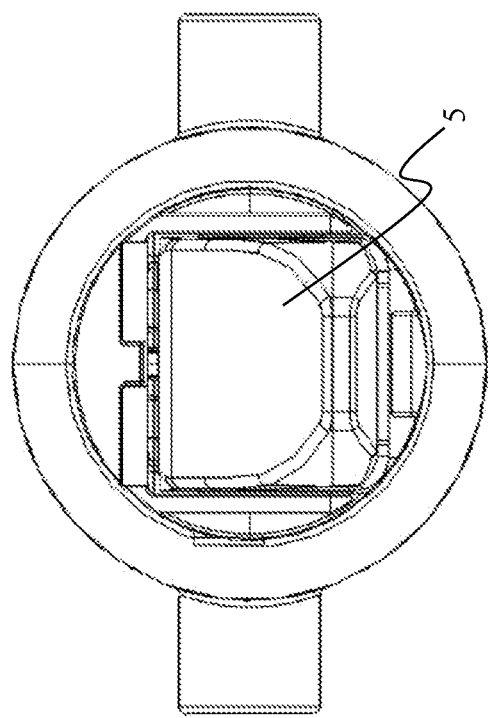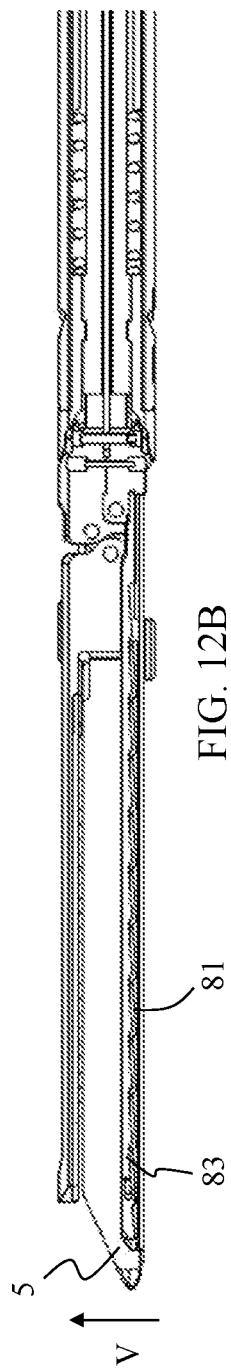

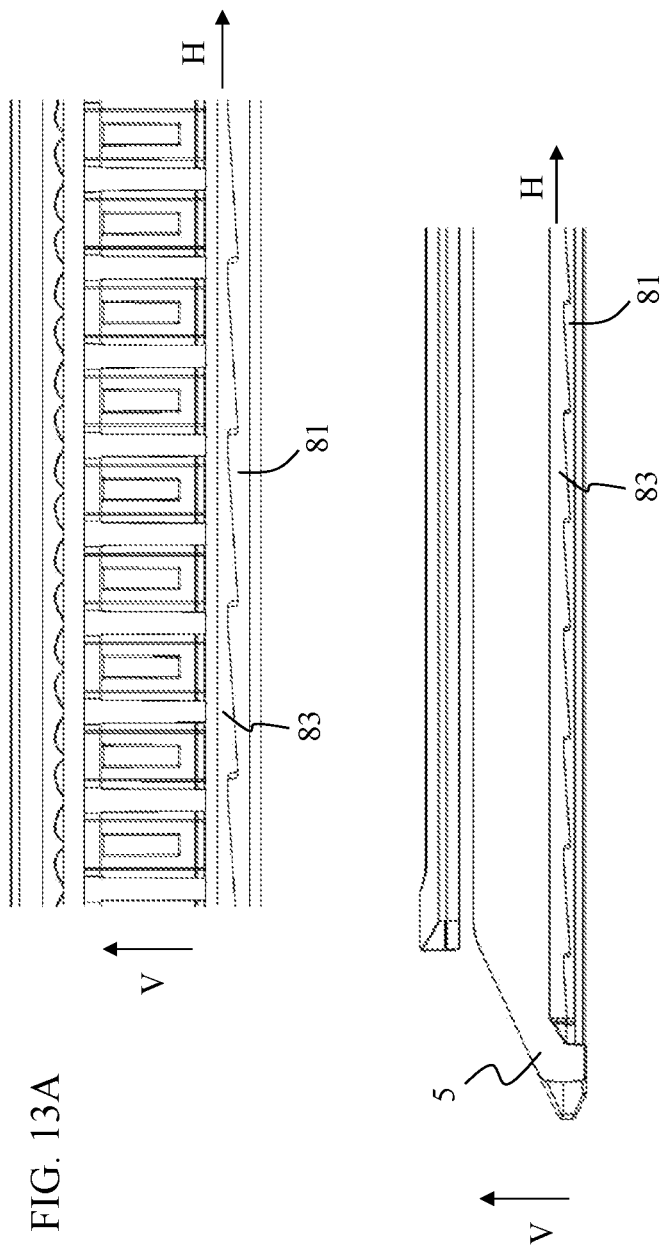

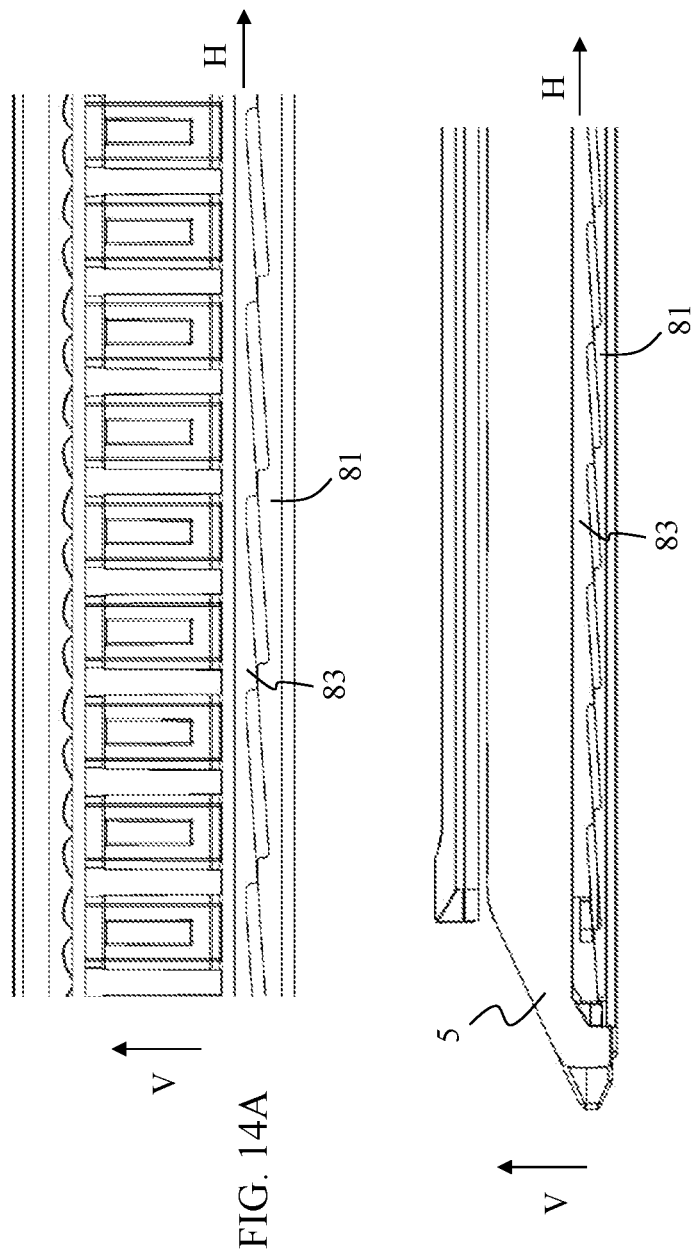

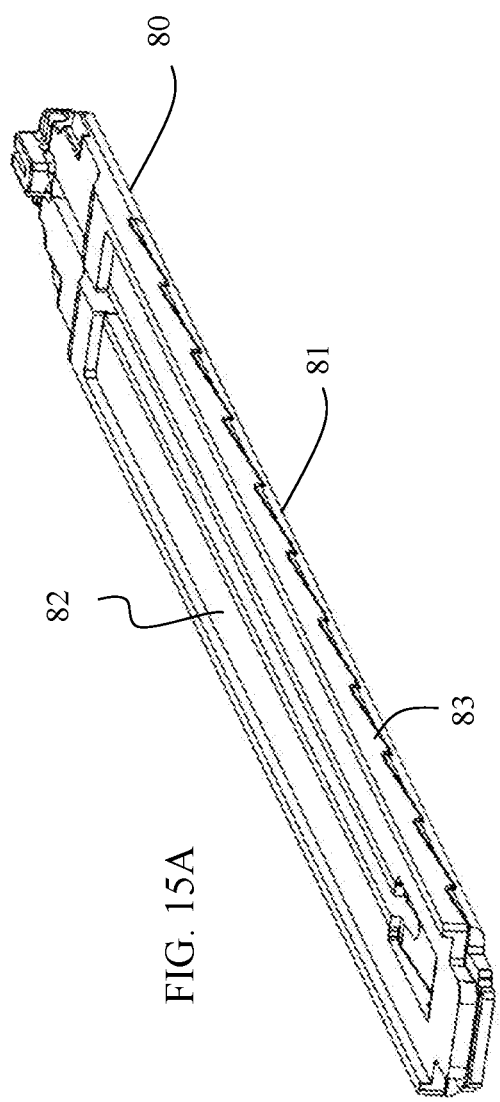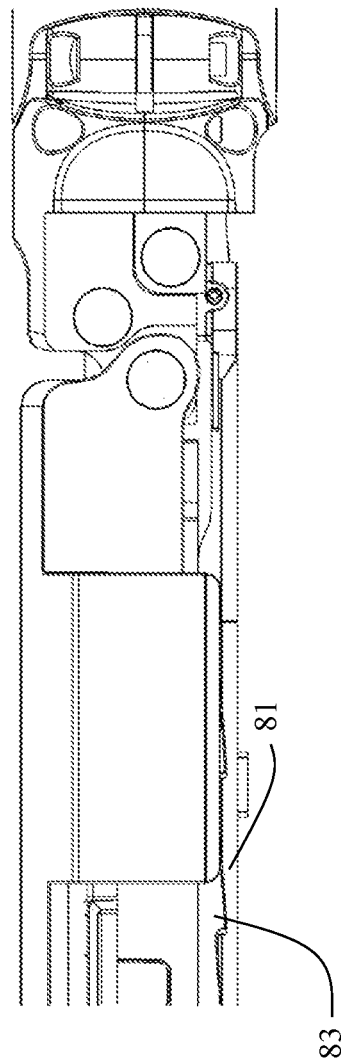
FIG. 15A
FIG. 15B

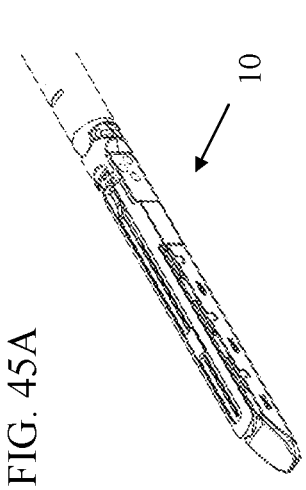
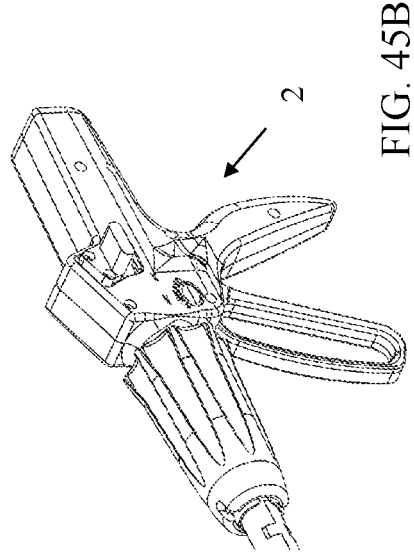
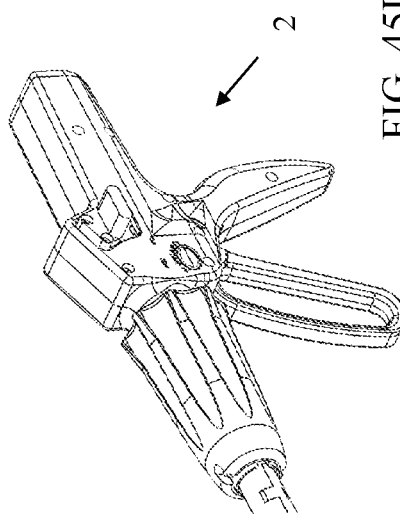
FIG. 45A
FIG. 45B
FIG. 45C
FIG. 45D

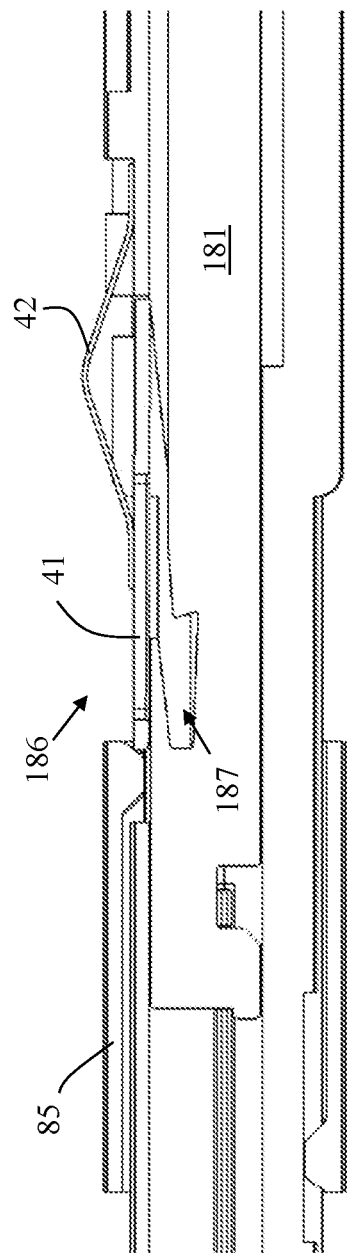
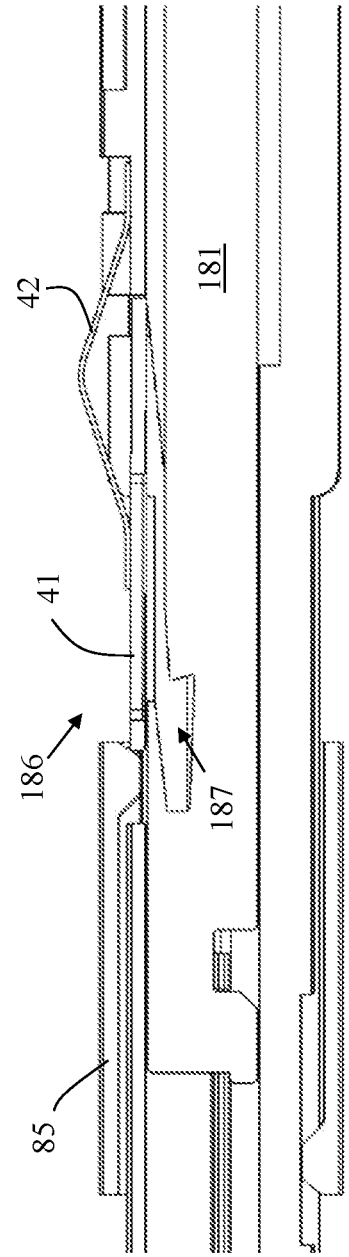
FIG. 50A
FIG. 50B

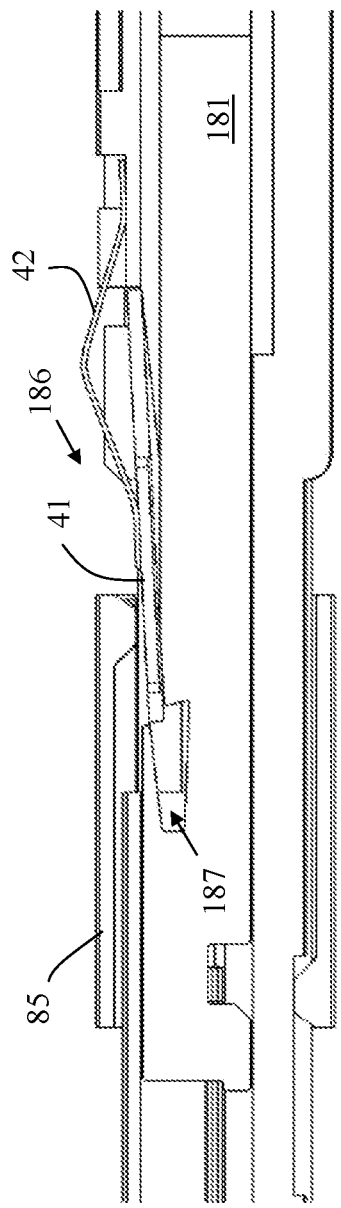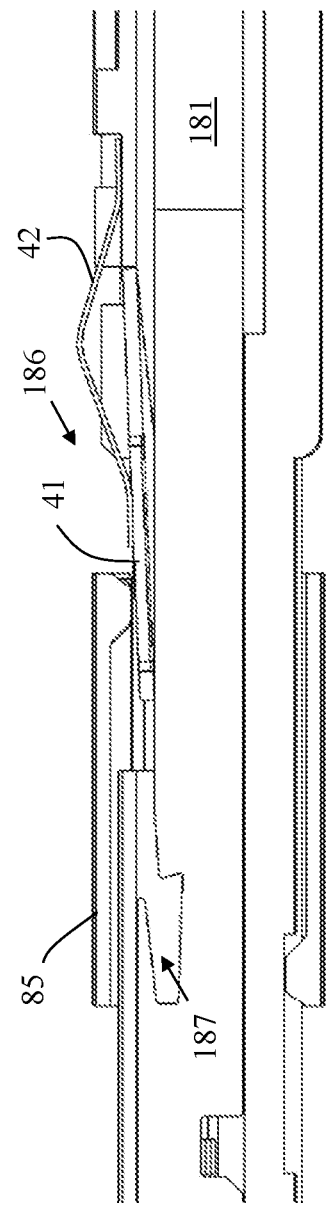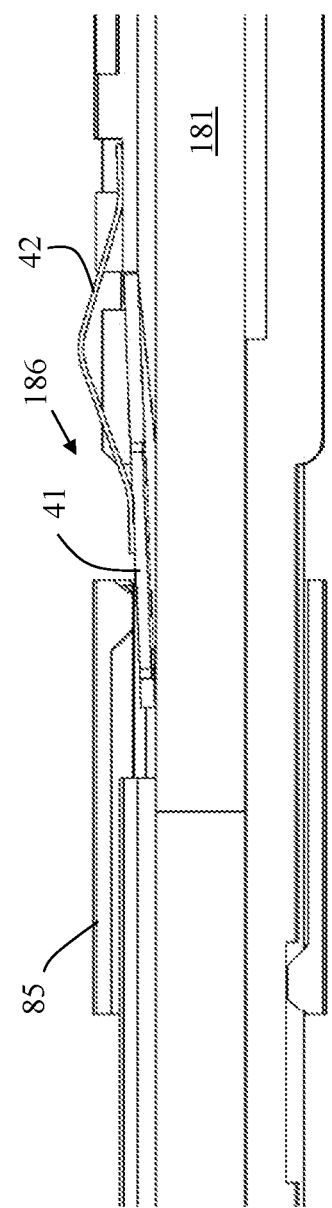

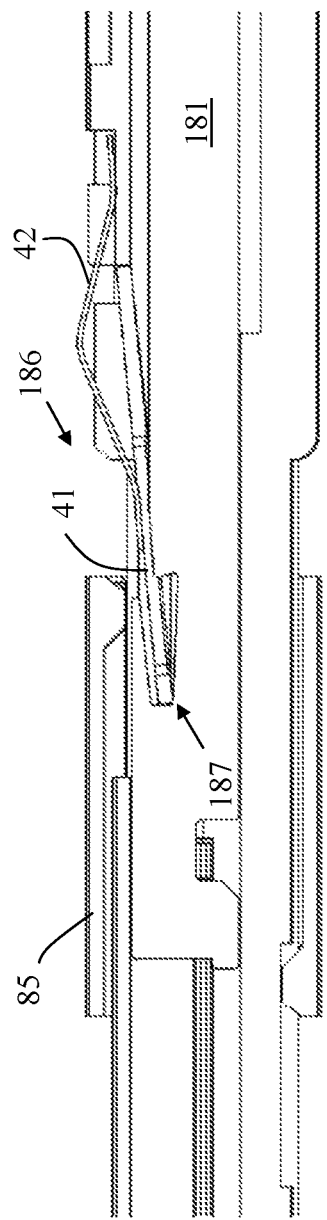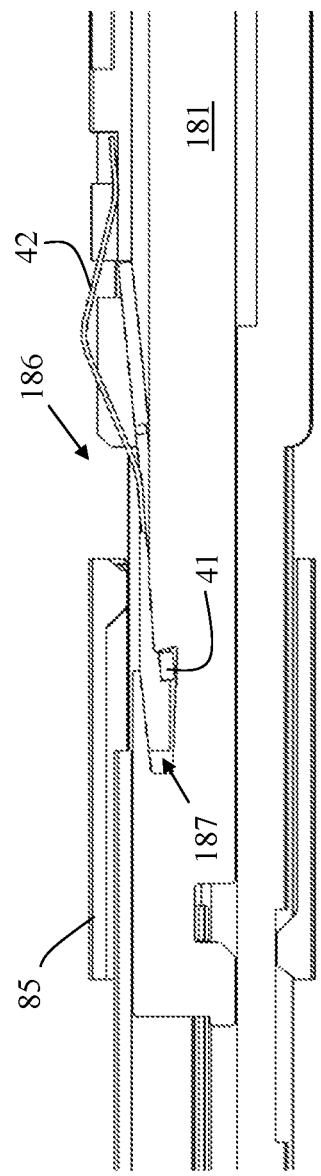
FIG. 52A
FIG. 52B

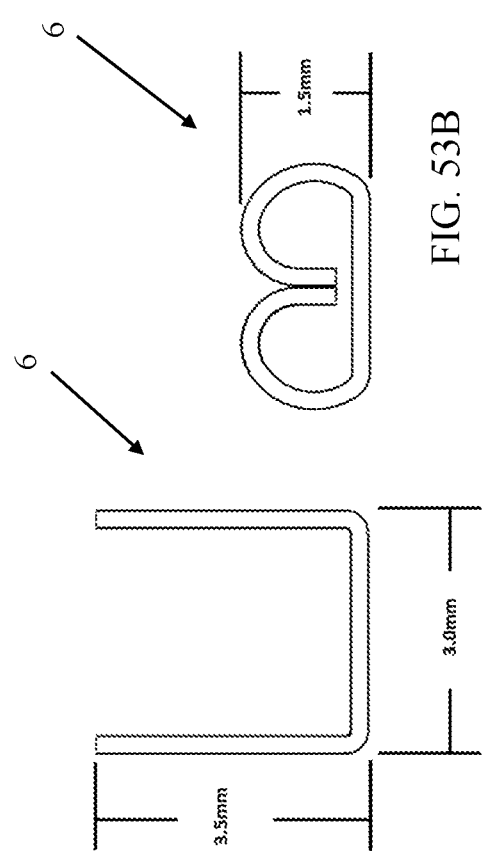

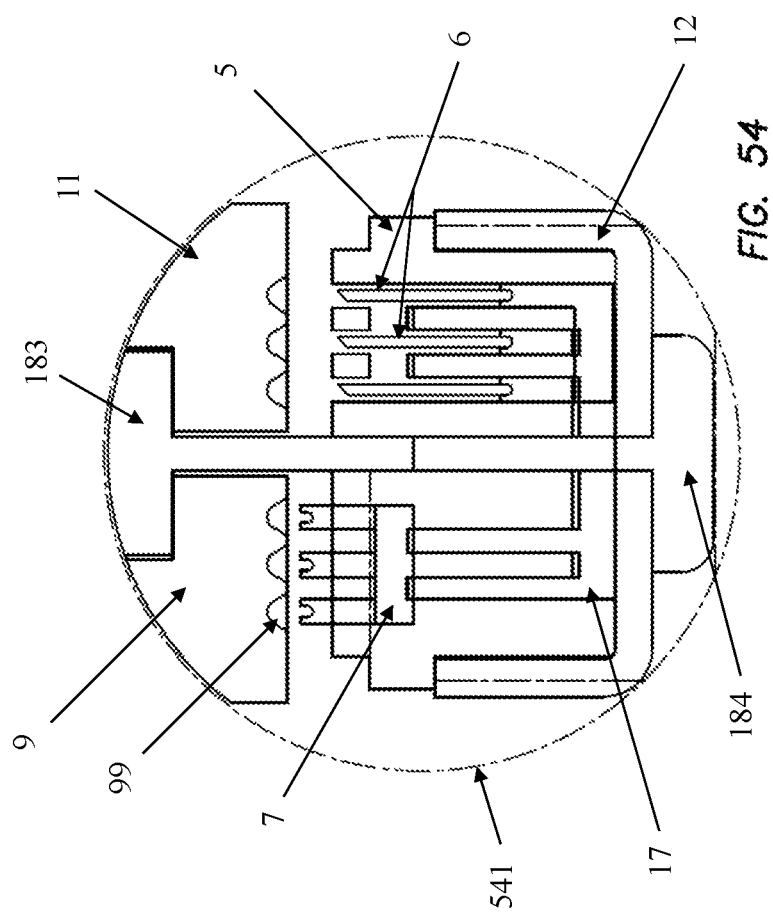

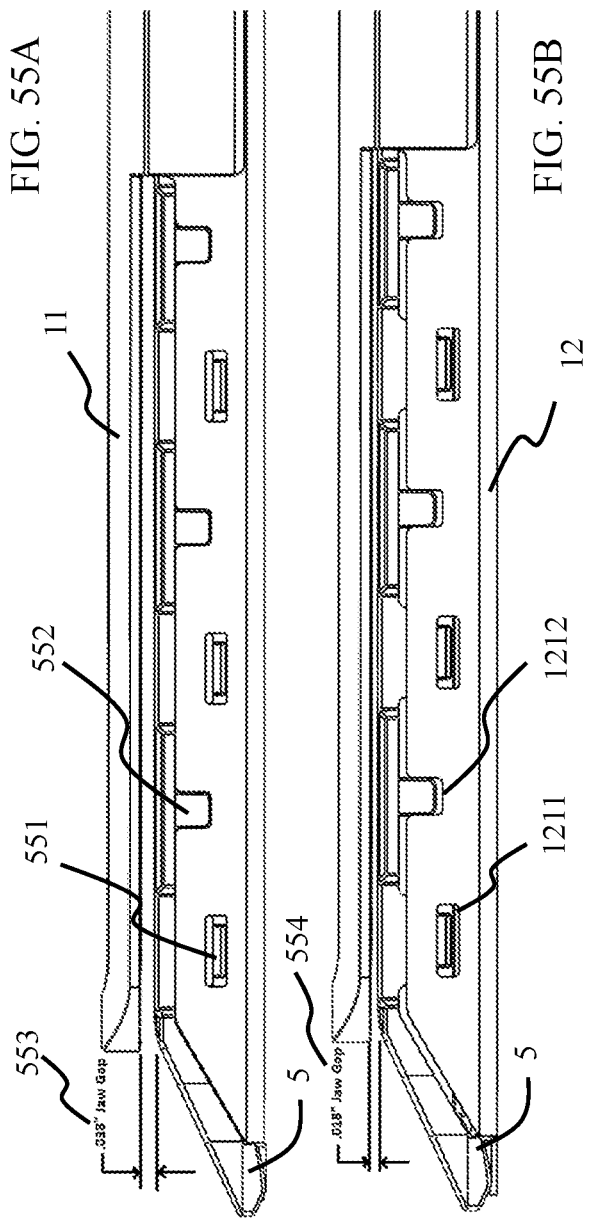

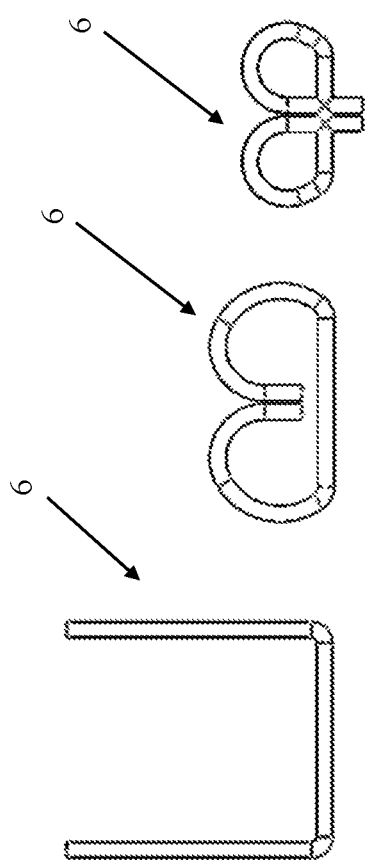

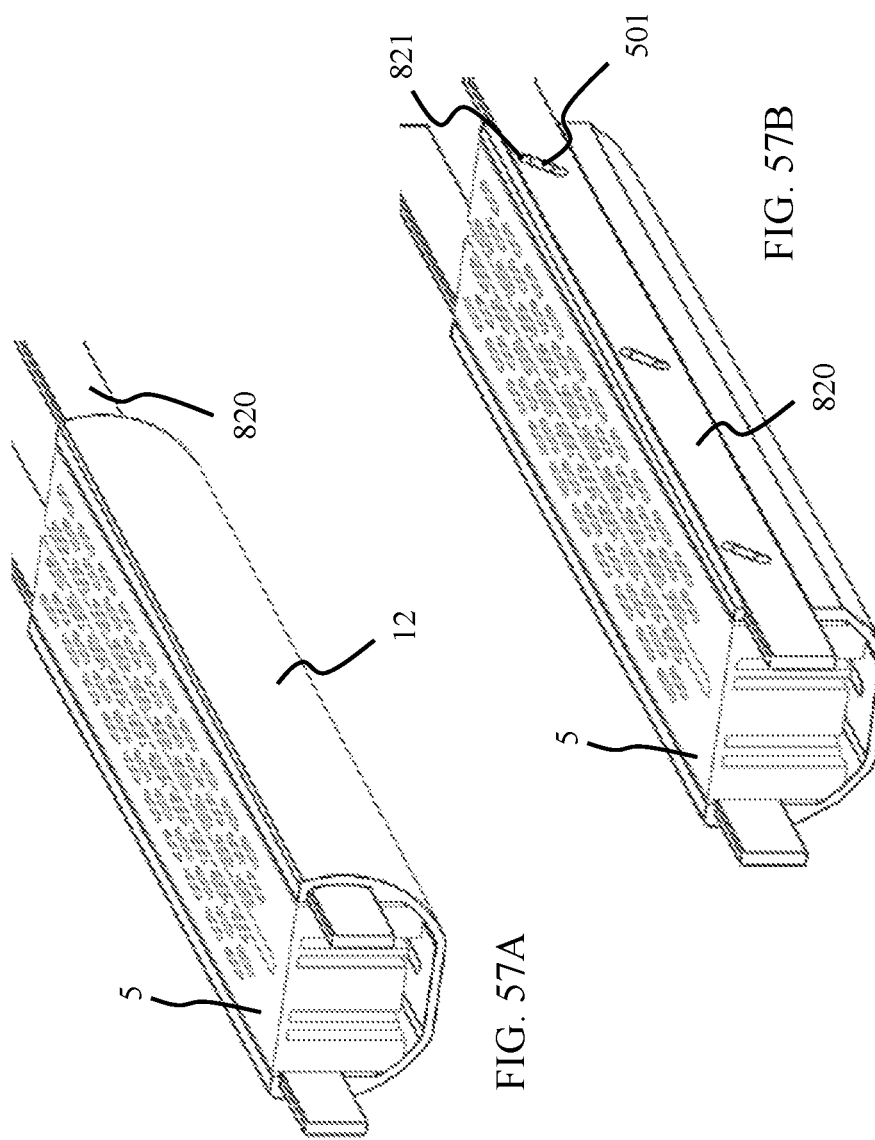

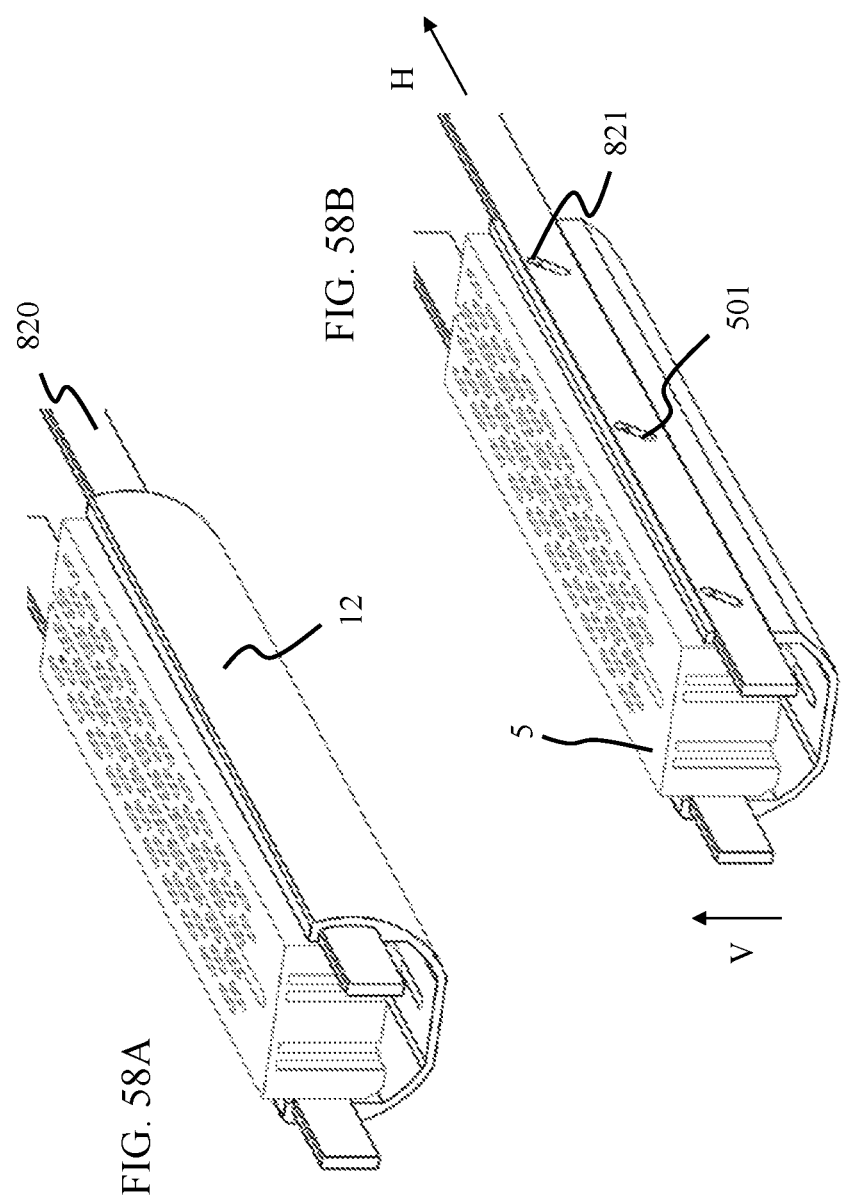

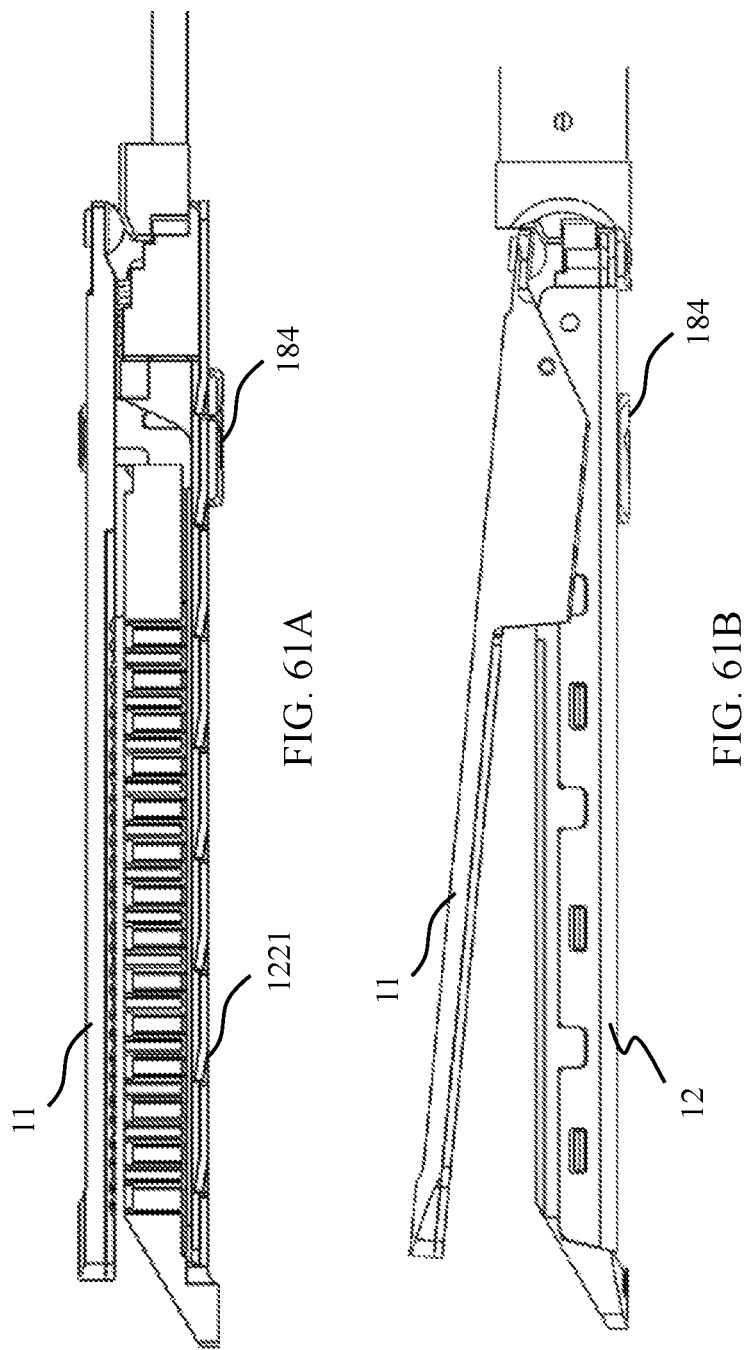

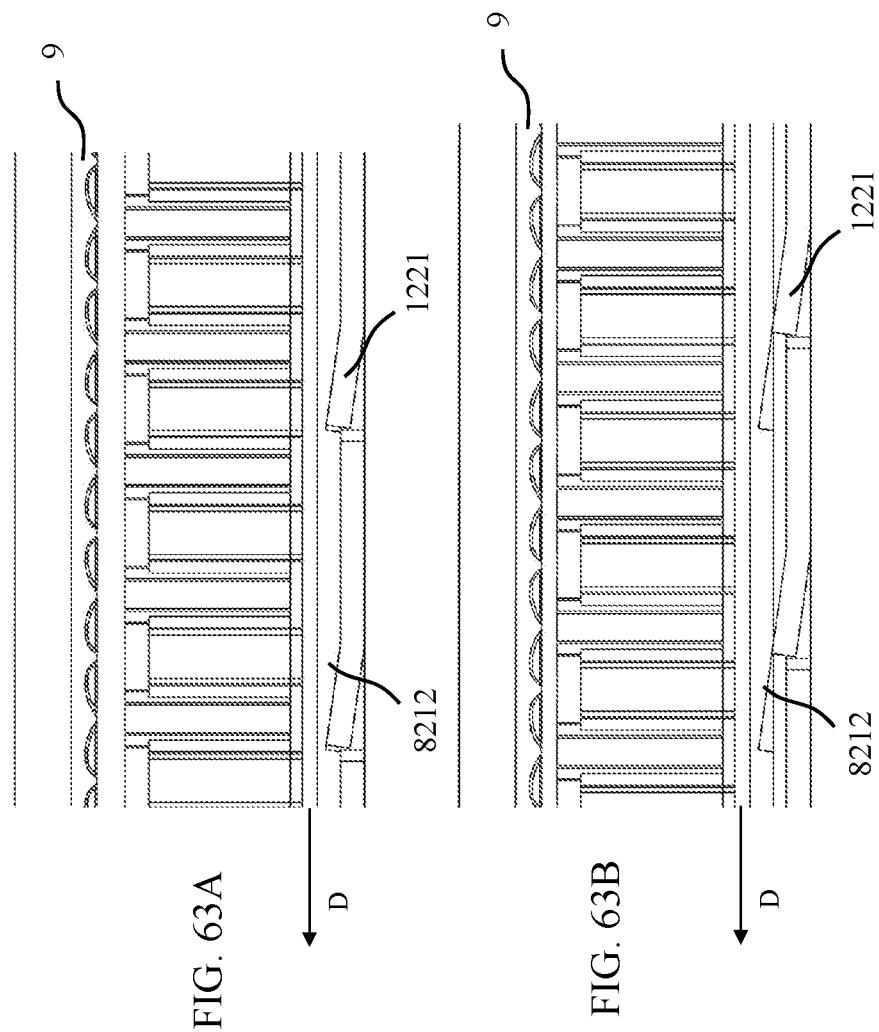

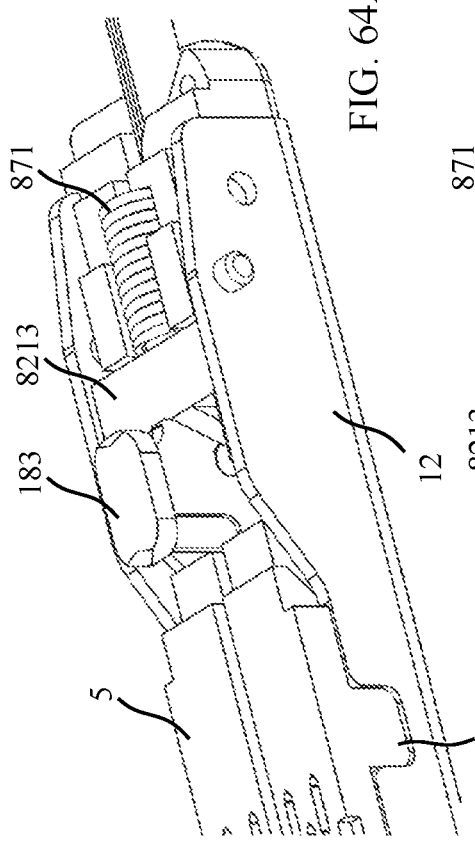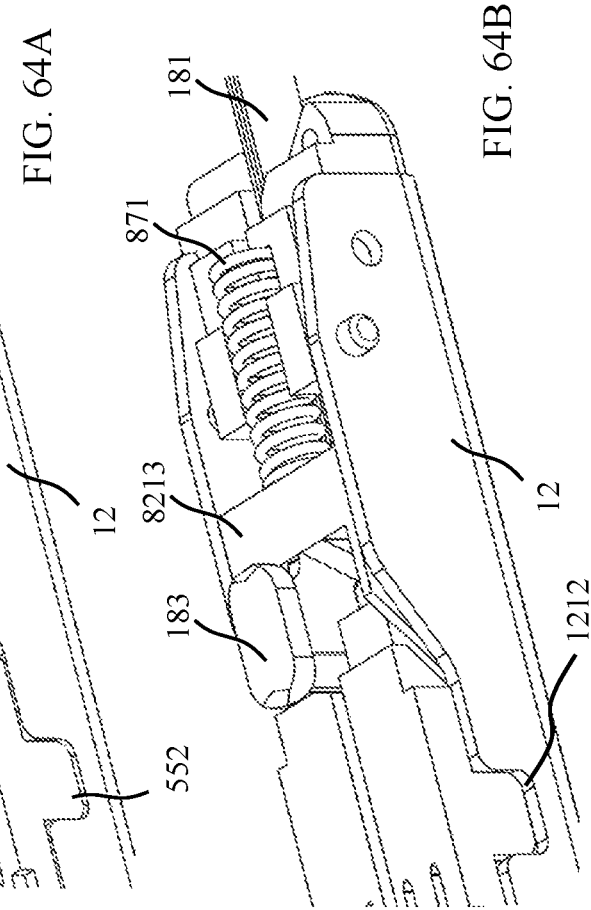
FIG. 64A
FIG. 64B

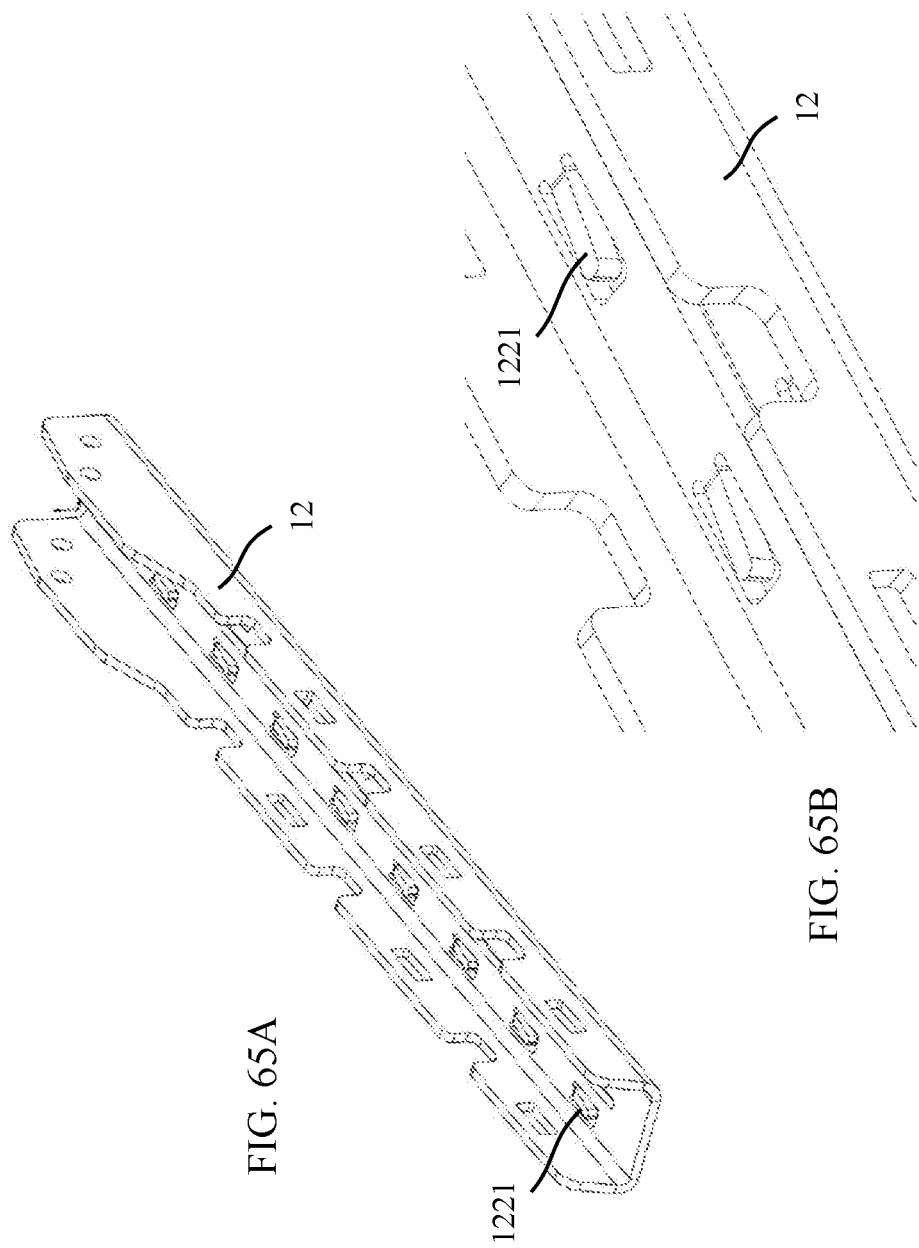

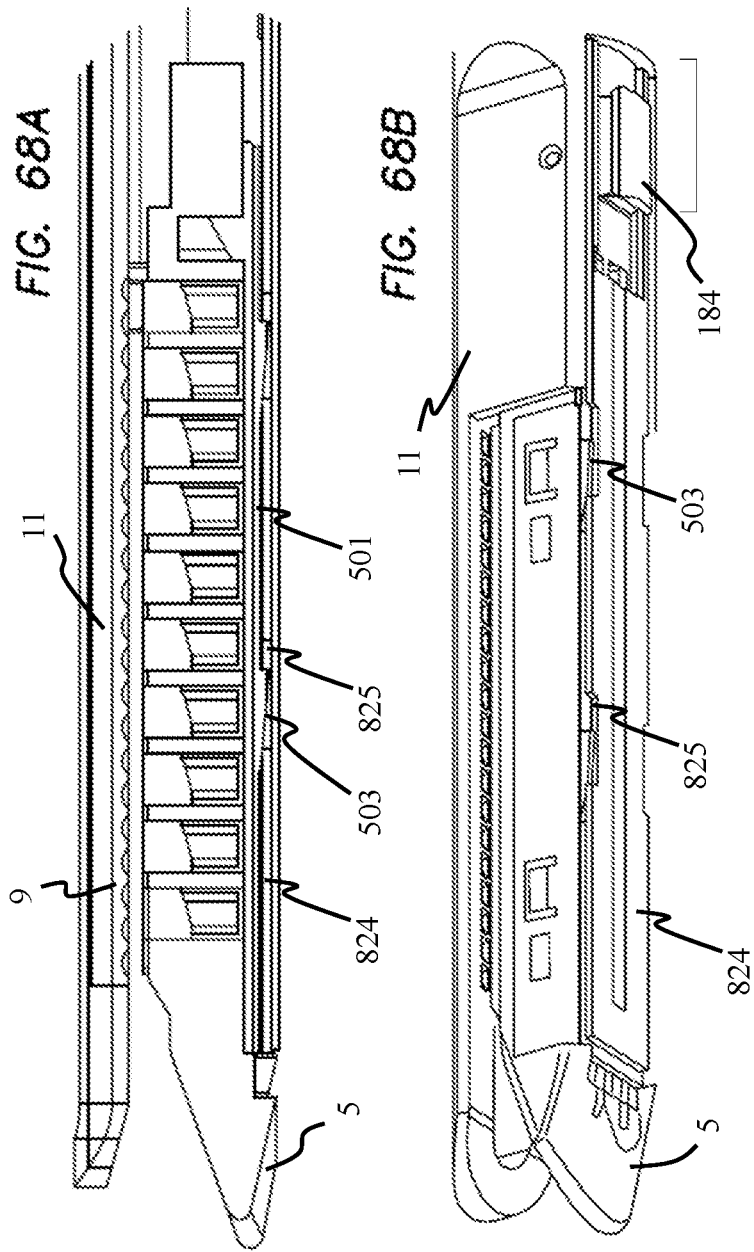

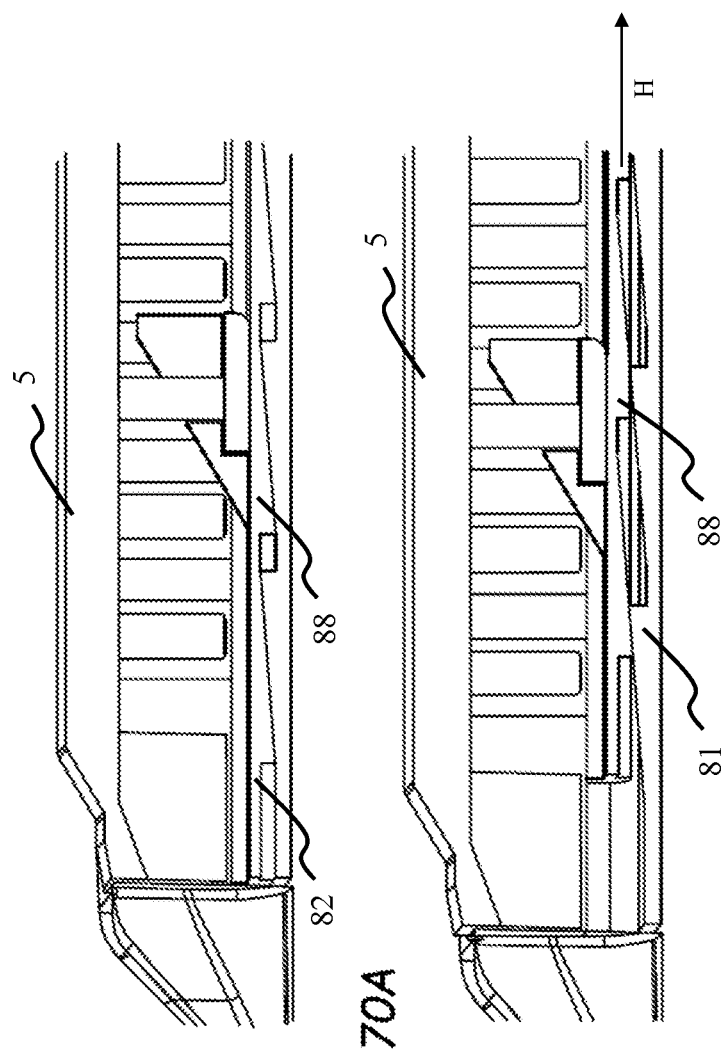

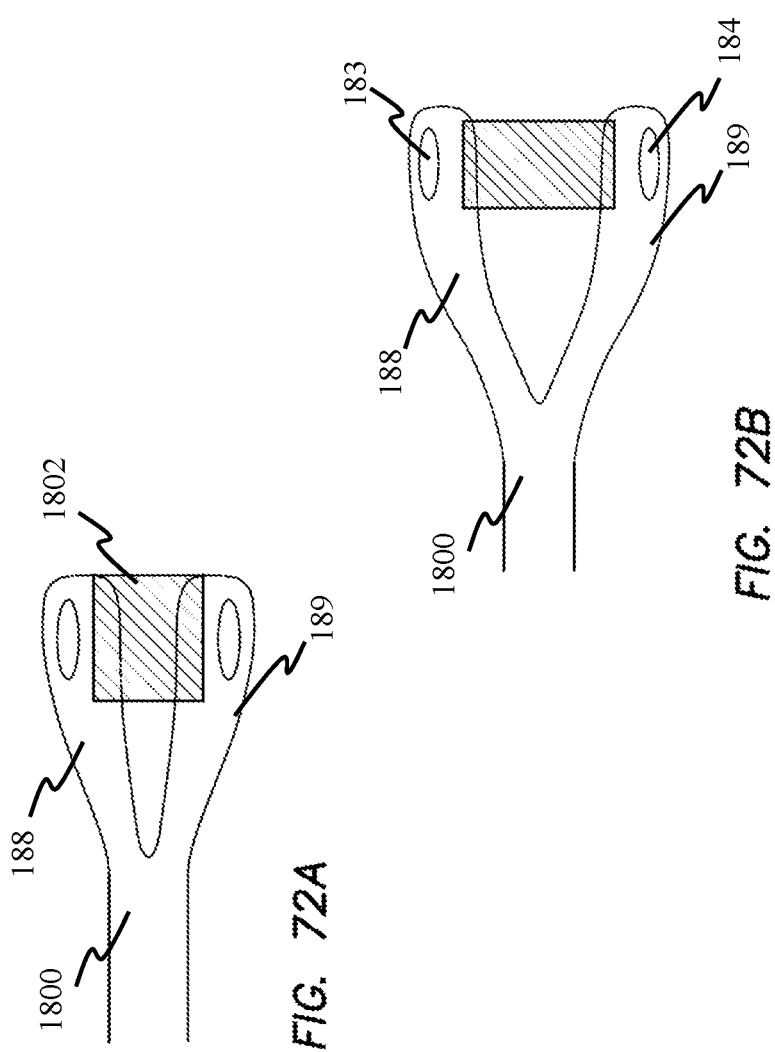

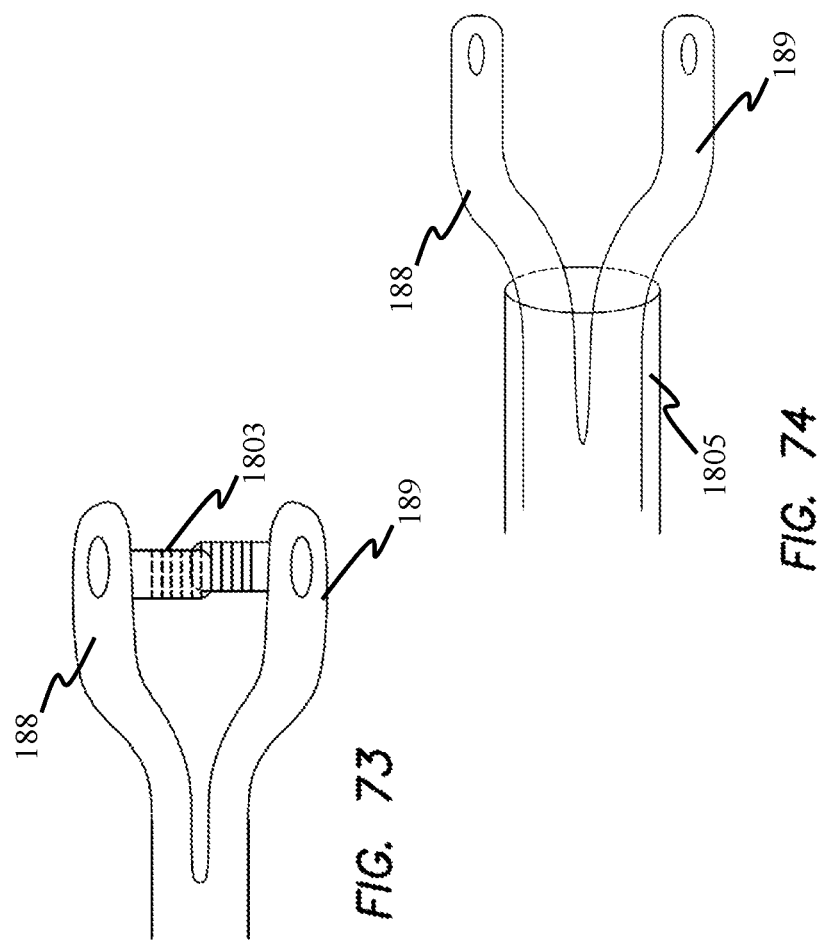

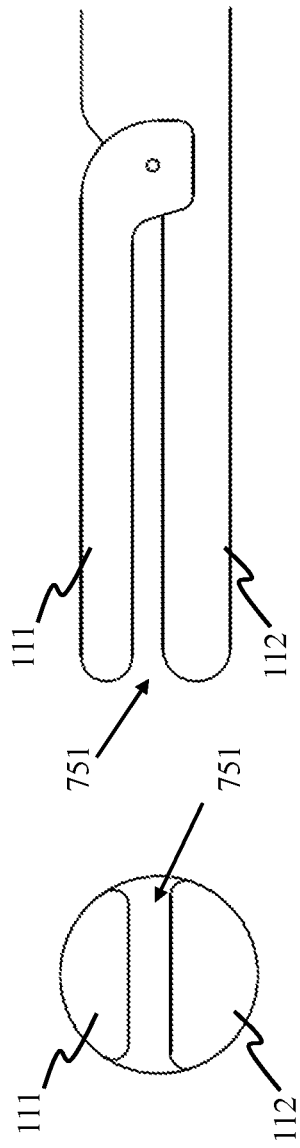
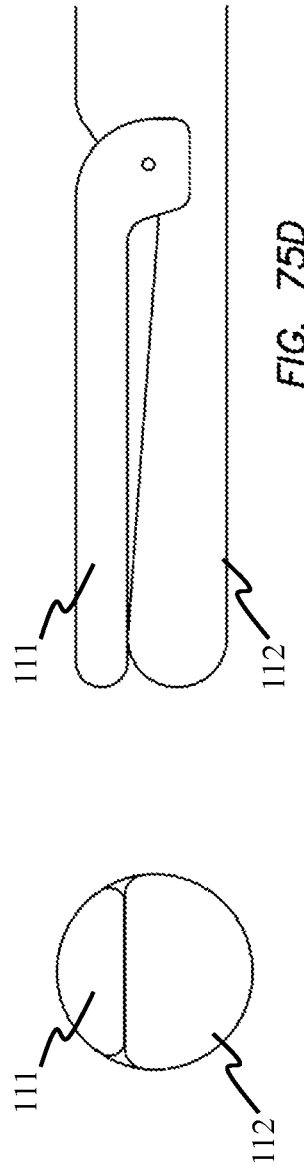

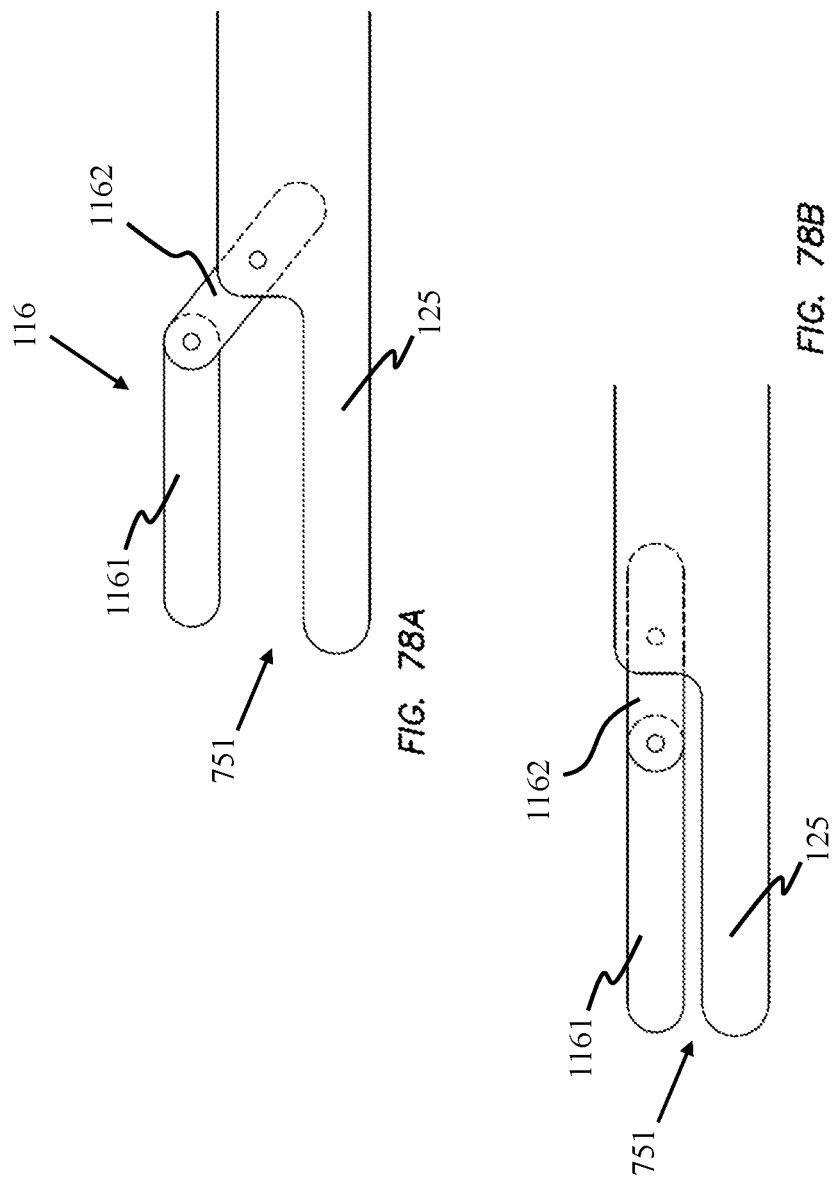

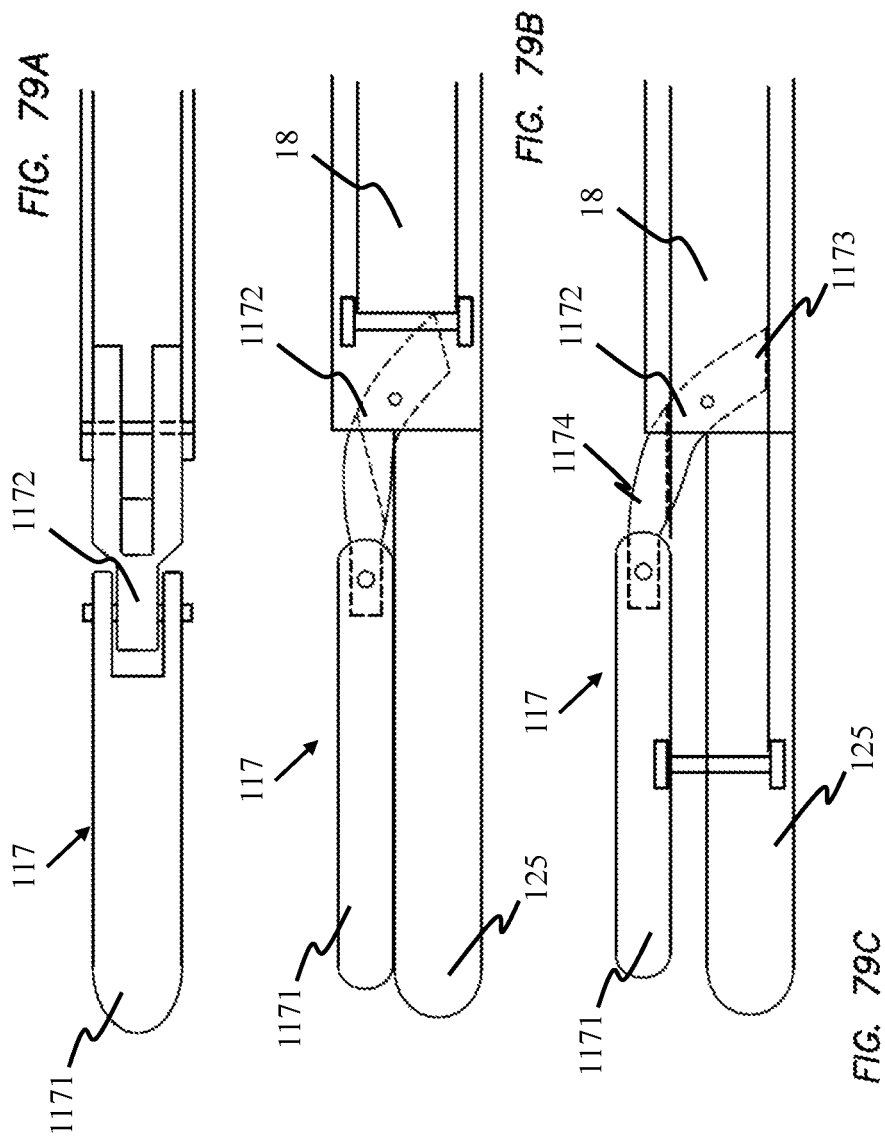

SURGICAL STAPLER WITH SELF-ADJUSTING STAPLE HEIGHT

CROSS-REFERENCE TO RELATED APPLICATION

This application is a continuation of International Application No. PCT/US2015/050103, filed Sep. 15, 2015, which claims the benefit of U.S. Application No. 62/050,513, filed on Sep. 15, 2014, the entire disclosure of which is hereby incorporated by reference as if set forth in full herein.

BACKGROUND

This application relates generally to surgical staplers and in particular to surgical staplers with a self-adjusting staple height mechanism, system and/or process.

Some surgical staplers include mechanisms to provide adjustable jaw gaps and formed staple sizes. However such staplers require user input, require an estimation or measurement of tissue, do not provide any mechanism or process to make such an estimation or measurement, and do not provide sufficient user feedback on the pressure being applied. Such staplers also do not account for limitations associated with laparoscopic surgery such as space and size constraints.

Examples of a non-laparoscopic stapler have a dial or knob on the back of the device which allows the user to manually adjust the closed staple height from a range of 1.0 mm to 2.5 mm. The devices also have a viewing window which displays the expected "Gap Setting" to the user or the expected closed staple height. Other staplers have a three position toggle switch that allows the user to manually select the closed staple height to 1.5 mm, 1.8 mm, or 2.0 mm.

Such staplers are thus fired at a fixed jaw gap height and compress all the tissue contained in the jaw of the stapler to that specific height. In some cases, users are required to choose a specific staple reload with a specific height to be used based on the user's expertise, experience of past staple firings, and perception of tissue to be fired on. Additionally, inherently the anatomies of human organs do not have constant or consistent wall thicknesses and also vary from patient to patient. Healthy tissue being compared to diseased or inflamed tissue will also widely vary in size and thickness. As such, the decision of what size staple reloads to use is a difficult one. Also, although there are a wide range of staple reloads being offered at various jaw gap heights and staple sizes, the staplers do not offer an accommodation for tissue thickness.

For some staplers, staple size is chosen by the user, prior to use, based on surgeon's perception of tissue thickness (no measuring device provided, used or contemplated) or through past experience on similar tissue. However, thickness of a particular organ within a patient can vary as well as similar anatomy in other patients. As such, choosing a correct staple size for a given tissue is difficult and it is often difficult to identify if the given tissue fits within one of four or five finite sizes identified or intended for a given staple. Instructions for use for such staplers suggest correctly sized staple can be used for a particular range of tissue thickness. However, users are not provided any mechanisms or process for accurately or efficiently measuring the tissue. Matters are thus further complicated in that multiple choices of staple sizes increase permutations for identifying the proper staple size, tissue thickness, and/or force.

Also, since the stapler is fired at one fixed height, the stapler will always deliver a staple that is for example 1.5 mm in its formed height. This can be problematic if the user chooses to fire the stapler over tissue that is outside the intended range of the device, often times limited to a 0.5 mm window. As such, the formed staple does not capture or form into the tissue and thus does not provide the intended seal or closure of the tissue by the formed staple. Hence, the formed staple is too large for the given tissue. Additionally, measuring of tissue thickness prior to firing of the stapler is not available and even if available accuracy of such a measurement would be difficult to obtain.

As such, using an incorrect staple size having an incorrect staple height for a specific tissue thickness can result in not correctly forming a staple and/or excessive compression or blood flow restriction in forming the staple that may potentially lead to other complications.

SUMMARY

A self-adjusting height reload stapler is provided that automatically adjusts to the size of tissue placed in the jaws. As such, the surgical stapler accounts for the tissue thickness and automatically adjusts based on actual tissue thickness and not based on a user's guess or estimation. The stapler thus provides sufficient tissue compression to provide a seal and hemostasis at the cut line without clamping or pressing too hard to produce ischemia and/or tissue damage.

The stapler allows for jaw gap compensation should the user choose a staple size or cartridge that is too large for the tissue being stapled across. Hence, the stapler has the ability to conform to any tissue between the maximum jaw gap height (e.g., 0.037"/0.038") and minimum jaw gap height (e.g., 0.017"/0.018") instead of firing at a single pre-determined finite height.

The stapler forms staples at a specific staple height for a particular tissue based on tissue thickness. The stapler uses pressure-force feedback from tissue being compressed within the jaws to adjust and set the proper staple height (height of the staple after being formed). The stapler jaws in contact with the tissue is able to detect and react to tissue thickness and adjust the staple height accordingly to provide an ideal closed staple height for each firing of the device for each tissue captured by the device.

In various embodiments, a stapler is provided that includes a one-way spring loaded lift that automatically adjusts a staple cartridge and/or staple formation between a range of sizes (e.g., jaw gap and/or closed staple heights). The lift is automatically released as the staple firing mechanism begins its forward translation of the firing sequence. The automatic one-way adjustment also adjusts the staple cartridge while maintaining the cartridge parallel to the anvil to provide consistent staple formations. In various embodiments, a surgical stapler comprises an automatic vertical adjustment staple cartridge.

In various embodiments, a surgical stapler comprises a first jaw comprising an anvil and a second jaw comprising a cartridge comprising a plurality of staples, the first jaw being movable towards and away from the second jaw. The stapler further comprises a cartridge lift disposed between the second jaw and the cartridge and the lift is arranged to move the cartridge towards the first jaw while the lift moves in a longitudinal direction.

In various embodiments, a surgical stapler comprises a first jaw comprising an anvil and a second jaw comprising a cartridge comprising a plurality of staples, the first jaw being movable towards and away from the second jaw. The stapler further comprises a cartridge lift disposed between the second jaw and the cartridge and the lift is arranged to move the cartridge towards the first jaw while the lift moves in a longitudinal direction. The stapler further comprises a cartridge lift spring biasing the cartridge lift proximally in the longitudinal direction.

In various embodiments, a surgical stapler comprises a first jaw comprising an anvil and a second jaw having a proximal end and a distal end and comprising a cartridge, the first jaw being movable towards and away from the second jaw. The stapler further comprises a cartridge lift disposed between the second jaw and the cartridge and the cartridge lift is biased in a proximal longitudinal direction away from the distal end of the second jaw.

In various embodiments, a surgical stapler comprises a first jaw comprising an anvil and a second jaw comprising a cartridge, the first jaw being movable towards the second jaw. The stapler further comprises an actuation beam having an upper arm and a lower arm and defining a distance between the upper and lower arms, the distance being adjustable.

In various embodiments, a surgical stapler comprises an upper jaw including an anvil and a lower jaw including a cartridge. The lower jaw is movable towards the upper jaw and a distance between the upper and lower jaws is adjustable. A proximal most portion of the jaws has a near zero gap between the upper and lower jaws.

These and other features of the invention will become more apparent with a discussion of embodiments in reference to the associated drawings.

BRIEF DESCRIPTION OF DRAWINGS

The present inventions may be understood by reference to the following description, taken in connection with the accompanying drawings in which the reference numerals designate like parts throughout the figures thereof.

FIG. 1A is a side view of a staple and transector receptacle of a surgical stapler in accordance with various embodiments of the present invention.

FIG. 1B is a side view of an actuator of a surgical stapler in accordance with various embodiments of the present invention.

FIG. 3A is a perspective view of a staple and transector receptacle of a surgical stapler in accordance with various embodiments of the present invention.

FIG. 3B is a side view of a staple and transector receptacle of a surgical stapler in accordance with various embodiments of the present invention.

FIG. 8A is a top view of a staple pusher in accordance with various embodiments of the present invention.

FIG. 8B is a perspective view of a staple pusher in accordance with various embodiments of the present invention.

FIG. 8C is a perspective view of a staple pusher in accordance with various embodiments of the present invention.

FIG. 9A is a perspective view of a staple and transector receptacle of a surgical stapler in accordance with various embodiments of the present invention.

FIG. 9B is a perspective view of a staple and transector receptacle of a surgical stapler in accordance with various embodiments of the present invention.

FIG. 12A is a front view of a staple and transector receptacle of a surgical stapler in accordance with various embodiments of the present invention.

FIG. 12B is a side cross-sectional view of a staple and transector receptacle of a surgical stapler in accordance with various embodiments of the present invention.

FIG. 13A is a side cross-sectional view of a staple and transector receptacle of a surgical stapler in accordance with various embodiments of the present invention.

FIG. 13B is a side cross-sectional view of a staple and transector receptacle of a surgical stapler in accordance with various embodiments of the present invention.

FIG. 14A is a side cross-sectional view of a staple and transector receptacle of a surgical stapler in accordance with various embodiments of the present invention.

FIG. 14B is a side cross-sectional view of a staple and transector receptacle of a surgical stapler in accordance with various embodiments of the present invention.

FIG. 15A is a perspective view of portions of a staple and transector receptacle of a surgical stapler in accordance with various embodiments of the present invention.

FIG. 15B is a side cross-sectional view of portions of a staple and transector receptacle of a surgical stapler in accordance with various embodiments of the present invention.

FIG. 45A is a perspective view of a staple and transector receptacle of a surgical stapler in accordance with various embodiments of the present invention.

FIG. 45B is perspective view of an actuator of a surgical stapler in accordance with various embodiments of the present invention.

FIG. 45C is perspective view of a staple and transector receptacle of a surgical stapler in accordance with various embodiments of the present invention.

FIG. 45D is a perspective view of an actuator of a surgical stapler in accordance with various embodiments of the present invention.

FIG. 50A is a side cross-sectional view of portions of a staple and transector receptacle of a surgical stapler in accordance with various embodiments of the present invention.

FIG. 50B is a side cross-sectional view of portions of a staple and transector receptacle of a surgical stapler in accordance with various embodiments of the present invention.

FIG. 51A is a side cross-sectional view of portions of a staple and transector receptacle of a surgical stapler in accordance with various embodiments of the present invention.

FIG. 51B is a side cross-sectional view of portions of a staple and transector receptacle of a surgical stapler in accordance with various embodiments of the present invention.

FIG. 51C is a side cross-sectional view of portions of a staple and transector receptacle of a surgical stapler in accordance with various embodiments of the present invention.

FIG. 52A is a side cross-sectional view of portions of a staple and transector receptacle of a surgical stapler in accordance with various embodiments of the present invention.

FIG. 52B is a side cross-sectional view of portions of a staple and transector receptacle of a surgical stapler in accordance with various embodiments of the present invention.

FIG. 53A is a side view of staple in accordance with various embodiments of the present invention.

FIG. 53B is a side view of staple in accordance with various embodiments of the present invention.

FIG. 54 is a front cross-sectional view of portions of a staple and transector receptacle of a surgical stapler in accordance with various embodiments of the present invention.

FIG. 55A is side view of a staple and transector receptacle of a surgical stapler in accordance with various embodiments of the present invention.

FIG. 55B is a side view of a staple and transector receptacle of a surgical stapler in accordance with various embodiments of the present invention.

FIG. 56A is a side view of a staple in accordance with various embodiments of the present invention.

FIG. 56B is a side view of a staple in accordance with various embodiments of the present invention.

FIG. 56C is a side view of a staple in accordance with various embodiments of the present invention.

FIG. 57A is a perspective view of portions of a staple and transector receptacle of a surgical stapler in accordance with various embodiments of the present invention.

FIG. 57B is a perspective view of portions of a staple and transector receptacle of a surgical stapler in accordance with various embodiments of the present invention.

FIG. 58A is a perspective view of portions of a staple and transector receptacle of a surgical stapler in accordance with various embodiments of the present invention.

FIG. 58B is a perspective view of portions of a staple and transector receptacle of a surgical stapler in accordance with various embodiments of the present invention.

FIG. 61A is side cross-sectional view of portions of a staple and transector receptacle of a surgical stapler in accordance with various embodiments of the present invention.

FIG. 61B is a side view of a staple and transector receptacle of a surgical stapler in accordance with various embodiments of the present invention.

FIG. 63A is a side cross-sectional view of a staple and transector receptacle of a surgical stapler in accordance with various embodiments of the present invention.

FIG. 63B is a side cross-sectional view of a staple and transector receptacle of a surgical stapler in accordance with various embodiments of the present invention.

FIG. 64A is a perspective view of a staple and transector receptacle of a surgical stapler in accordance with various embodiments of the present invention.

FIG. 64B is a perspective view of a staple and transector receptacle of a surgical stapler in accordance with various embodiments of the present invention.

FIG. 65A is a perspective view of a portion of a staple and transector receptacle of a surgical stapler in accordance with various embodiments of the present invention.

FIG. 65B is a perspective view of a portion of a staple and transector receptacle of a surgical stapler in accordance with various embodiments of the present invention.

FIG. 68A is a side cross-sectional view of a staple and transector receptacle of a surgical stapler in accordance with various embodiments of the present invention.

FIG. 68B is a bottom perspective view of a staple and transector receptacle of a surgical stapler in accordance with various embodiments of the present invention.

FIG. 70A is a side cross-sectional view of a staple and transector receptacle of a surgical stapler in accordance with various embodiments of the present invention.

FIG. 70B is a side cross-sectional view of a staple and transector receptacle of a surgical stapler in accordance with various embodiments of the present invention.

FIG. 72A is a side view of portions of a staple and transector receptacle of a surgical stapler in accordance with various embodiments of the present invention.

FIG. 72B is a side view of portions of a staple and transector receptacle of a surgical stapler in accordance with various embodiments of the present invention.

FIG. 73 is a side view of portions of a staple and transector receptacle of a surgical stapler in accordance with various embodiments of the present invention.

FIG. 74 is a side view of portions of a staple and transector receptacle of a surgical stapler in accordance with various embodiments of the present invention.

FIG. 75A is a front view of portions of a staple and transector receptacle of a surgical stapler in accordance with various embodiments of the present invention.

FIG. 75B is a side view of portions of a staple and transector receptacle of a surgical stapler in accordance with various embodiments of the present invention.

FIG. 75C is a front view of portions of a staple and transector receptacle of a surgical stapler in accordance with various embodiments of the present invention.

FIG. 75D is a side view of portions of a staple and transector receptacle of a surgical stapler in accordance with various embodiments of the present invention.

FIG. 76 is a front cross-sectional view of a staple and transector receptacle of a surgical stapler in accordance with various embodiments of the present invention.

FIG. 77A is a side view of a staple and transector receptacle of a surgical stapler in accordance with various embodiments of the present invention.

FIG. 77B is a side view of a staple and transector receptacle of a surgical stapler in accordance with various embodiments of the present invention.

FIG. 78A is a side view of a staple and transector receptacle of a surgical stapler in accordance with various embodiments of the present invention.

FIG. 78B is a side view of a staple and transector receptacle of a surgical stapler in accordance with various embodiments of the present invention.

FIG. 79A is a top view of a staple and transector receptacle of a surgical stapler in accordance with various embodiments of the present invention.

FIG. 79B is a side view of a staple and transector receptacle of a surgical stapler in accordance with various embodiments of the present invention.

FIG. 79C is a side view of a staple and transector receptacle of a surgical stapler in accordance with various embodiments of the present invention.

DETAILED DESCRIPTION

Figure 2A:
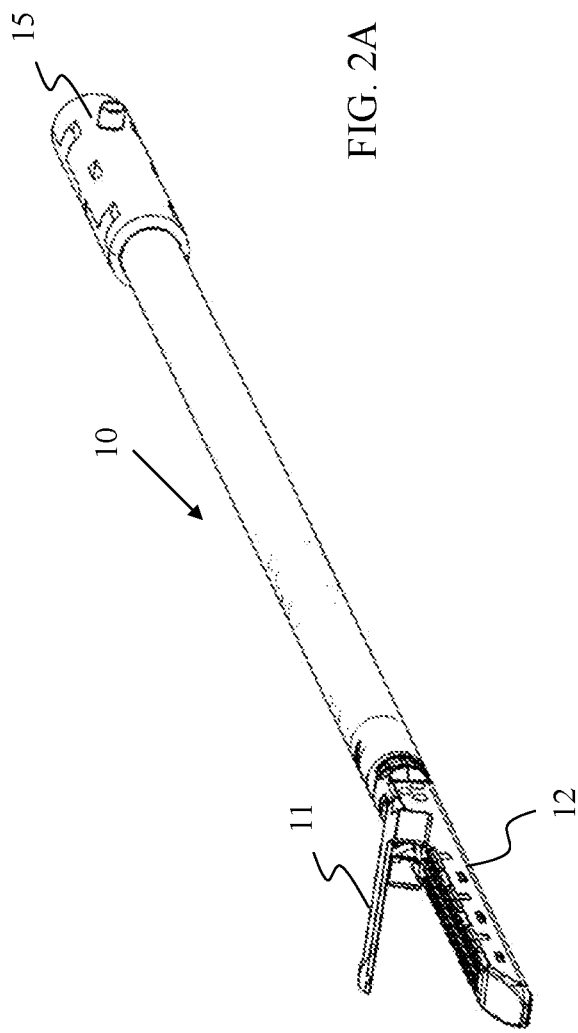
FIG. 2A is a perspective view of a staple and transector receptacle of a surgical stapler in accordance with various embodiments of the present invention.
Figure 2B:
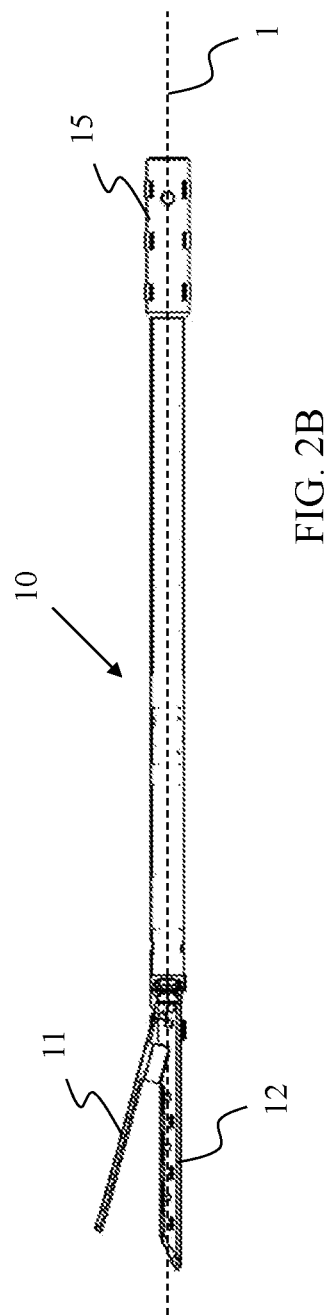
FIG. 2B is a side view of a staple and transector receptacle of a surgical stapler in accordance with various embodiments of the present invention.
Figure 4:
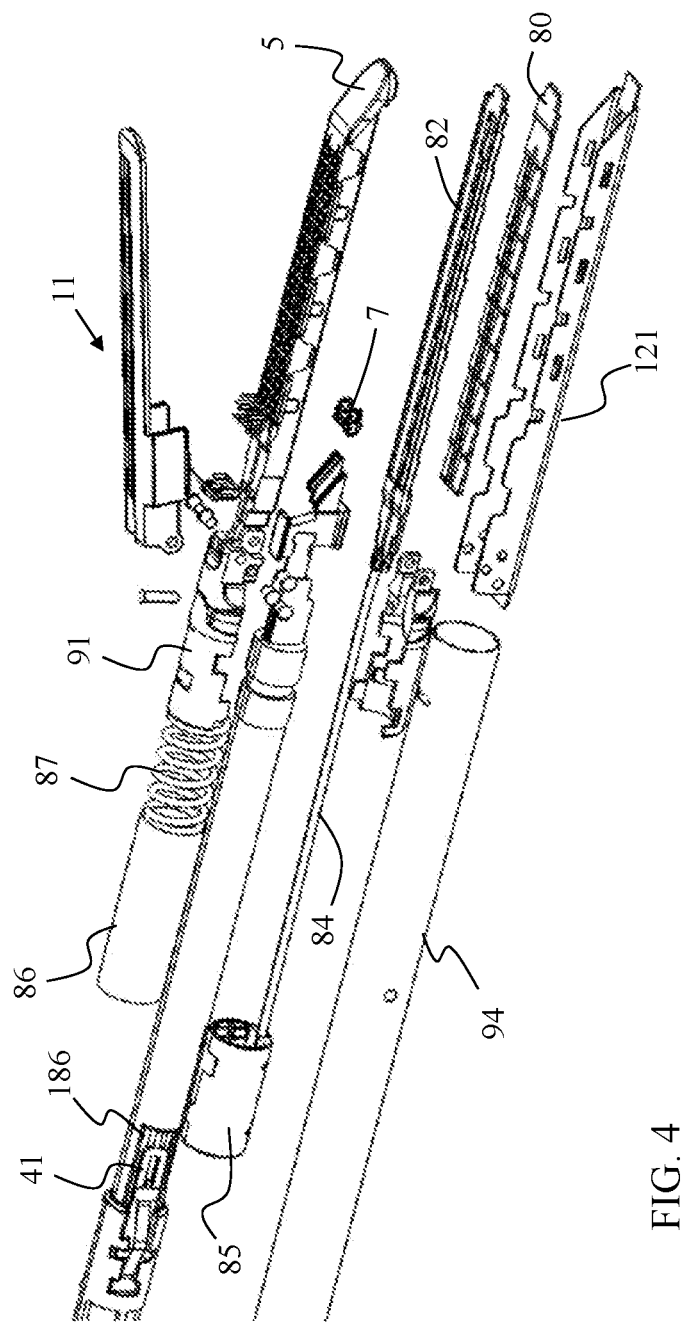
FIG. 4 is an exploded view of a staple and transector receptacle of a surgical stapler in accordance with various embodiments of the present invention.
Figure 5:
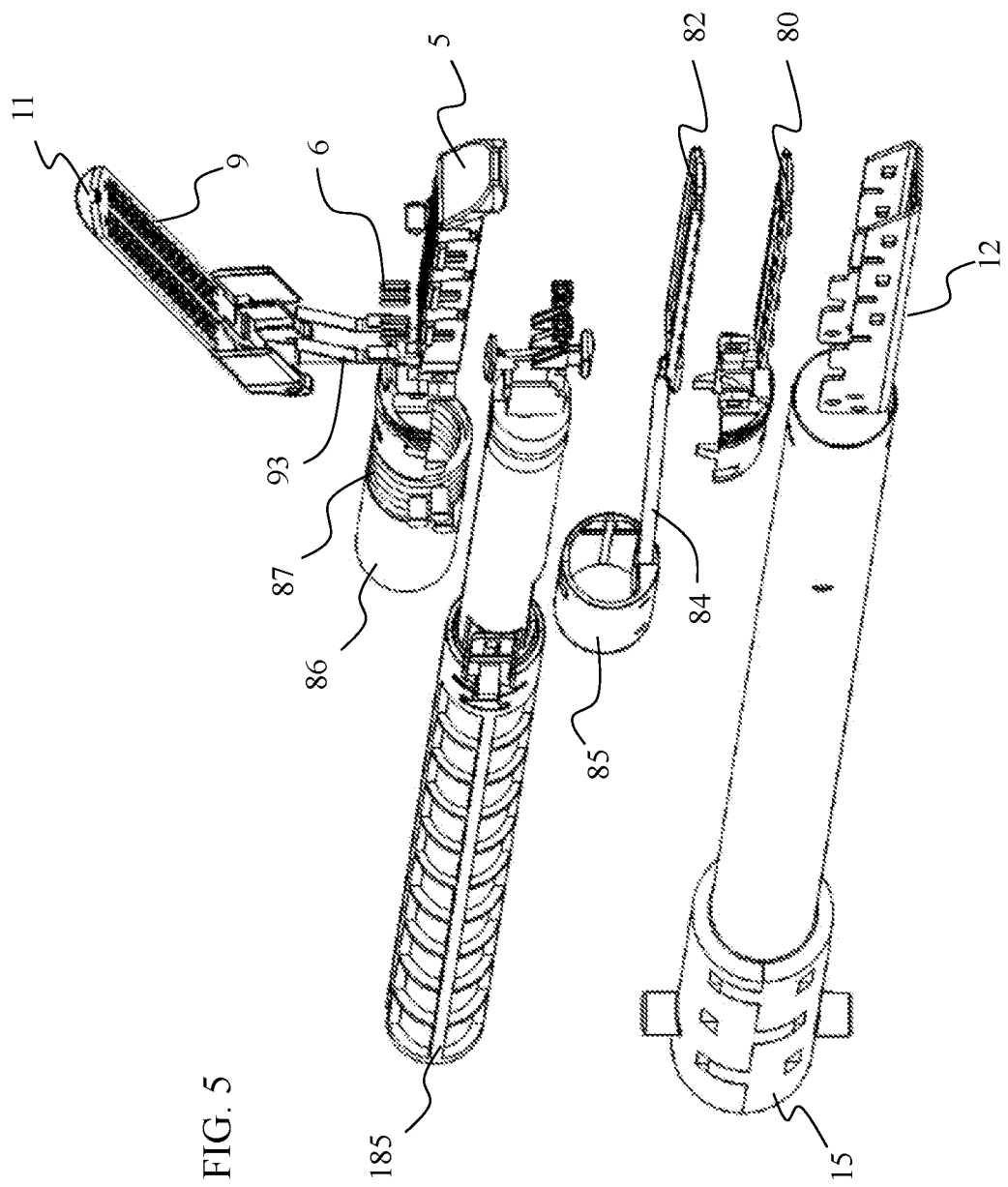
FIG. 5 is an exploded view of a staple and transector receptacle of a surgical stapler in accordance with various embodiments of the present invention.
Figure 6:
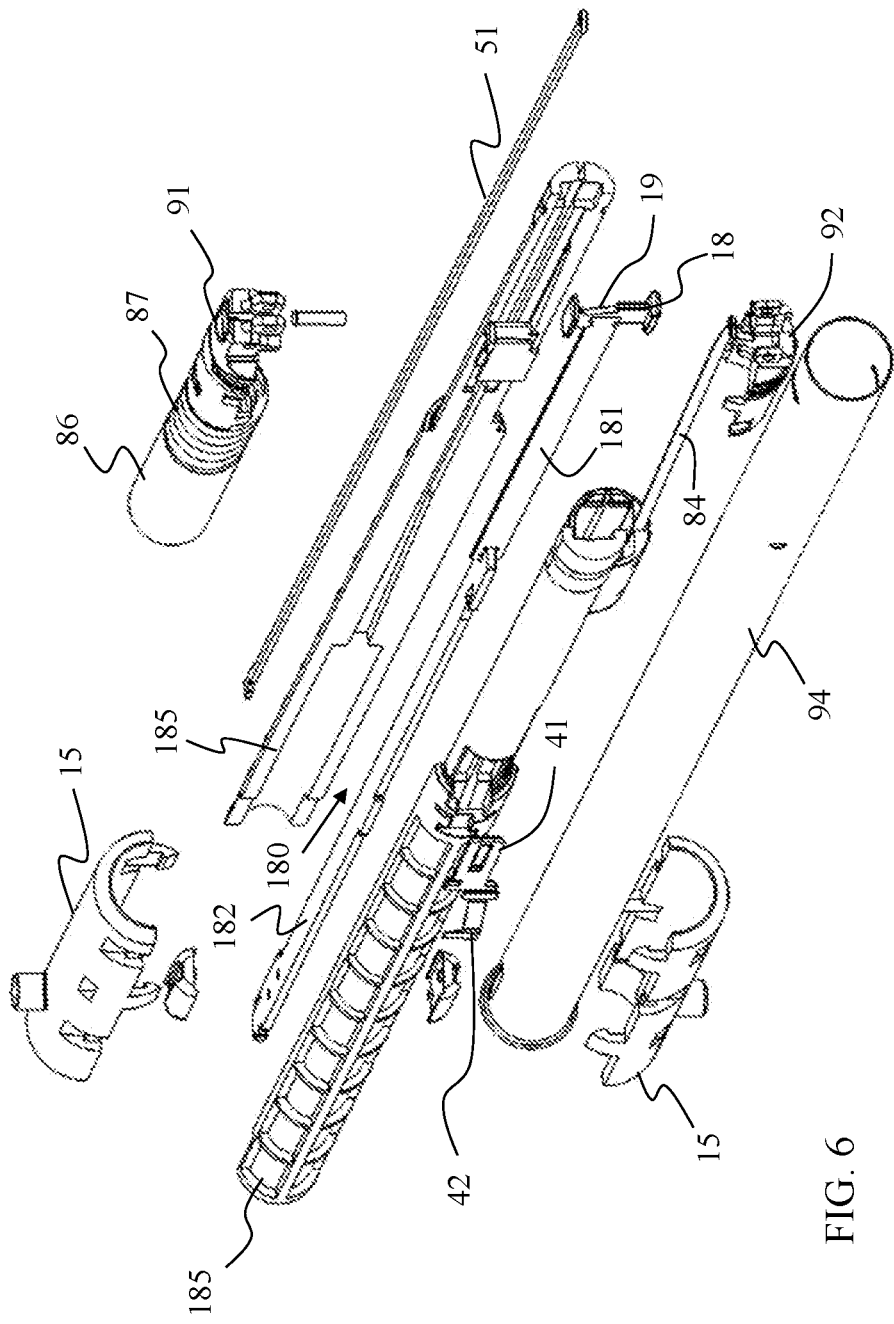
FIG. 6 is an exploded view of a staple and transector receptacle of a surgical stapler in accordance with various embodiments of the present invention.
Figure 7A:
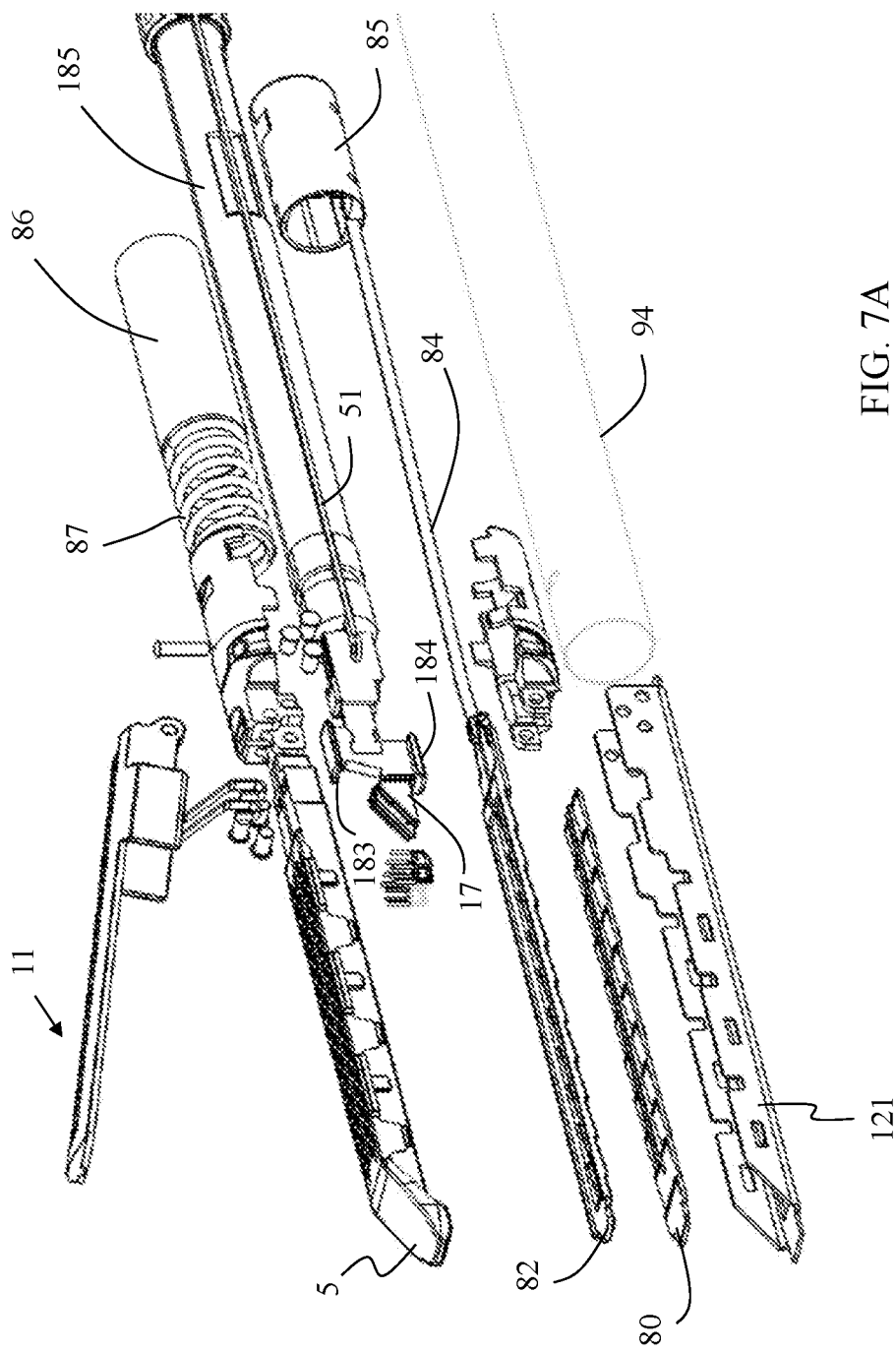
FIG. 7A is an exploded view of a staple and transector receptacle of a surgical stapler in accordance with various embodiments of the present invention.
Figure 7B:
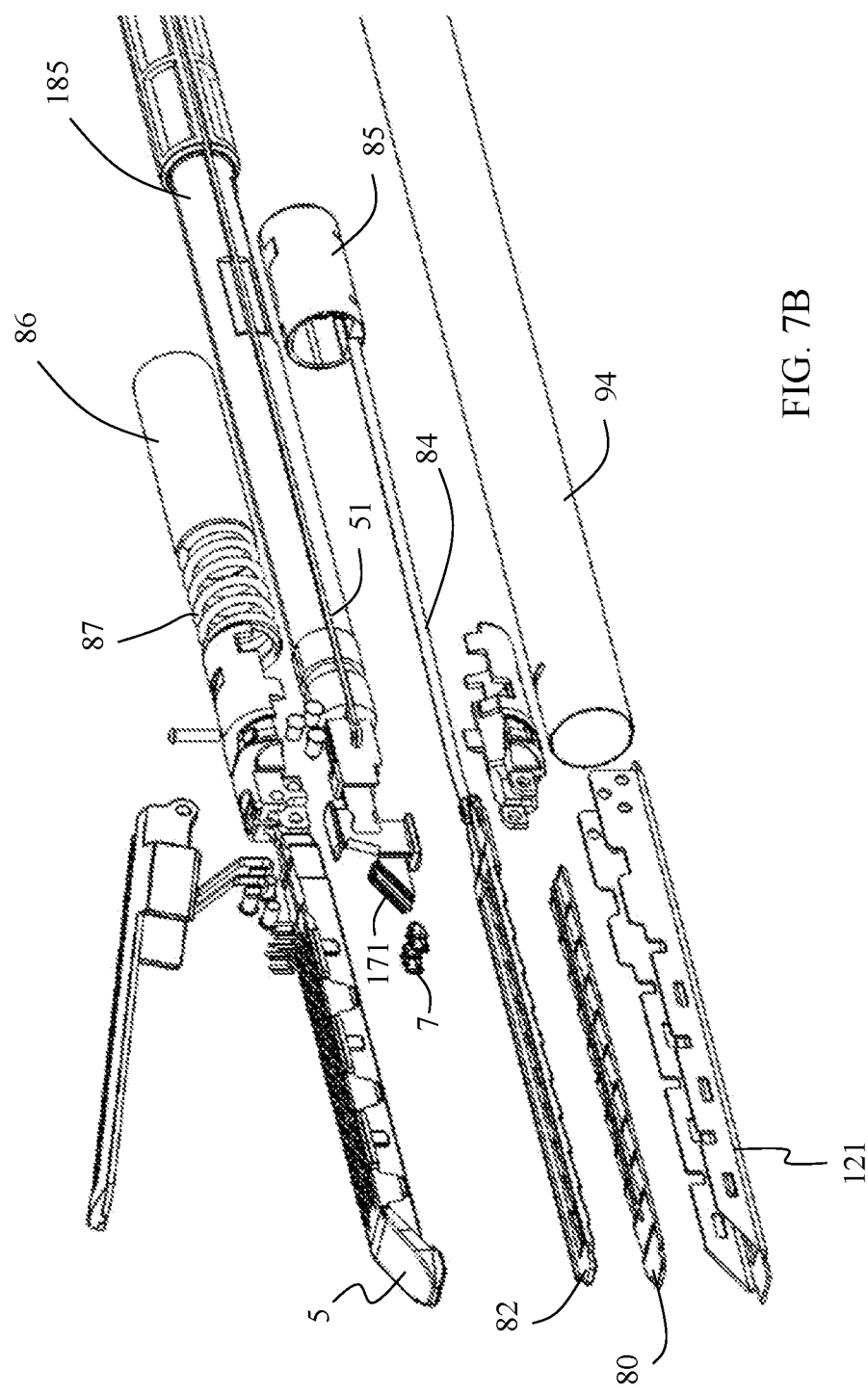
FIG. 7B is an exploded view of a staple and transector receptacle of a surgical stapler in accordance with various embodiments of the present invention.
Figure 10A:
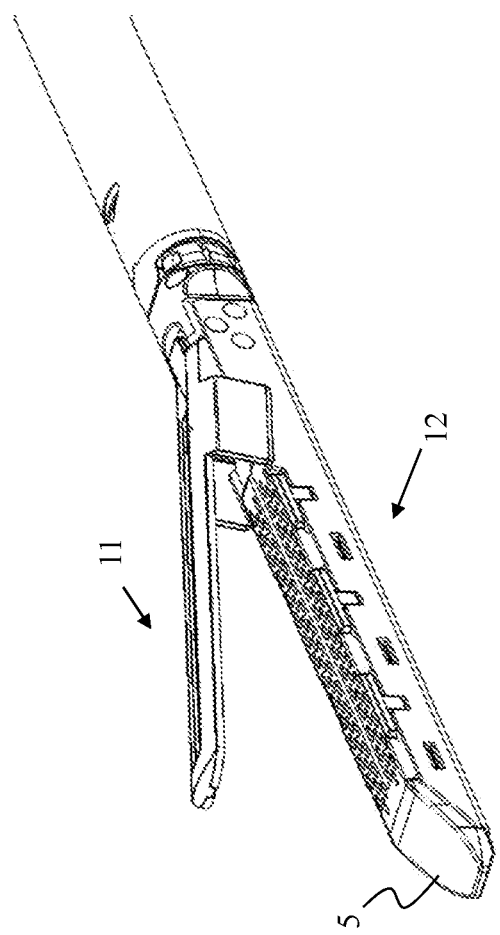
FIG. 10A is a perspective view of a staple and transector receptacle of a surgical stapler in accordance with various embodiments of the present invention.
Figure 10B:
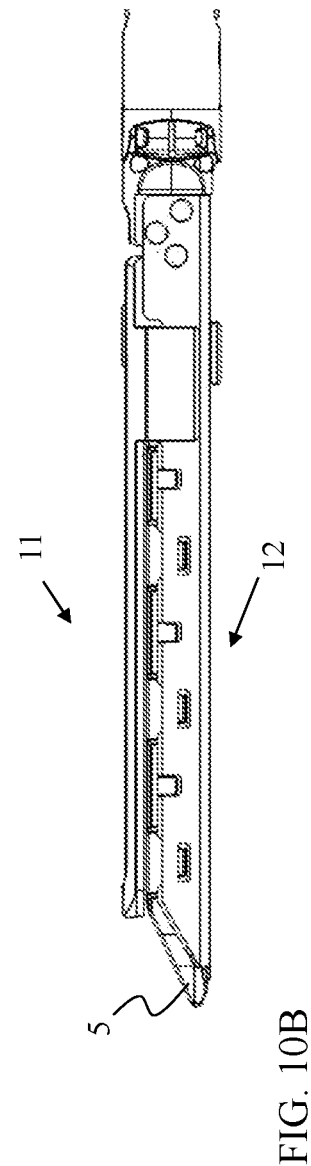
FIG. 10B is a perspective view of a staple and transector receptacle of a surgical stapler in accordance with various embodiments of the present invention.
Figure 11A:
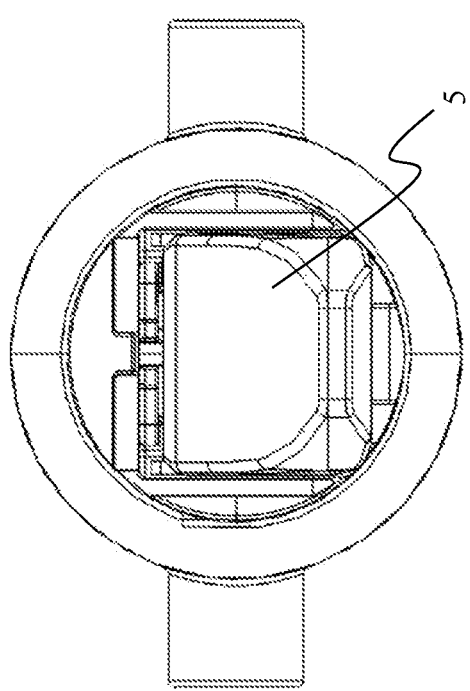
FIG. 11A is a front view of a staple and transector receptacle of a surgical stapler in accordance with various embodiments of the present invention.
Figure 11B:
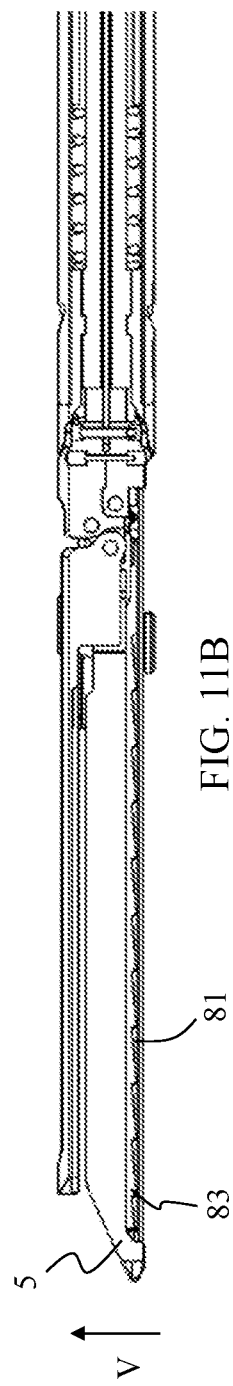
FIG. 11B is a side cross-sectional view of a staple and transector receptacle of a surgical stapler in accordance with various embodiments of the present invention.
Figures 16A, 16B:
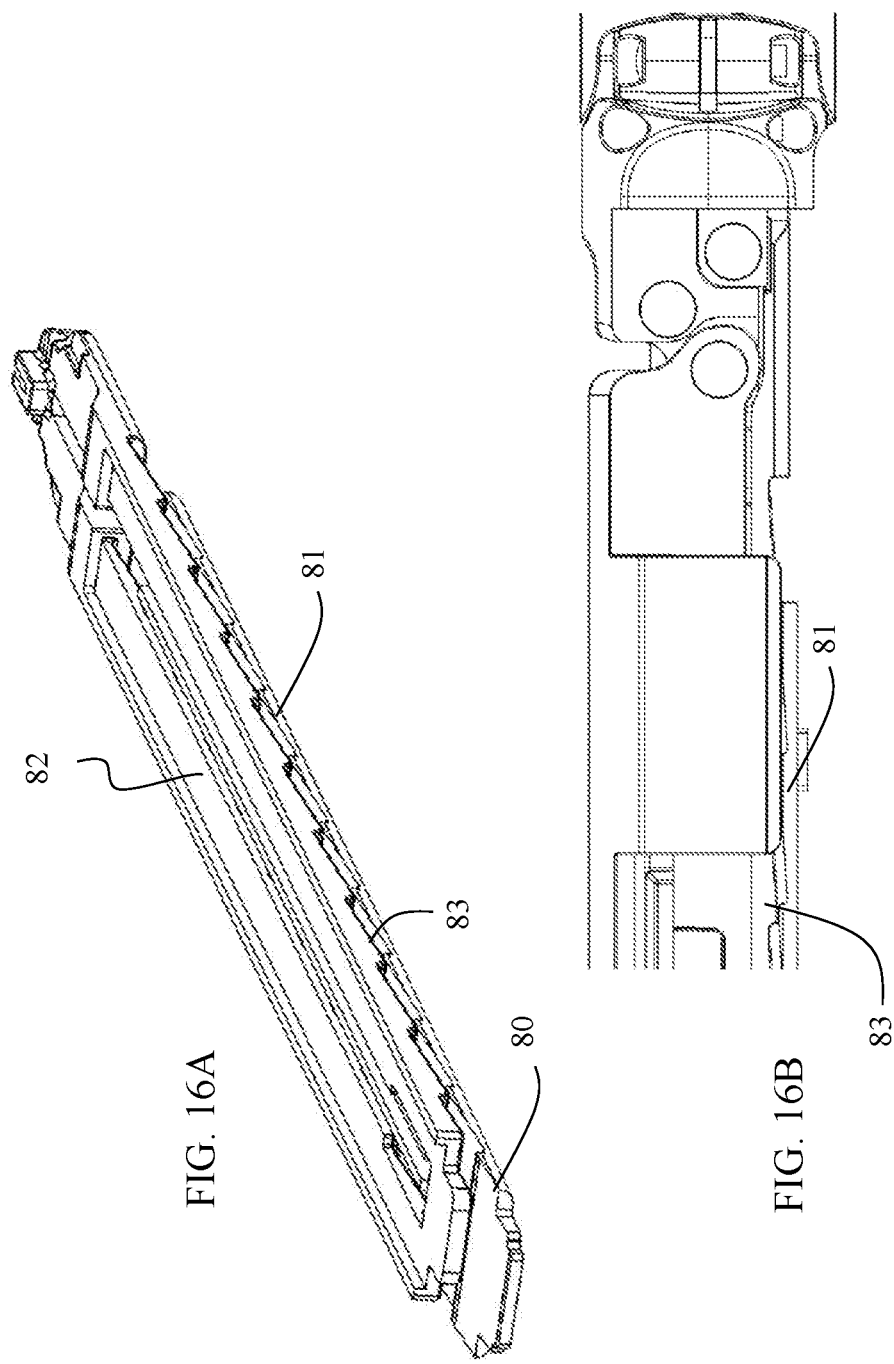
FIG. 16A is a perspective view of portions of a staple and transector receptacle of a surgical stapler in accordance with various embodiments of the present invention.
FIG. 16B is a side cross-sectional view of portions of a staple and transector receptacle of a surgical stapler in accordance with various embodiments of the present invention.

In accordance with various embodiments surgical staplers are provided. The stapler in various embodiments includes a one-way vertically adjustable staple cartridge. The stapler also includes one jaw to hold the staple cartridge and a second jaw to hold an anvil. The jaws and shaft are dimensioned to fit through a cannula delimiting at most an inner diameter of 12 mm. The shaft is positioned between the jaws and an actuator. The actuator allows a user, e.g., a surgeon, to manipulate a handle, lever, switch or other operationally accessible actuators to open and close the jaws to grasp tissue, articulate the jaws from side to side, fire the staples out the staple cartridge and into the grasped tissue and cut tissue between the jaws. The vertically adjustable staple cartridge is automatic utilizing no-user interaction and applies a vertical uniform compression force towards and on tissue against the anvil after the jaws are closed. In one embodiment, the vertically adjustable mechanism is only activated after the jaws are closed, the firing mechanism enabled and firing commenced without the ability to un-fire or stop firing. This prevents unwanted tissue compression or trauma.

The vertically adjustable mechanism drives the staple cartridge only vertically towards the anvil no side to side or wobbling is permitted. Additionally, in various embodiments, the staple cartridge is movable only towards the tissue and anvil and not away from the tissue or anvil. As such, once the vertically adjustable mechanism is activated, the stapler cartridge is movable in only one direction.

Referring to FIGS. 1-79, in accordance with various embodiments, a surgical stapler is provided. In the various illustrated embodiments, the surgical stapler includes an actuator 2 removably connected to a staple and transector receptacle (STR) 10. The STR includes an upper movable jaw 11 and a lower stationary jaw 12 at a distal end of an elongate shaft 14. The upper jaw 11 is configured to include an anvil 9 and the lower jaw is configured to include a staple cartridge 5. At a proximal end of the elongate shaft 14 is an actuator interface 15. The actuator interface connects and disconnects the STR 10 from the actuator 2. The actuator 2 includes a rotator 16 that when rotated by a user rotates the elongate shaft 14 and thus the jaws 11, 12. The actuator 2 also includes a trigger or movable handle 21 connected to a stationary handle or handle base 22. In one embodiment, the handle base includes two halves that mate together to form the handle base 22. The trigger 21, under specific conditions to be described in greater detail below, when manipulated by a user causes the closing and opening of jaws 11, 12, firing of staples, translating a blade and a vertical adjustment of a staple cartridge. In one embodiment, the upper and lower jaws both move relative to each other and in one embodiment the lower jaw moves while the upper jaw remains stationary.

The upper jaw 11 includes an anvil 9 for forming a plurality of staples 6 sequentially ejected from a staple cartridge 5. The upper jaw 11 is pivotably coupled to upper outer cover 91 that is connected to a lower outer cover 92. The upper jaw 11 includes jaw springs 93 biasing the upper jaw to an open or spaced condition. The lower outer cover 92 is connected to a retainer 121. The retainer 121 holds a rampway 80 affixed to the retainer and including a plurality of ramps 81. The retainer 121 also houses a movable cartridge platform or lift 82 including a plurality of ramps 83 that correspondingly mate with the plurality of ramps 81 of the rampway 80. The staple cartridge 5 sits upon the cartridge lift 82. When the cartridge lift 82 is moved longitudinally and proximally (e.g., as illustrated by arrow H), the ramps 83 of the cartridge lift 82 slide on the ramps 81 of the rampway 80 which moves the cartridge 5 vertically (e.g., as illustrated by arrow V) or in a direction traverse to (e.g., perpendicular to) the longitudinal axis 1 of the STR 10.

The staple cartridge 5 includes a plurality of staples 6 and a corresponding set of staple pushers 7 situated in a plurality of staple pockets. Through interaction of a set of fins 171 on a slider 17 with the staple pushers, the staples are fired or ejected from the staple cartridge 5. Staples within the cartridge 5 are thus fired through the longitudinal movement of the slider that interacts with staple pushers within staple pockets of the cartridge. Fired staples penetrate tissue clamped between the jaws 11, 12 and are formed against anvil pockets on the anvil 9. The slider 17 is operatively connected to an actuation beam 18. The actuation beam 18 includes a blade 19 and is connected to an actuation slide 180. In one embodiment, the actuation slide 180 includes a proximate actuation slide 181 coupled to a distal actuation slide 182. The distal actuation slide 182 is perpendicular to the proximate actuation slide 181 with both slides extending parallel to the longitudinal axis 1 of the STR 10. In the illustrated embodiment, the intersection of the proximal and distal actuation slides in cross-section forms a cross.

The actuation beam 18 has an upper guide or roof 183 that is configured to move within a longitudinal slot or channel in the upper jaw 11 and a lower guide or floor 184 that is configured to move within a longitudinal slot or channel in the lower jaw 12. Likewise, the staple cartridge 5, cartridge lift 82 and the retainer 121 includes a longitudinal channel through which the lower guide 184 moves therethrough. The upper and lower guides of the actuation beam ensure parallel jaw alignment and compression of the closing of the jaws 11, 12.

The actuation slides 181, 182 are surrounded by an actuation cover tube 185 that includes an opening 186 through which a STR reuse lockout 41 is biased by a leaf spring 42 through the opening 186 in the actuation cover tube 185. The actuation cover tube includes slots or guides to ensure alignment and translational movement of the actuation slides 181, 182.

An outer tube 94 surrounds the actuation cover tube 185 and is connected to actuator interface 15 with a pair of opposing protrusions on opposing sides of the interface for a removable connection to the STR coupler 151. A coupler spring 152 is positioned between the rotator and STR coupler to bias the rotator in the distal direction such that movement of the rotator in the proximal direction compresses the spring and exposes the coupler 151 and the connection thereto for removably connecting with actuator interface 15. Extending parallel to the actuation cover tube 185 and the actuation slides 181, 182 is an articulation beam 51. The articulation beam 51 includes a proximal end that is connected to the upper and lower outer covers 91, 92 and in one embodiment sits and rides within slots of the actuation cover tube 185.

Figure 17A:
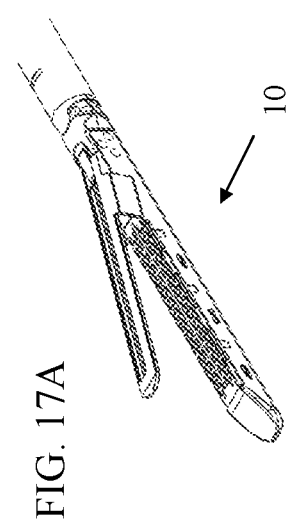
FIG. 17A is a perspective view of a distal end of a staple and transector receptacle of a surgical stapler in accordance with various embodiments of the present invention.
Figure 17B:
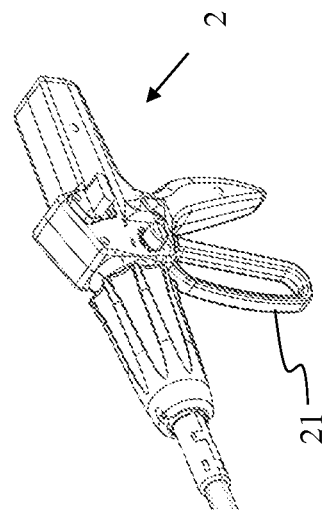
FIG. 17B is a perspective view of a proximal end of a staple and transector receptacle of a surgical stapler in accordance with various embodiments of the present invention.
Figure 17C:
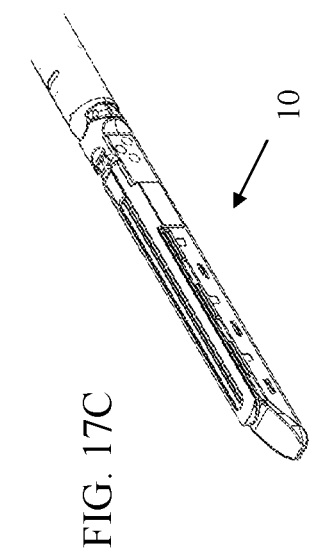
FIG. 17C is a perspective view of a distal end of a staple and transector receptacle of a surgical stapler in accordance with various embodiments of the present invention.
Figure 17D:
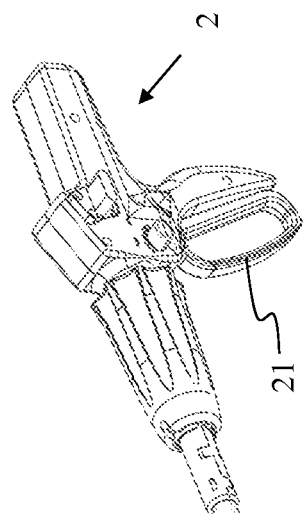
FIG. 17D is a perspective view of a proximal end of a staple and transector receptacle of a surgical stapler in accordance with various embodiments of the present invention.
Figure 18:
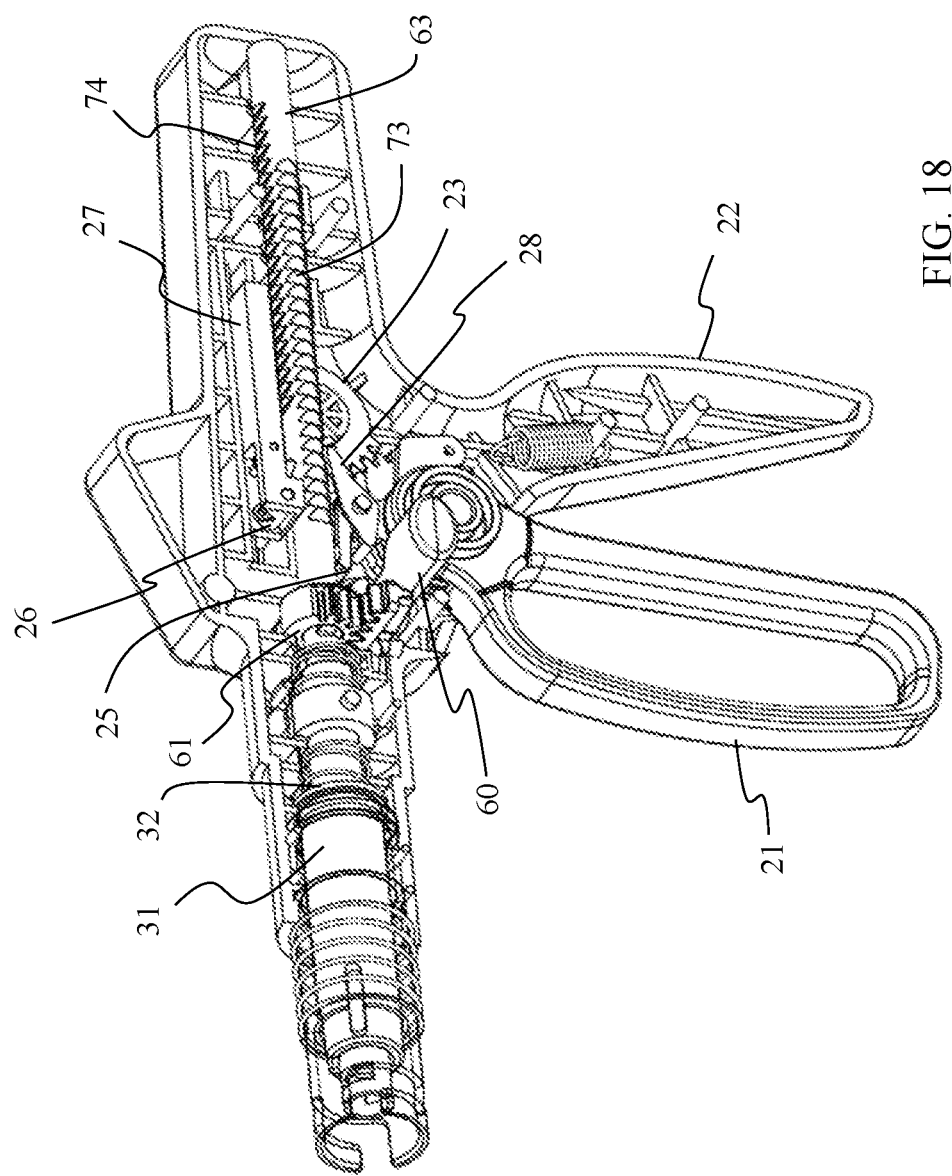
FIG. 18 is a perspective view of an actuator of a staple and transector receptacle of a surgical stapler in accordance with various embodiments of the present invention.
Figure 19:
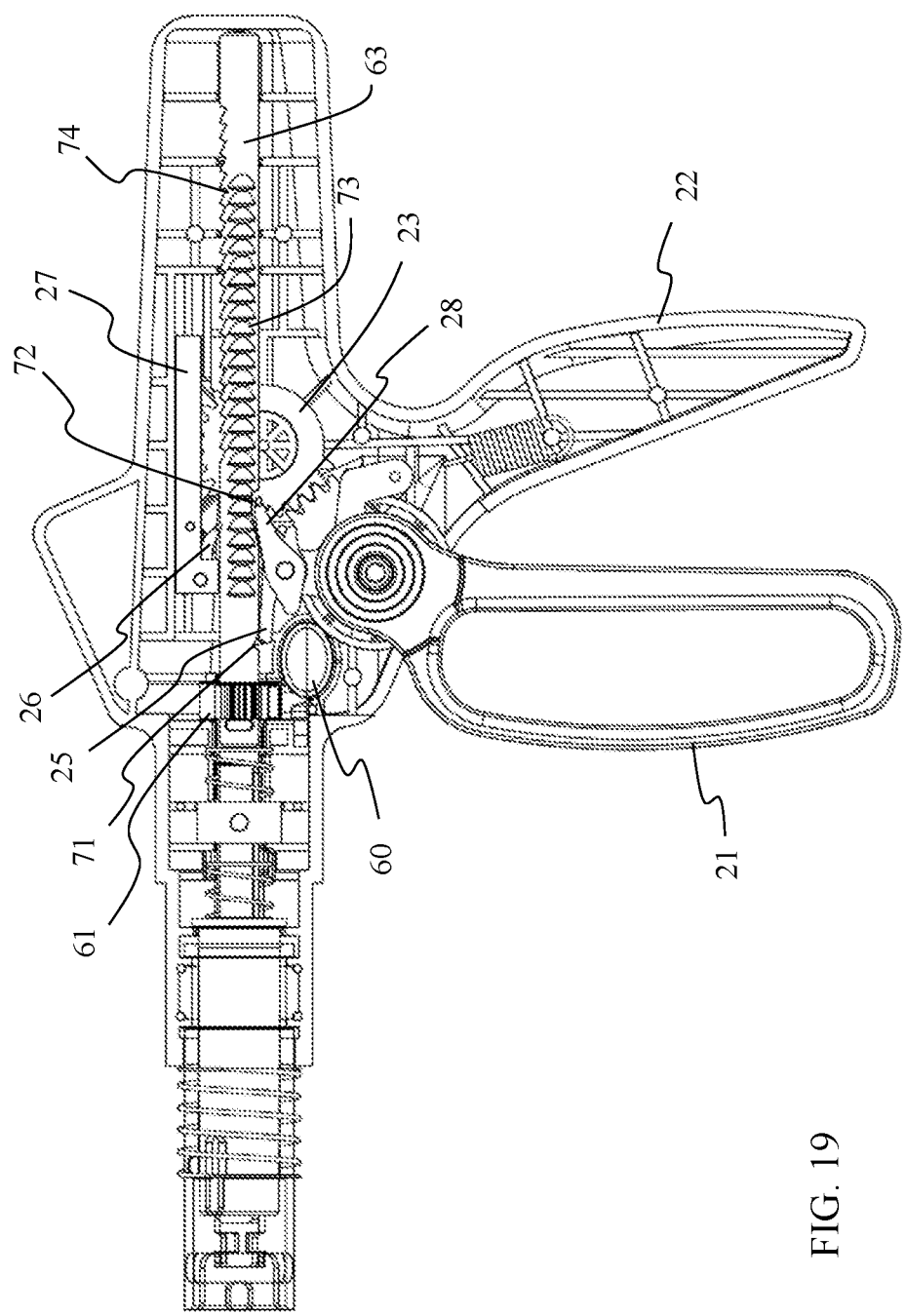
FIG. 19 is a side view of an actuator of a staple and transector receptacle of a surgical stapler in accordance with various embodiments of the present invention.
Figure 20:
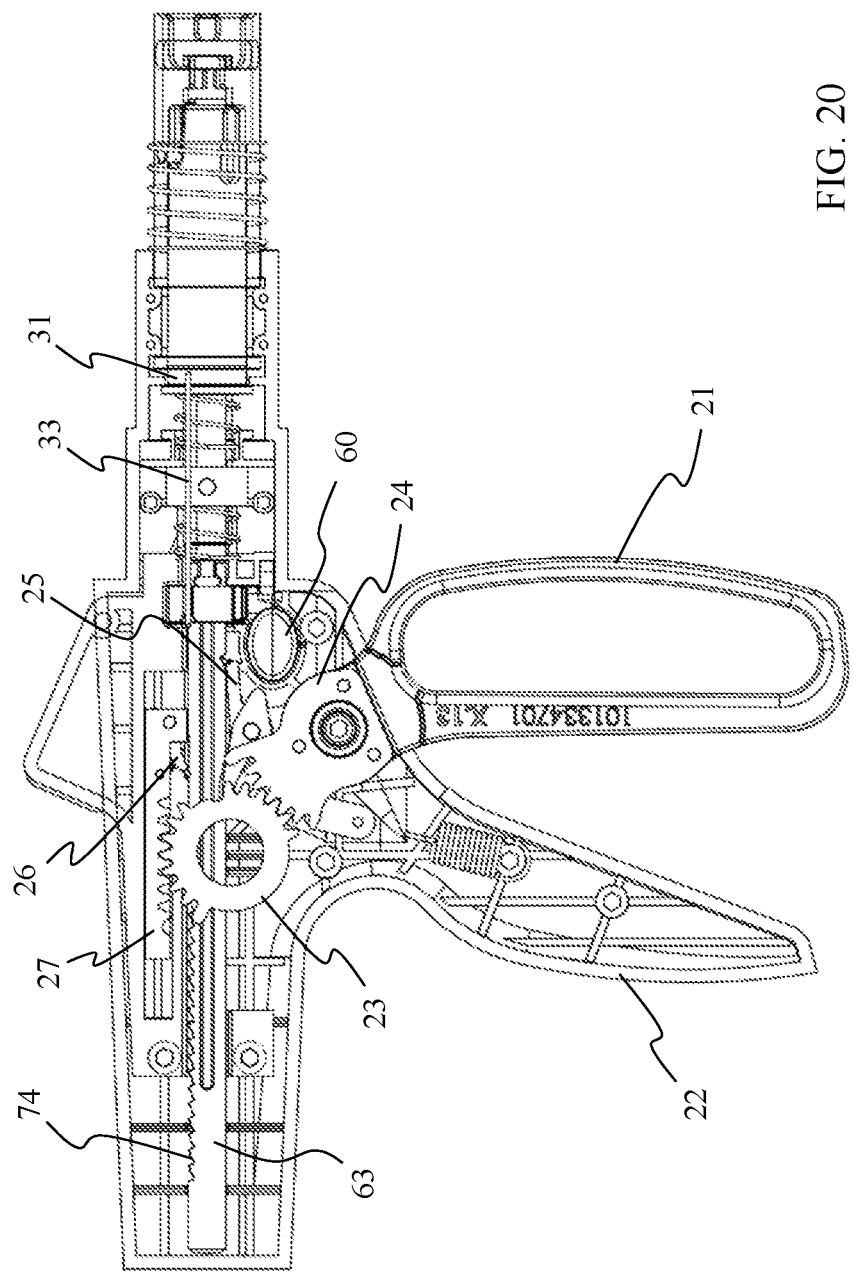
FIG. 20 is a side view of an actuator of a staple and transector receptacle of a surgical stapler in accordance with various embodiments of the present invention.
Figure 21:
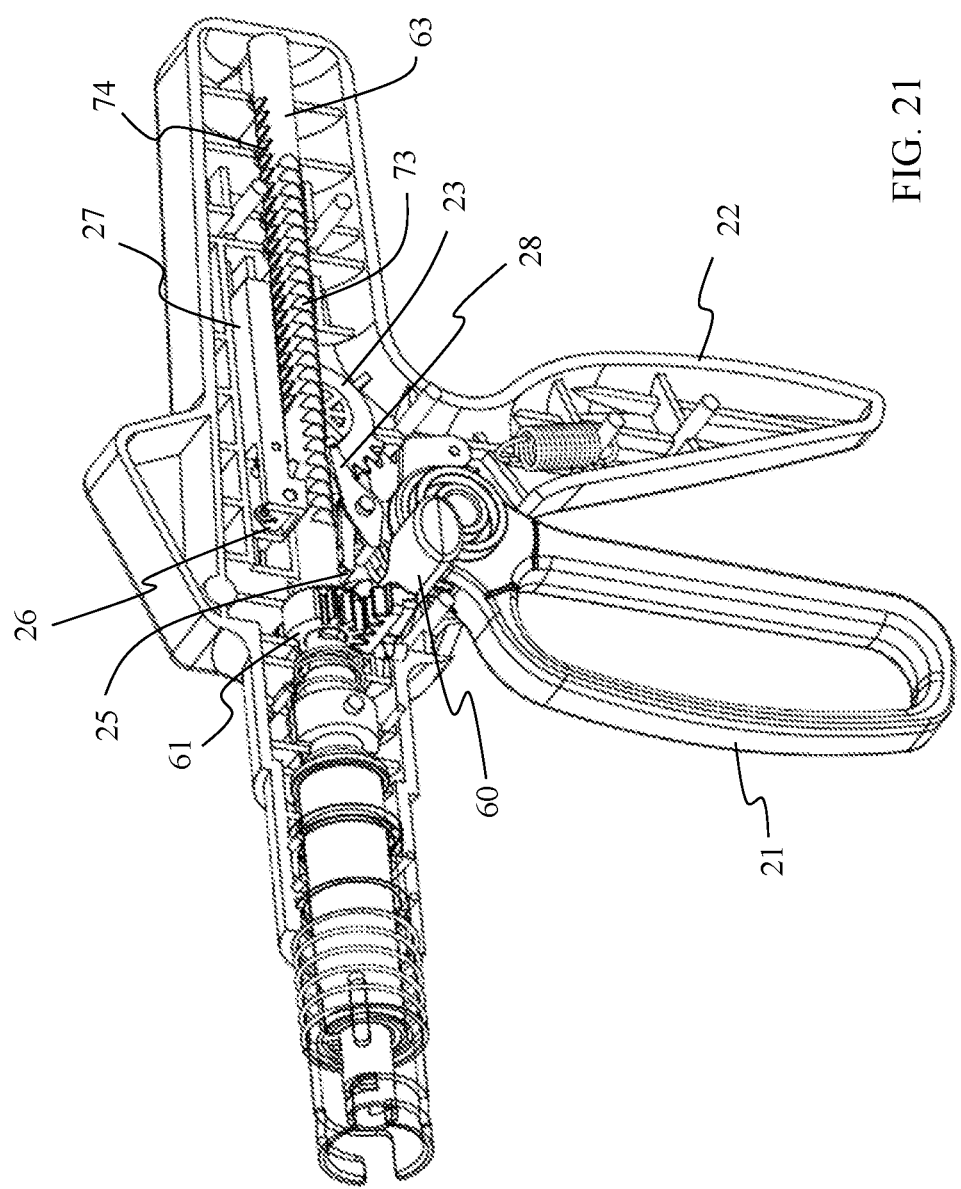
FIG. 21 is a perspective view of an actuator of a staple and transector receptacle of a surgical stapler in accordance with various embodiments of the present invention.
Figure 22:
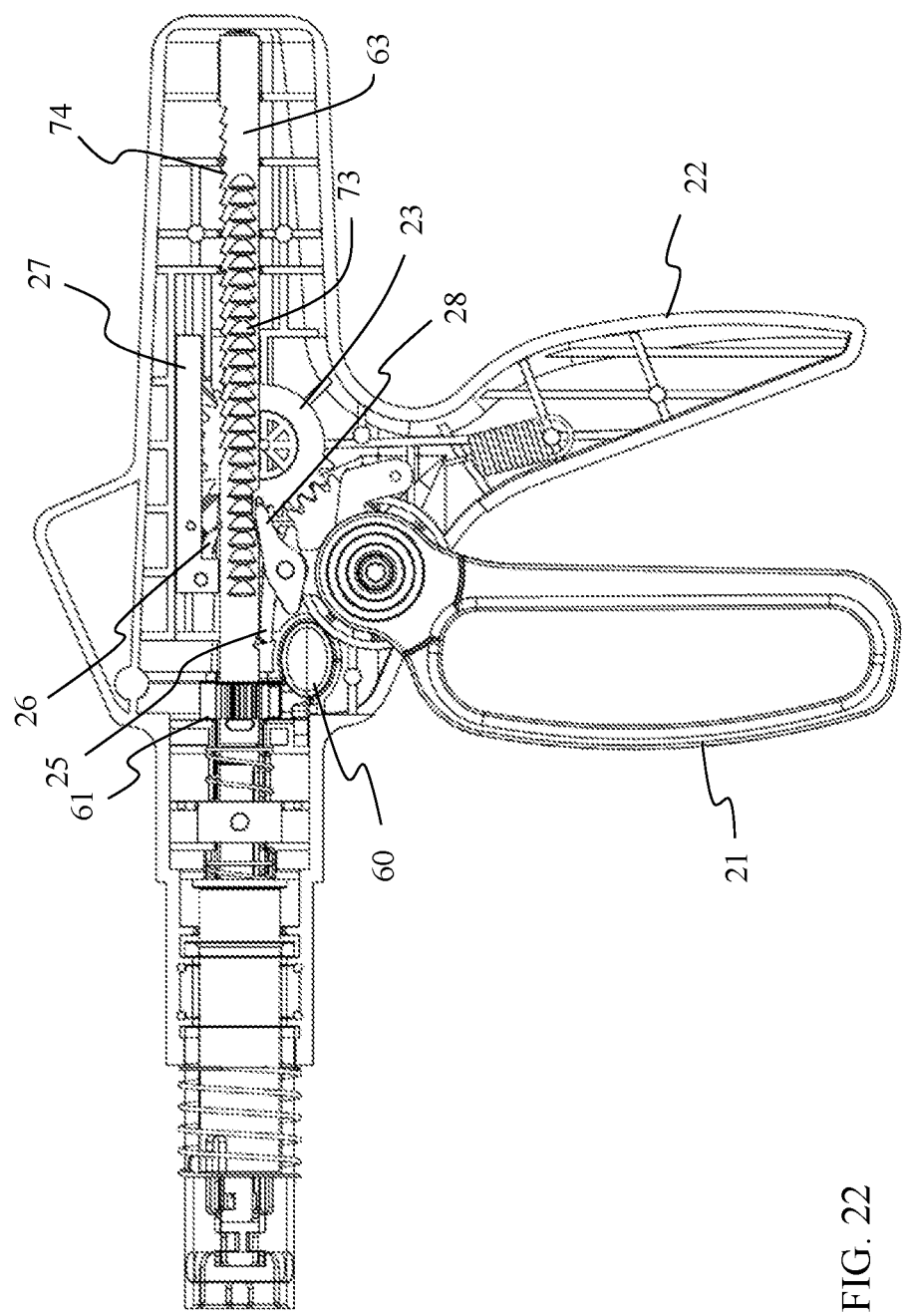
FIG. 22 is a side view of an actuator of a staple and transector receptacle of a surgical stapler in accordance with various embodiments of the present invention.
Figure 23:
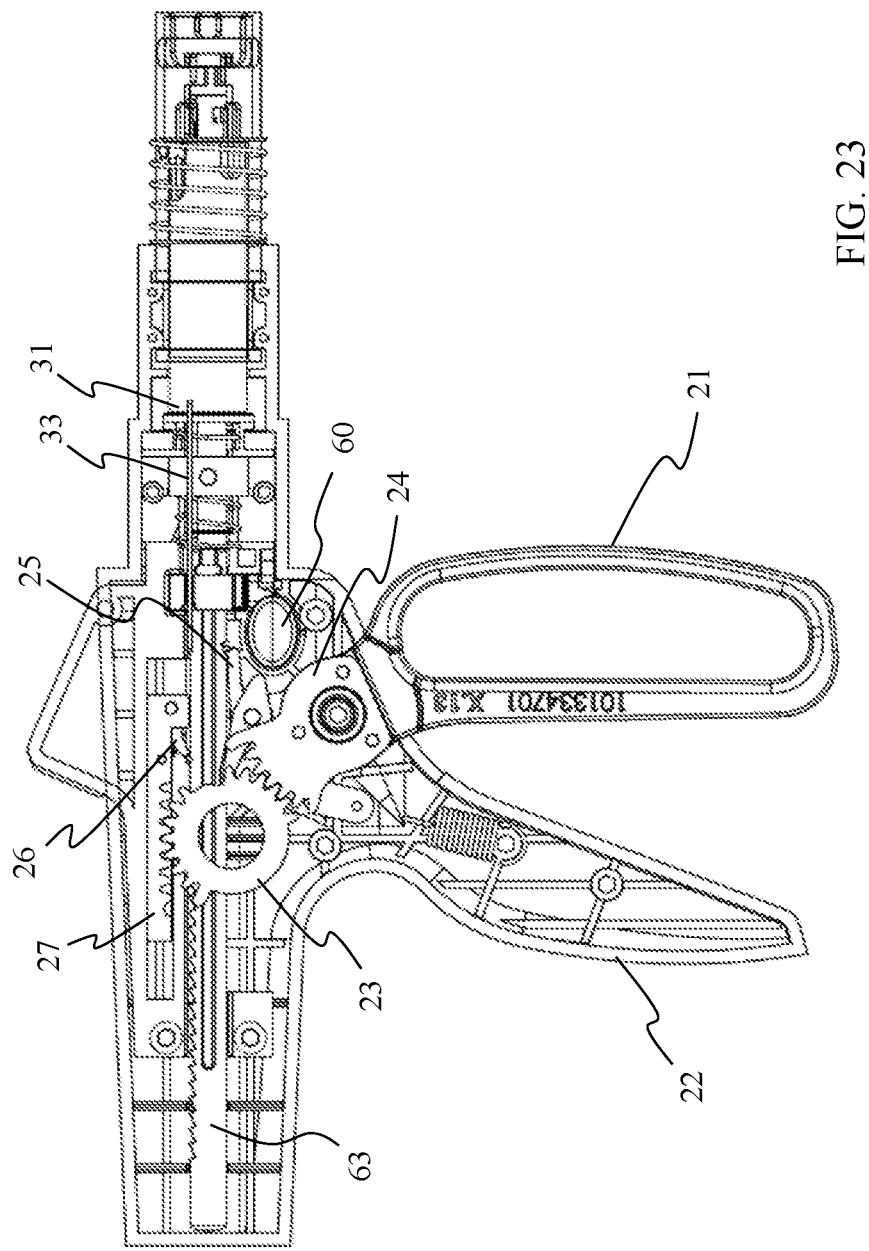
FIG. 23 is a side view of an actuator of a staple and transector receptacle of a surgical stapler in accordance with various embodiments of the present invention.
Figure 24:
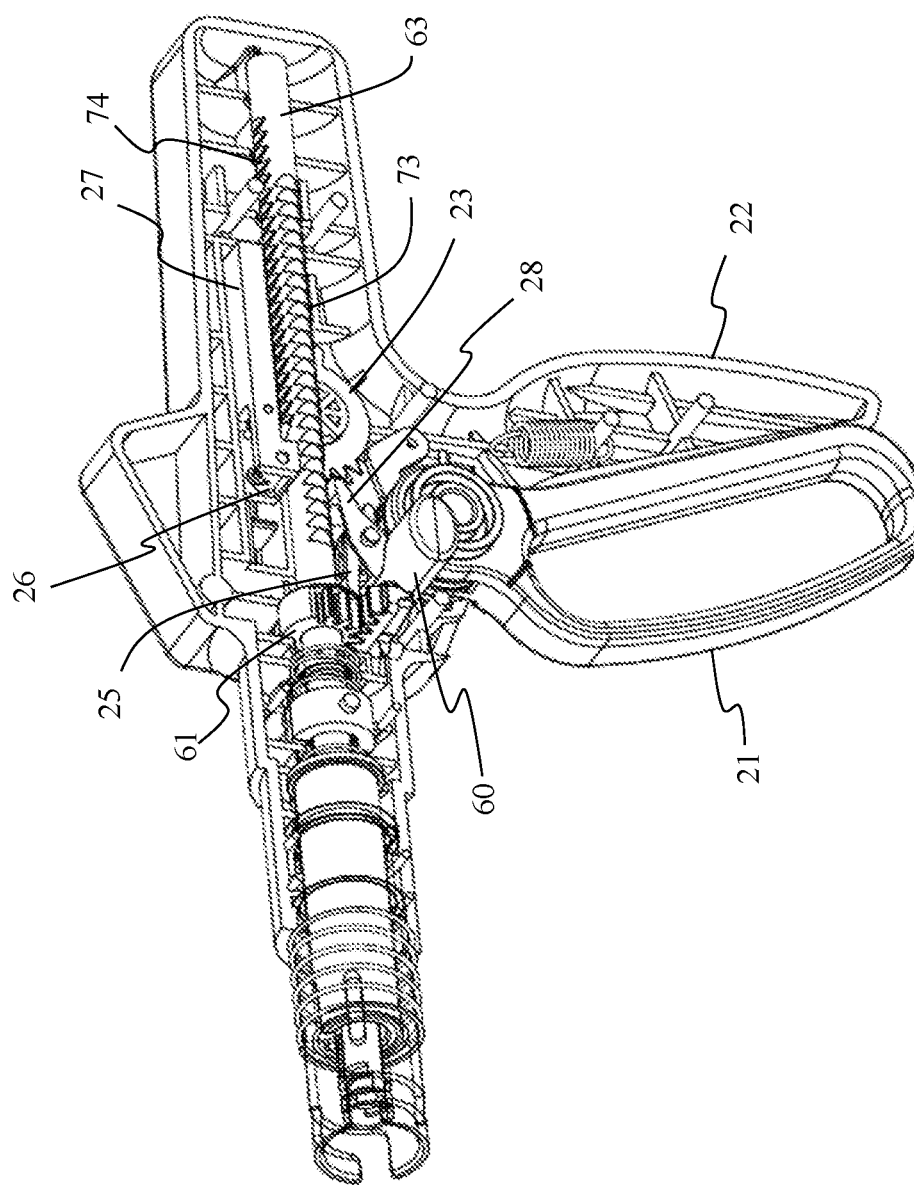
FIG. 24 is a perspective view of an actuator of a staple and transector receptacle of a surgical stapler in accordance with various embodiments of the present invention.
Figure 25:
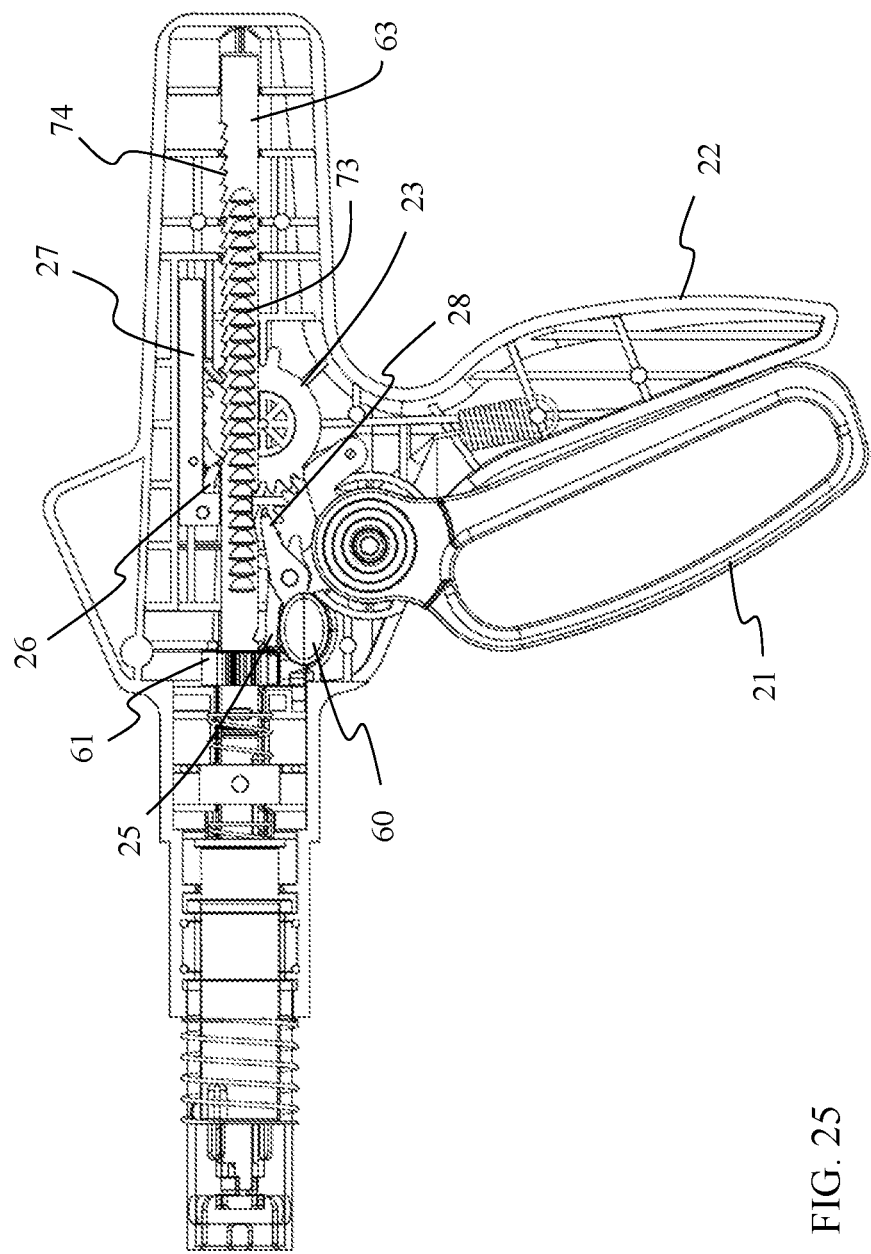
FIG. 25 is a side view of an actuator of a staple and transector receptacle of a surgical stapler in accordance with various embodiments of the present invention.
Figure 26:
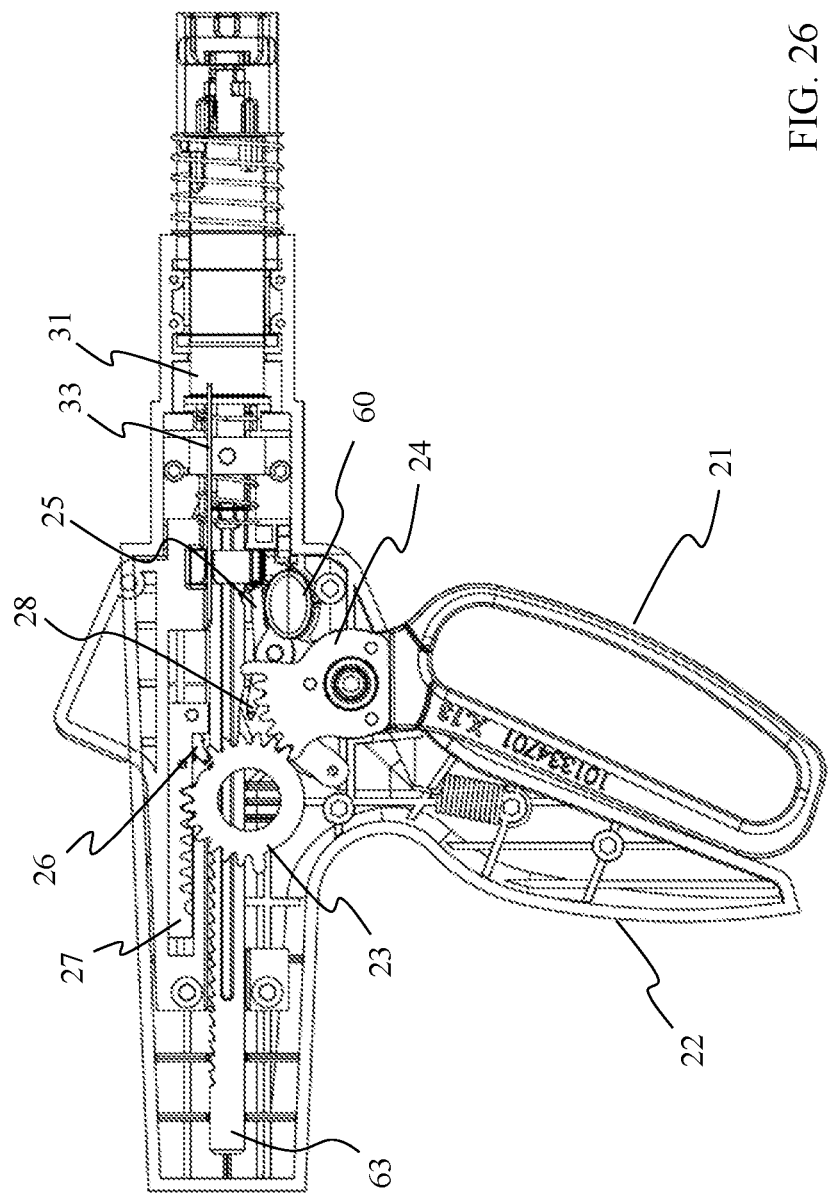
FIG. 26 is a side view of an actuator of a staple and transector receptacle of a surgical stapler in accordance with various embodiments of the present invention.
Figure 27:
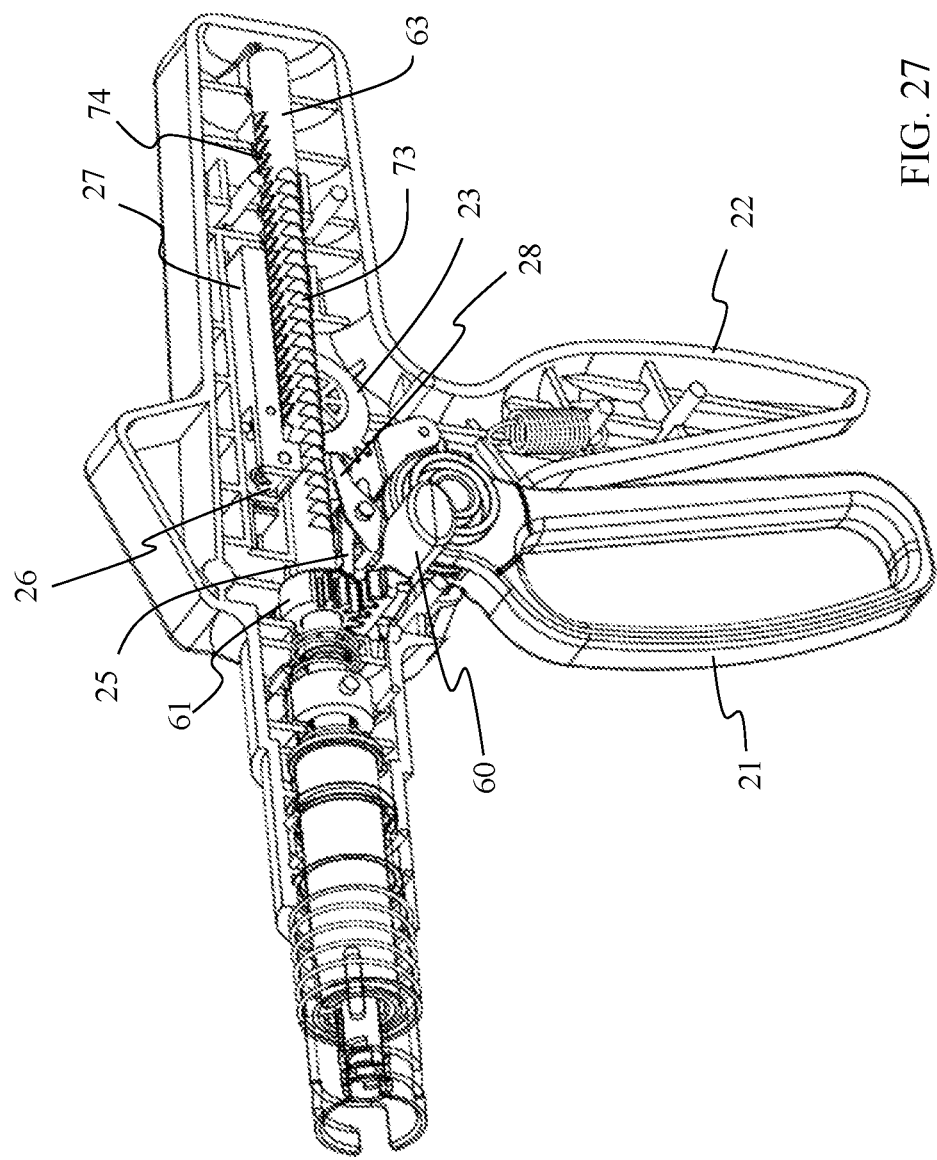
FIG. 27 is a perspective view of an actuator of a staple and transector receptacle of a surgical stapler in accordance with various embodiments of the present invention.
Figure 28:
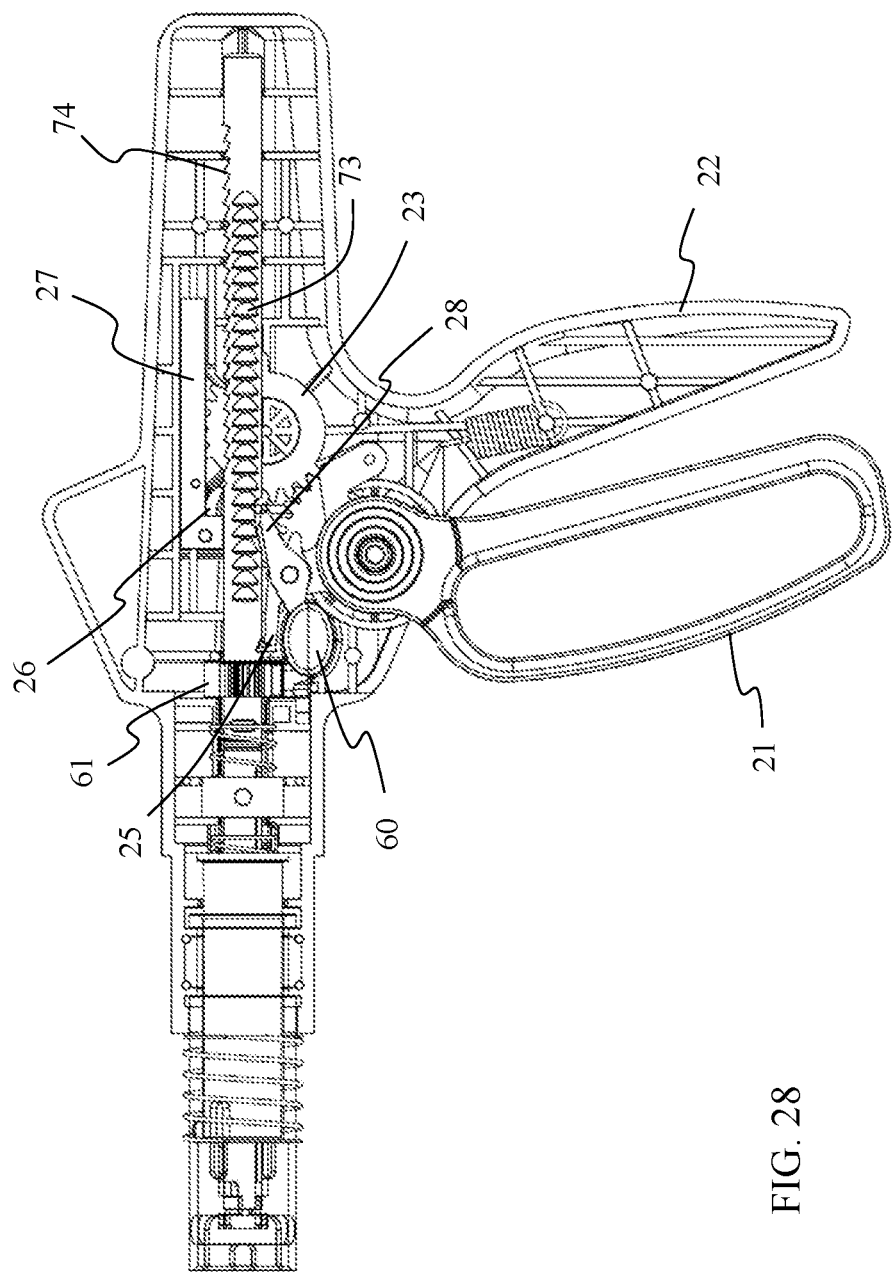
FIG. 28 is a side view of an actuator of a staple and transector receptacle of a surgical stapler in accordance with various embodiments of the present invention.
Figure 29:
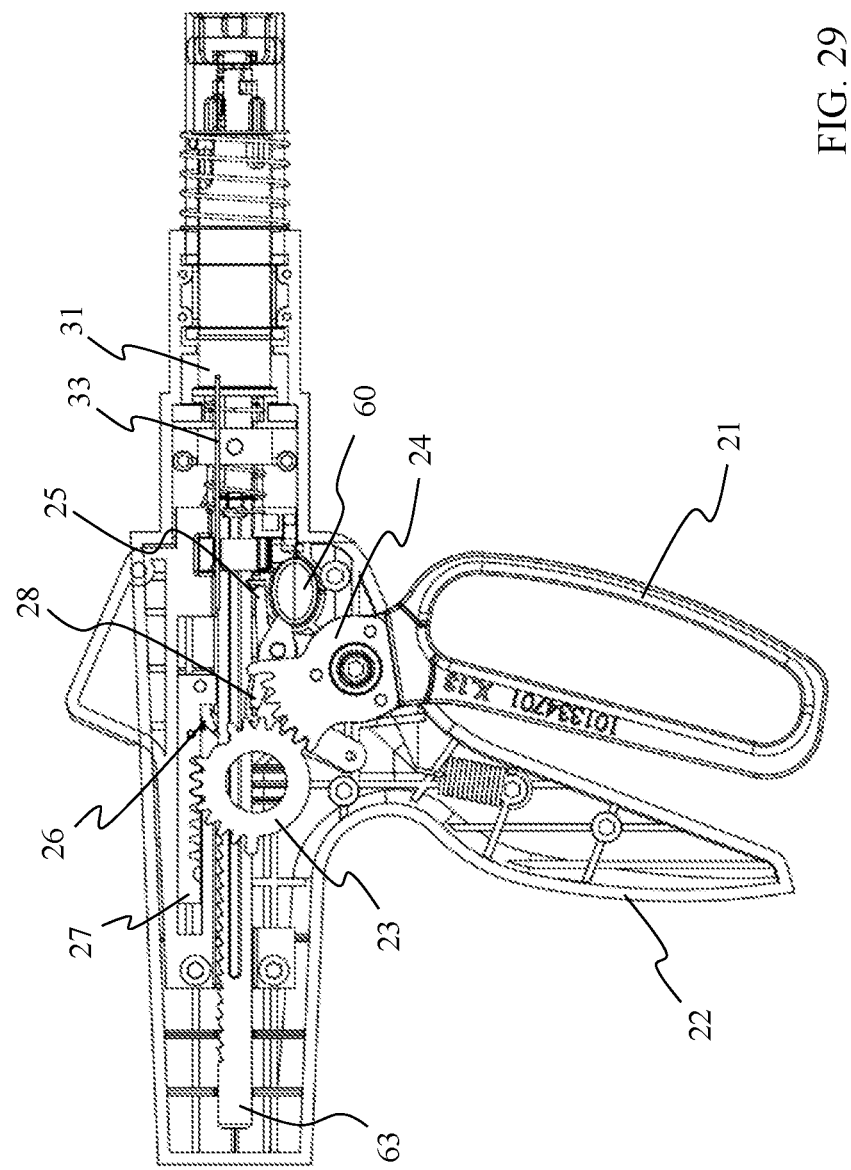
FIG. 29 is a side view of an actuator of a staple and transector receptacle of a surgical stapler in accordance with various embodiments of the present invention.

The actuator 2 is operably coupled to the removably coupled STR 10 and actuates the jaws 11, 12 from an open-close configuration to a one-way automatic self-adjusting stapling or forward configuration to a reverse configuration through the driving or manipulation of the actuation beam 18 forward or backwards (distally or proximally). FIGS. 17-46 in particular illustrate the actuator 2 including the inner workings thereto in various states of operation in accordance with various embodiments. For example, FIGS. 17A-B illustrate the stapler with its jaws in an open or initial configuration and FIGS. 17C-D illustrate the stapler with its jaws in a closed yet unfired or non-firing configuration.

In an initial position of the stapler, the actuation beam 18 is positioned at the most proximal position of its travel and the jaws 11, 12 are in an open configuration or position. The actuation beam engages the upper jaw 11 upon translation of the actuation beam distally along the longitudinal axis 1 of the elongate shaft 14. Translation of the actuation beam distally from the initial position a first predefined longitudinal distance (e.g., 0.225") can actuate the jaws from an open position to a closed position. With the jaws in the closed configuration, the actuation beam can be returned proximally, as influenced by the jaw springs biasing the jaws open, traveling the same first distance to return the jaws to the open position. The trigger 21 of the actuator 2 is operatively coupled to the actuation beam such that as the trigger is squeezed, the jaws close, and as the trigger is pushed open or in one embodiment released, the jaws open. In one embodiment, the trigger 21 is connected to a forward distal pivot pawl 25 with a tip or tooth engageable with a groove or cut-out 71 in an actuation rod 62 operatively connected to the actuation beam 18. The engagement of the forward distal pivot pawl with the groove 71 in the actuation rod assists in moving the actuation rod in the distal direction as the trigger is pivoted towards the handle base. Such movement of the actuation rod in the distal direction moves the actuation beam 18 in the distal direction causing the jaws to close.

Likewise, in one embodiment, the trigger 21 is connected to a forward proximal pivot pawl 28 with a tip or tooth engageable with a groove or cut-out 72 in an actuation rod 62 operatively connected to the actuation beam 18. The engagement of the forward proximal pivot pawl with the groove 72 in the actuation rod assists in moving the actuation rod in the proximal direction as the trigger is pivoted away from the handle base or released. Such movement of the actuation rod in the proximal direction allows the jaws to open. The trigger 21 is biased by a spring causing the trigger to be biased back to an initial or open position with the trigger pivoted away from the handle base. The forward distal pivot pawl 25 and the forward proximal pivot pawl 28 are pivotable connected to the trigger 21 and in one embodiment form or resemble a "V" with the distal pivot pawl 25 extending in a direction that is opposite to that of the proximal pivot pawl 28. The groove or cut-out 71 operatively engageable with the distal pivot pawl 25 is near the distal end of the actuation rod and is distal from the groove 72 that is operatively engageable with the proximal pivot pawl 28. The open-close operation can be repeated multiple times as desired by the user to for example grasp or dissect tissue for a given surgical procedure.

In various embodiments, a STR recognition barrel 31 prevents activation or movement of the firing operation unless a STR 10 is attached to the actuator 2. Movement or articulation of the trigger 21 of the actuator 2 however is not prevented. Allowing movement of the actuator can assist in packaging and testing of the actuator. Additionally, this allows the attachment of other front-end actuation units that may require grasping and/or articulation with or without the ability or use for firing staples and thereby increasing the versatility of the actuator 2. In various embodiments, attaching a STR moves the recognition barrel 31 proximally which in turn compresses a STR recognition barrel spring 32 coupled to the recognition barrel. The spring 32 biases the recognition barrel distally and in one embodiment is coupled and captured between the outer surface of an articulation barrel 55 and the inner surface of the recognition barrel surrounding the spring 32. The recognition barrel, spring and articulation barrel are coaxially aligned. Movement of the recognition barrel moves a fire connector arm 33 connected to the barrel. In one embodiment, the connector arm 33 has a distal end affixed to a proximal end of the recognition barrel with a notch in the distal end of the connector arm 33 engaged with a peripheral flange around the proximal end of the recognition barrel. The proximal end of the connector arm 33 has a flange that is slidably coupled to an arming hub 61 through a notch or slot disposed in the arming hub. With the flange of the connector arm 33 disposed in the slot of the arming hub 61, rotational movement of the arming hub 61 is prevented. As will be described in greater detail below, rotational movement of the arming hub 61 rotates an actuation rod 62 allowing the interaction of the rod and trigger to fire the staples or open/close the jaws.

The arming hub 61 is also connected to a firing button 60 that allows a user to set the stapler in a firing mode or a reverse mode with each activation of the button rotating the rod into the respective operational position for the corresponding operation. As such, the connector arm 33 disposed in the slot of the arming hub 61 prevents rotation movement of the arming hub that also prevents activation of the fire button and thus prevents changing of the operation of the stapler. As a STR is attached to the actuator, full operation of the handle assembly is restored or allowed to proceed. In one embodiment, a bifurcated actuation rod, e.g., a proximal actuation rod 63 and a distal actuation rod 64, allows rotational movement by the user via the rotator 16 without effecting operation of the stapler.

The distal end of the actuation rod 62 is removably coupled to the actuation slide of the STR. In one embodiment, the distal end of the actuation rod includes a slot configuration arranged to receive corresponding mating flanges on the actuation slide to twist and lock into a removable mating connection of the actuation rod to the actuation slide 180. As such, translation movement of the actuation rod also translates the actuation slide.

Once the jaws 11, 12 are fully closed by squeezing the trigger, the user can push the forward or fire button 60 on the actuator to change the mode of the handle to the forward configuration where the firing and self-adjusting mechanisms are activated.

As previously described, in one embodiment, the fire button 60 cannot be actuated until a STR is attached. In one embodiment, the fire button 60 also cannot be actuated until the actuation rod has traveled the predefined first distance distally. In accordance with various embodiments and as shown for example in FIGS. 27-29, once trigger 21 is released with the STR attached and the jaws fully closed, the jaws cannot be opened again until the staples are fired.

Once in the fire activation configuration, actuation of the trigger drives the actuation beam distally (i.e., only in one direction). In one embodiment, the first squeeze of the trigger also activates the self-adjusting height mechanism to resize the gap between the jaws. In one embodiment, the cartridge lift 82 in the lower jaw 12 will activate causing the cartridge to lift up or move only vertically and self-adjust to the tissue in the jaws. In one embodiment, at this time, an STR reuse lock 41 will also be activated. This STR reuse lock 41 ensures that the STR is only placed into the fire mode once, to prevent the user from inadvertently attempting to fire a previously used STR. Once the STR returns to the open-closed or initial position, the STR reuse lock 41 prevents the STR from firing again. Further actuation of the trigger will drive the actuation beam further forward sequentially ejecting staples and transecting the tissue grasped between the closed jaws.

In one embodiment, the slider 17 has one or more inclined fins 171 and is movable longitudinally to sequentially contact staple pushers 7 to eject the staples 6 in the staple cartridge 5. An actuation beam 18 movable longitudinally moves the slider distally and longitudinally. The slider in one embodiment is not connected and does not include keys, hooks or cavities to attach to the actuation beam. As such, the slider can only move longitudinally distally and is not able to return or move back or towards its proximal or initial position by movement of the actuation beam. The actuation beam 18 however can move back or towards its proximal or initial position. As such, in one embodiment, this allows the pushers 7 to fall back within the staple cartridge after being partially ejected or moved vertically by the longitudinal movement of the slider. This movement back into the cartridge reduces potential trauma to tissue, potential sticking to the staple or tissue and thus an overall smoother surface of the staple cartridge for removal of the tissue from between the jaws.

Additionally, the simultaneous allowance or lack of restriction of the actuation beam to move back or towards its proximal or initial position and then back provides further cutting of tissue or passes to cut tissue if desired or needed in such embodiments in which a cutting blade 19 is incorporated or attached to actuation beam 18. The actuation beam includes an upstanding edge with top and bottom perpendicular edges forming or incorporating the upper guide 183 and the lower guide 184. The upstanding edge travels within a longitudinal slot or channel extending through the staple cartridge and between the staple and staple pushers. The cutting blade is incorporated or attached to the upstanding edge of the actuation beam to cut tissue between jaws. The blade and upstanding edge of the actuation beam in one embodiment thus travels through a longitudinal channel within the staple cartridge, the anvil or both. The top and bottom perpendicular edges ride along outer surfaces of the jaws and ensure a fixed gap height, i.e., the distance between the top and bottom edges, and localized and compressive forces against the tissue. The top perpendicular edge or upper guide compresses the anvil and tissue vertically down towards and against the staple cartridge and the other jaw and the bottom perpendicular edge or lower guide compresses the staple cartridge and tissue vertically up towards and against the anvil and opposing jaw. The compression forces are localized to where the edges are positioned on the outer surfaces of the jaw during the actuation or firing stroke of the actuation beam.

Figure 30:
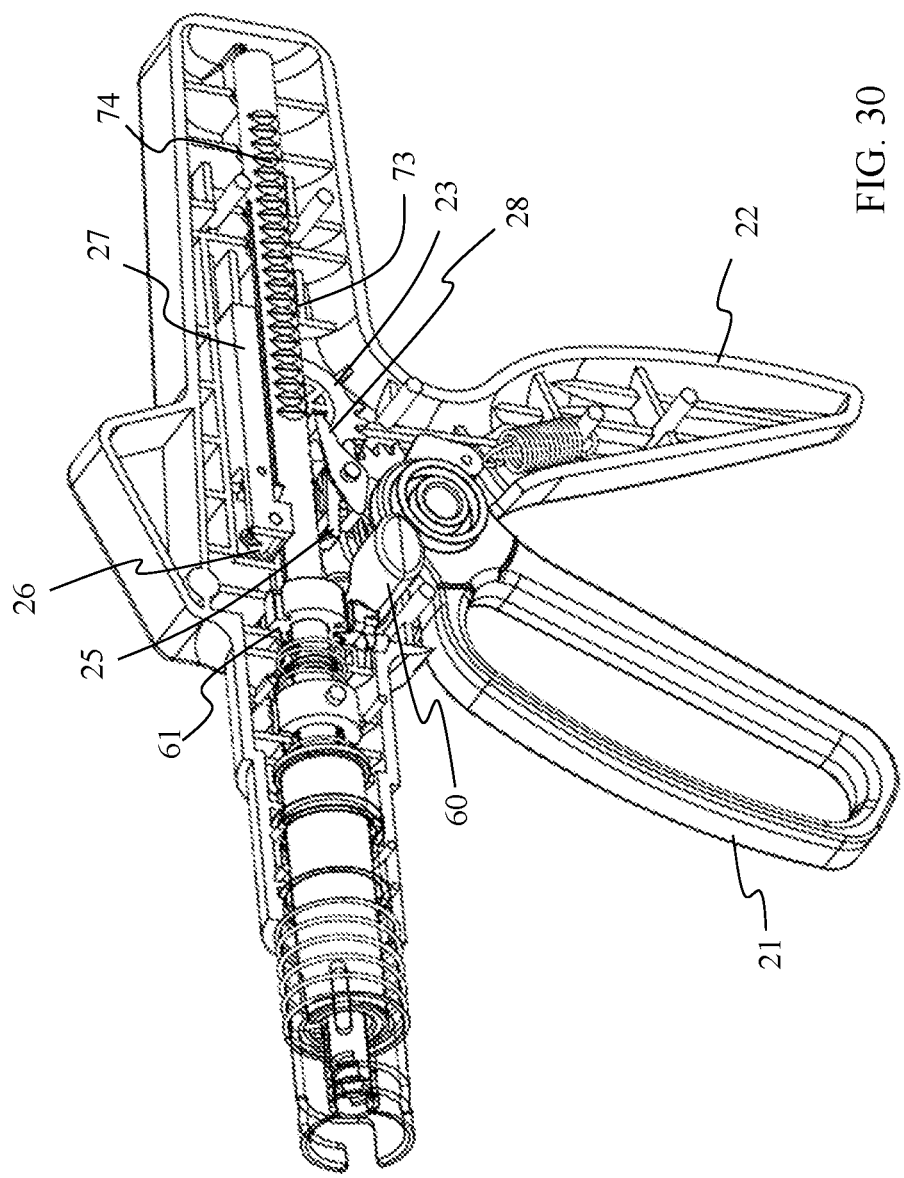
FIG. 30 is a perspective view of an actuator of a staple and transector receptacle of a surgical stapler in accordance with various embodiments of the present invention.
Figure 31:
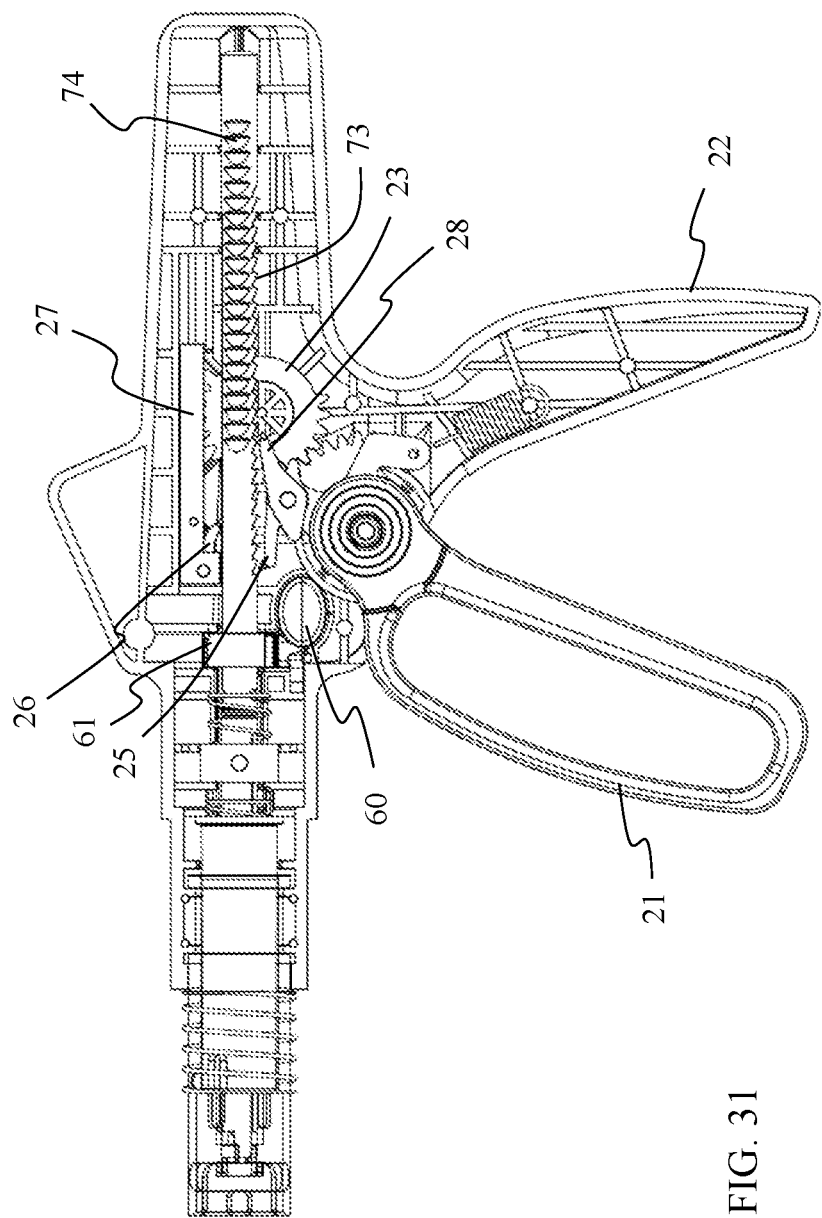
FIG. 31 is a side view of an actuator of a staple and transector receptacle of a surgical stapler in accordance with various embodiments of the present invention.
Figure 32:
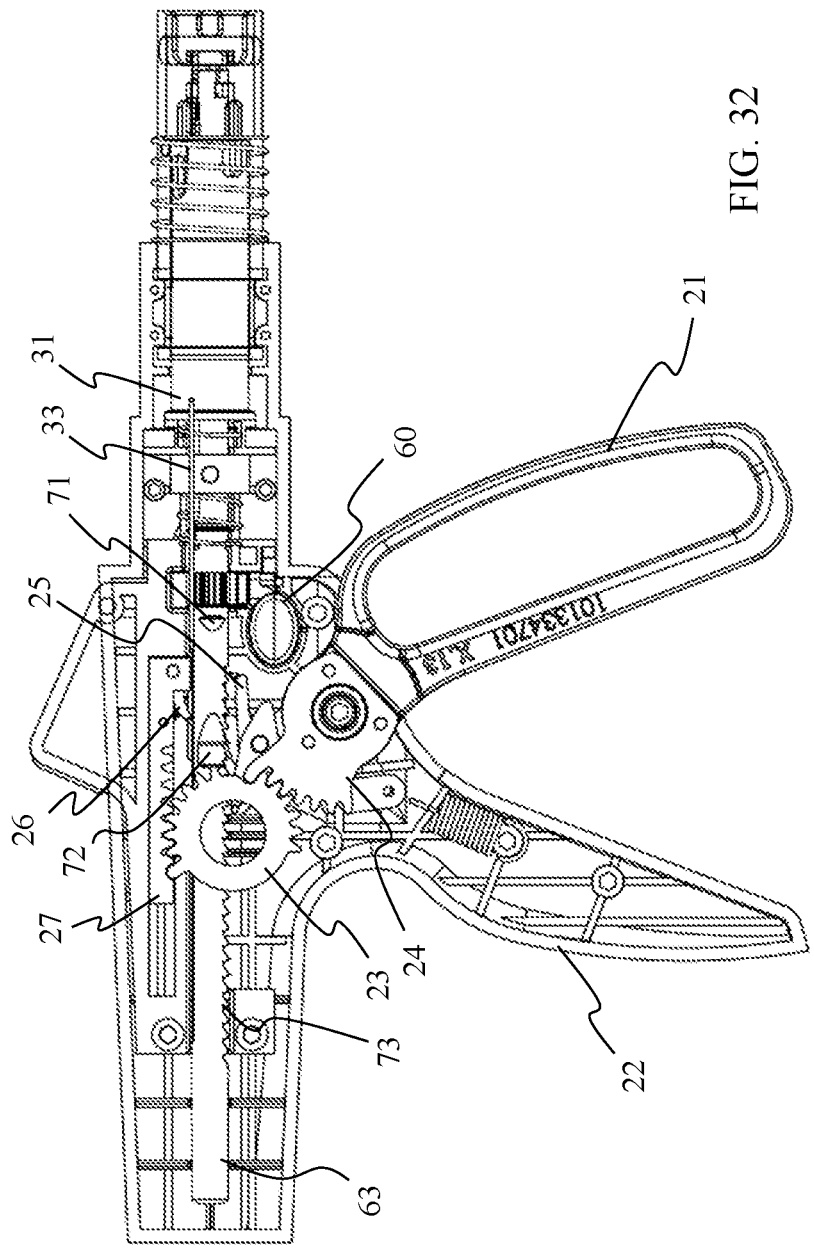
FIG. 32 is a side view of an actuator of a staple and transector receptacle of a surgical stapler in accordance with various embodiments of the present invention.
Figure 33:
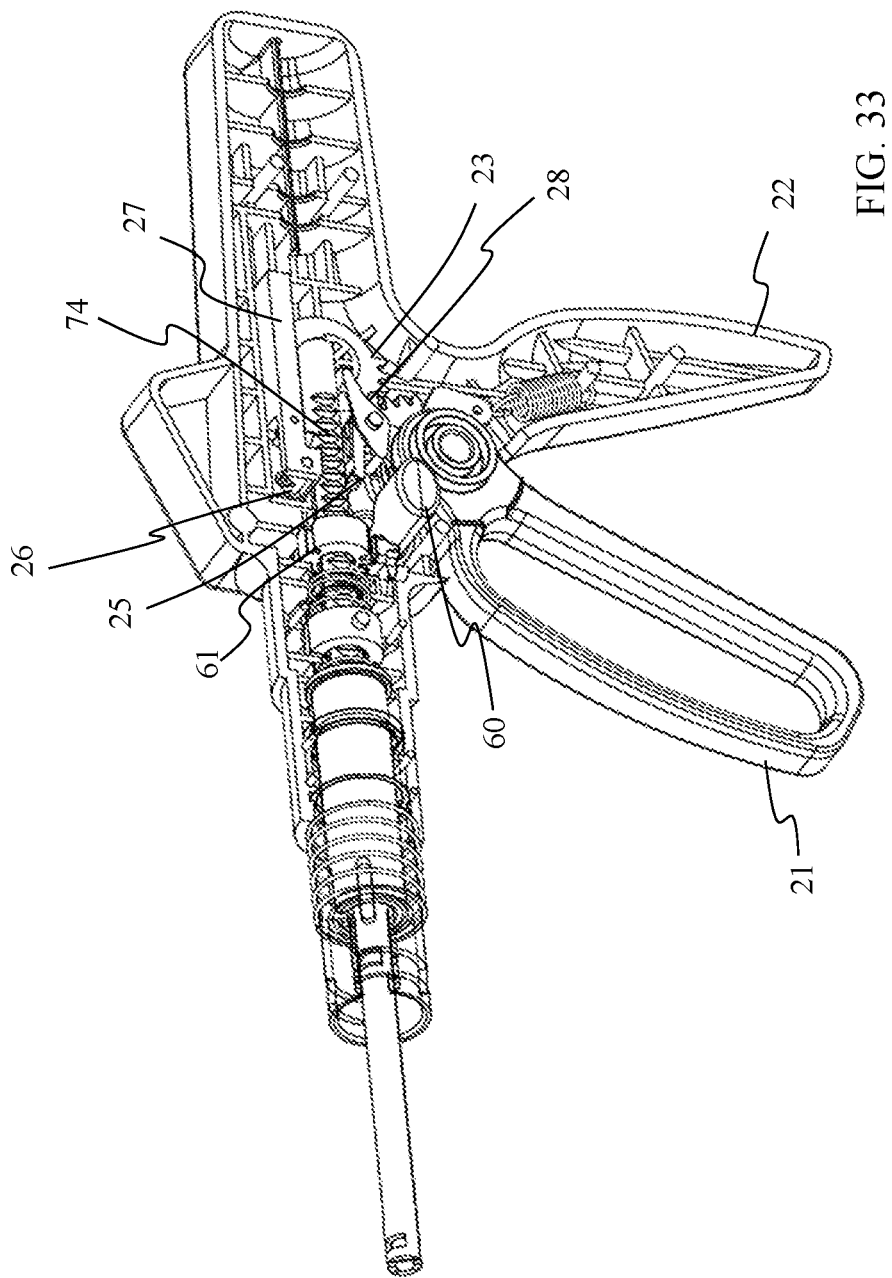
FIG. 33 is a perspective view of an actuator of a staple and transector receptacle of a surgical stapler in accordance with various embodiments of the present invention.
Figure 34:
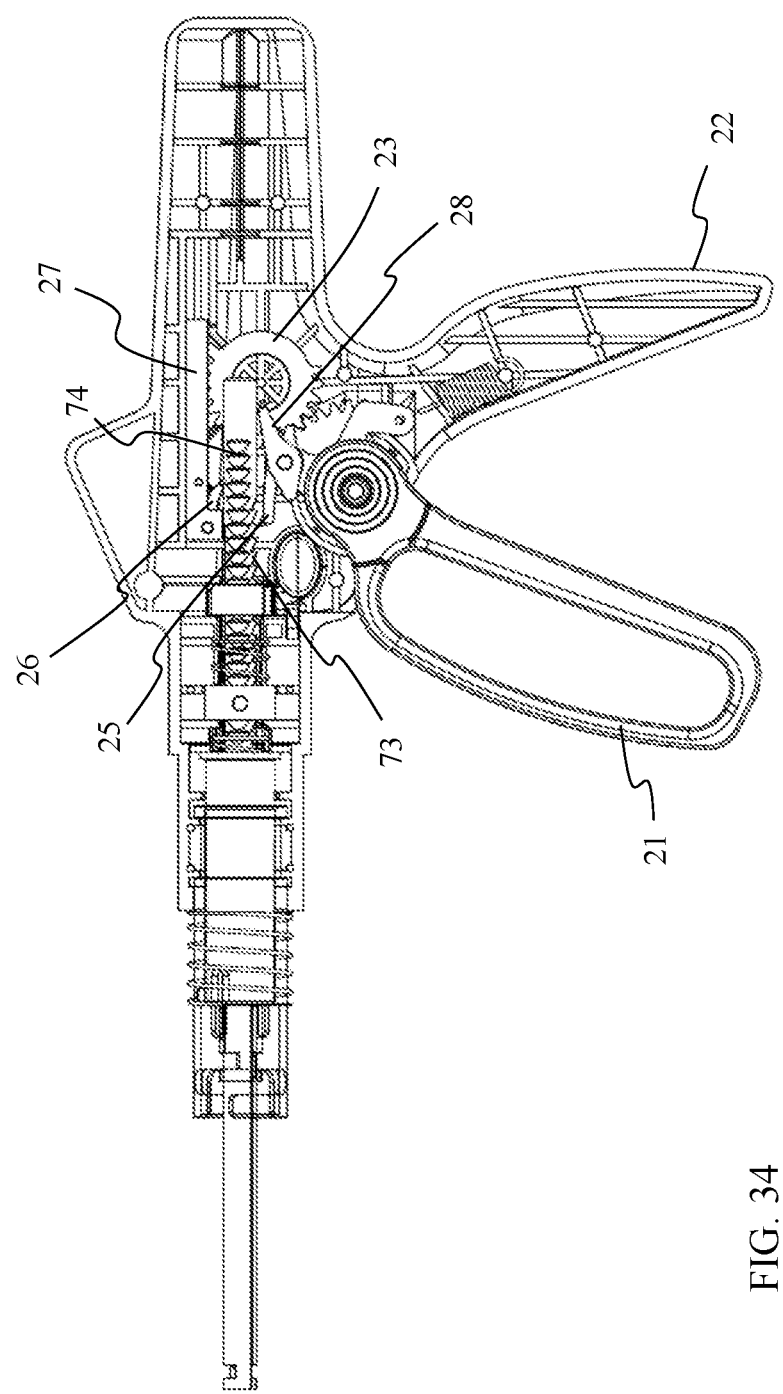
FIG. 34 is a side view of an actuator of a staple and transector receptacle of a surgical stapler in accordance with various embodiments of the present invention.
Figure 35:
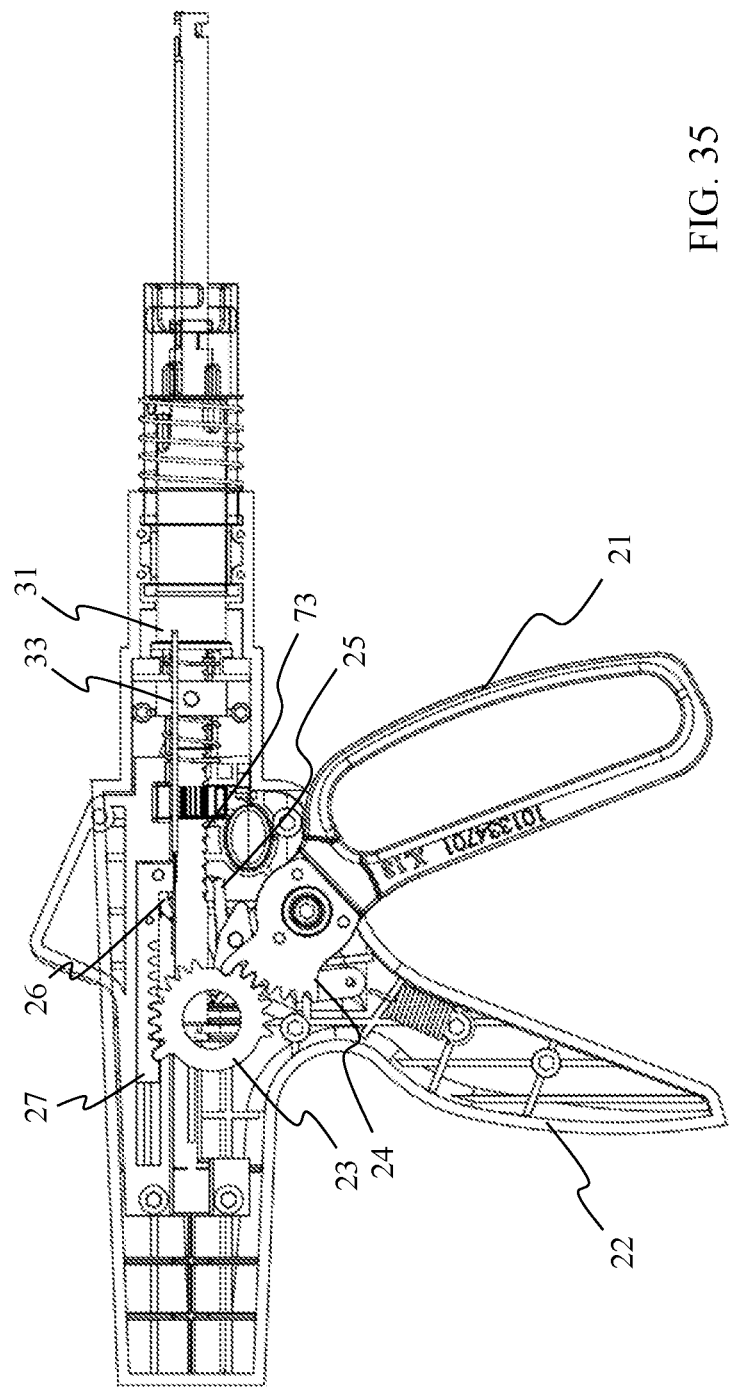
FIG. 35 is a side view of an actuator of a staple and transector receptacle of a surgical stapler in accordance with various embodiments of the present invention.
Figure 36:
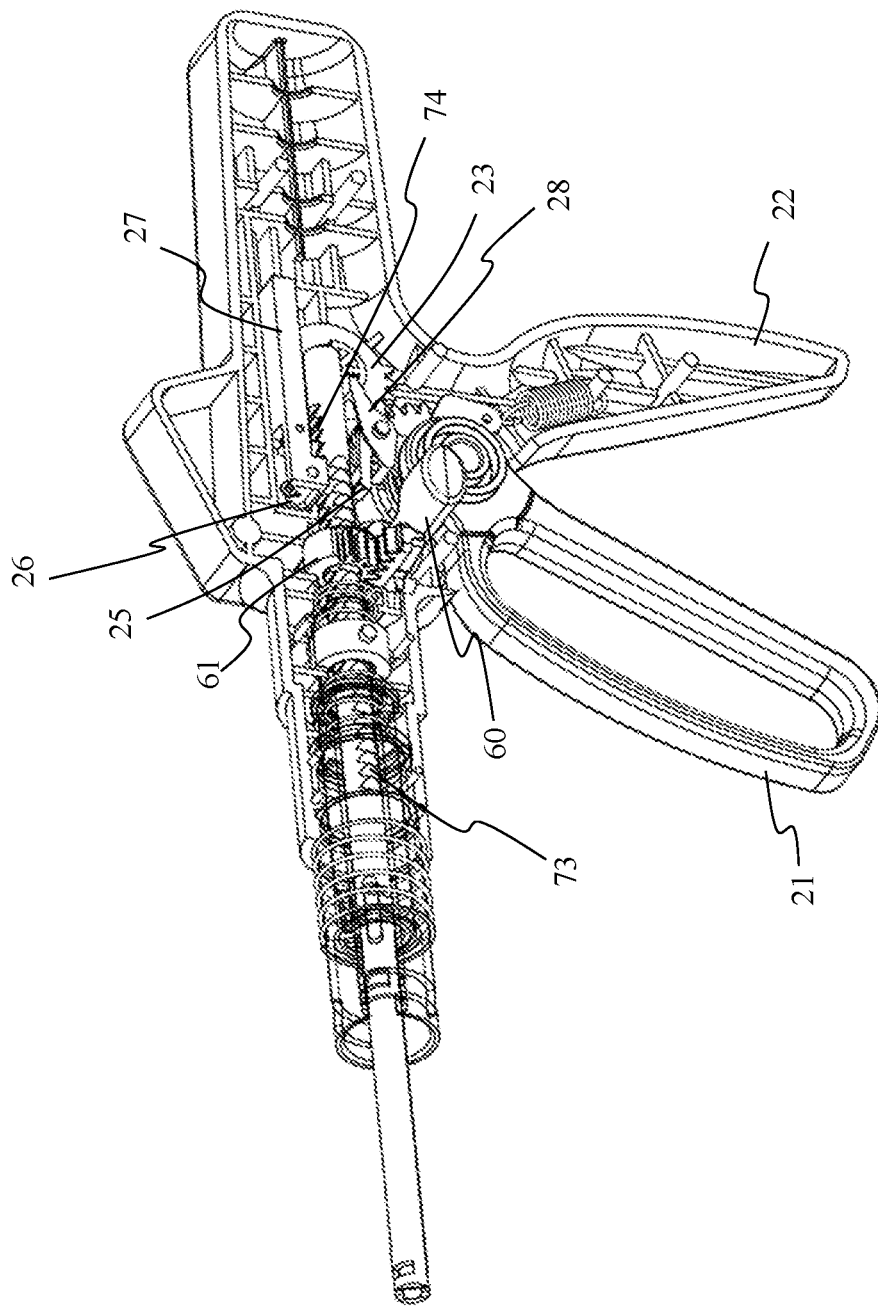
FIG. 36 is a perspective view of an actuator of a staple and transector receptacle of a surgical stapler in accordance with various embodiments of the present invention.
Figure 37:
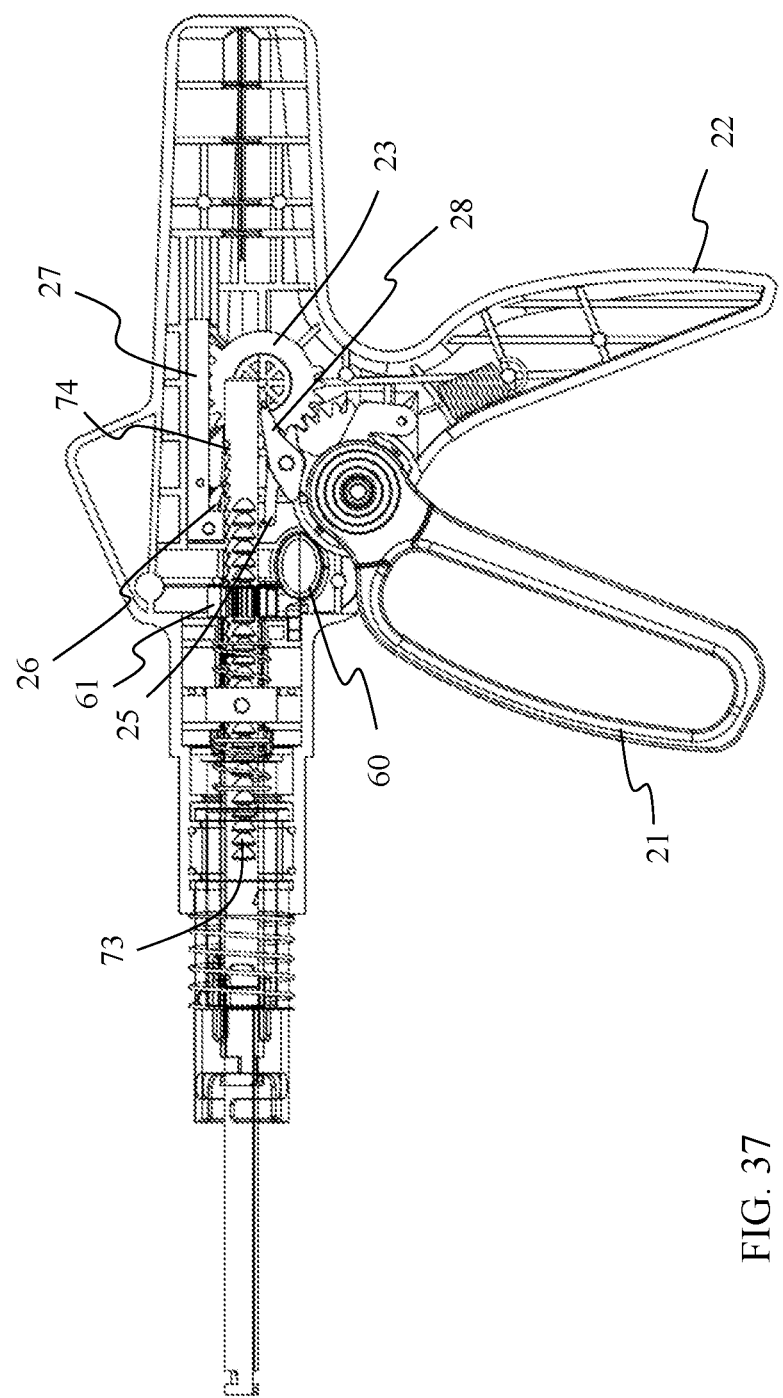
FIG. 37 is a side view of an actuator of a staple and transector receptacle of a surgical stapler in accordance with various embodiments of the present invention.
Figure 38:
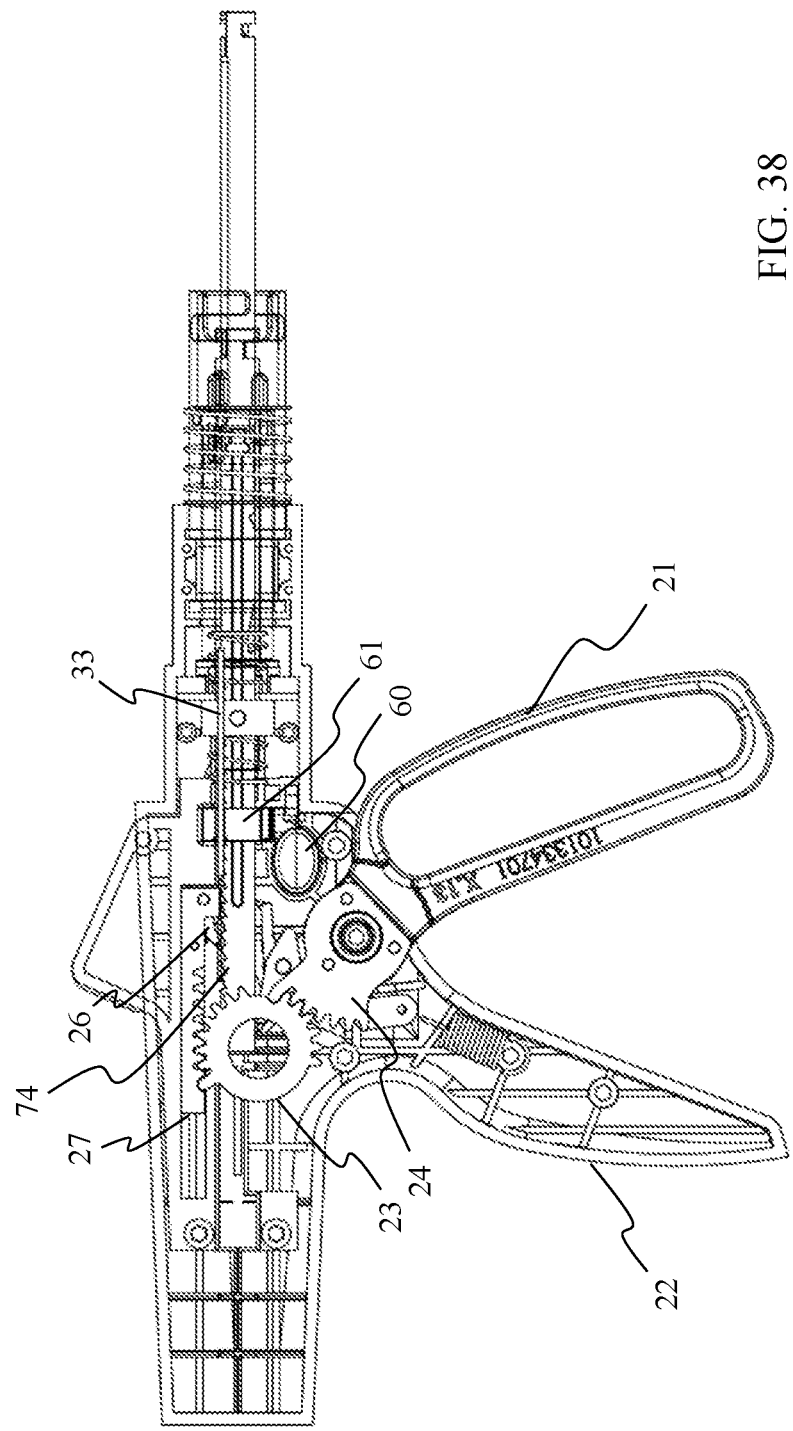
FIG. 38 is a side view of an actuator of a staple and transector receptacle of a surgical stapler in accordance with various embodiments of the present invention.
Figure 39:
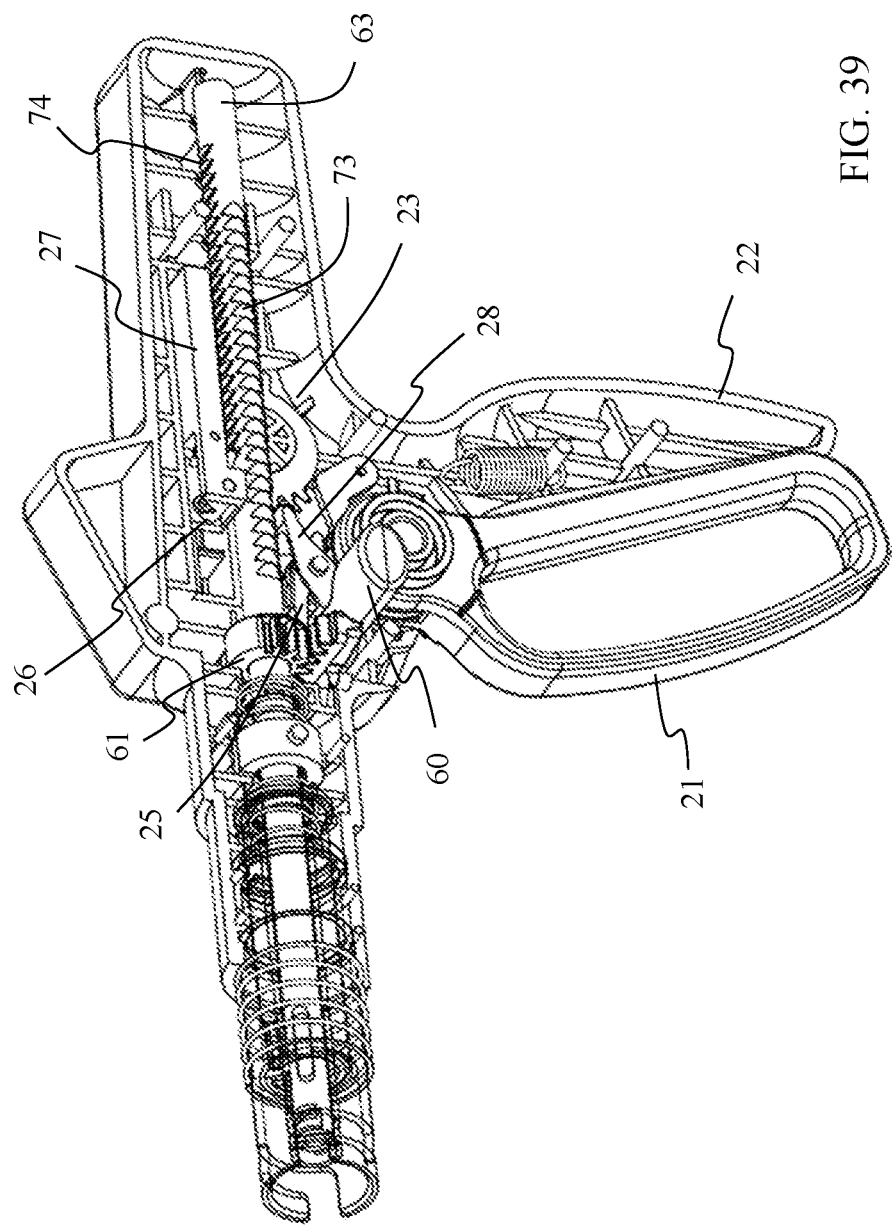
FIG. 39 is a perspective view of an actuator of a staple and transector receptacle of a surgical stapler in accordance with various embodiments of the present invention.
Figure 40:
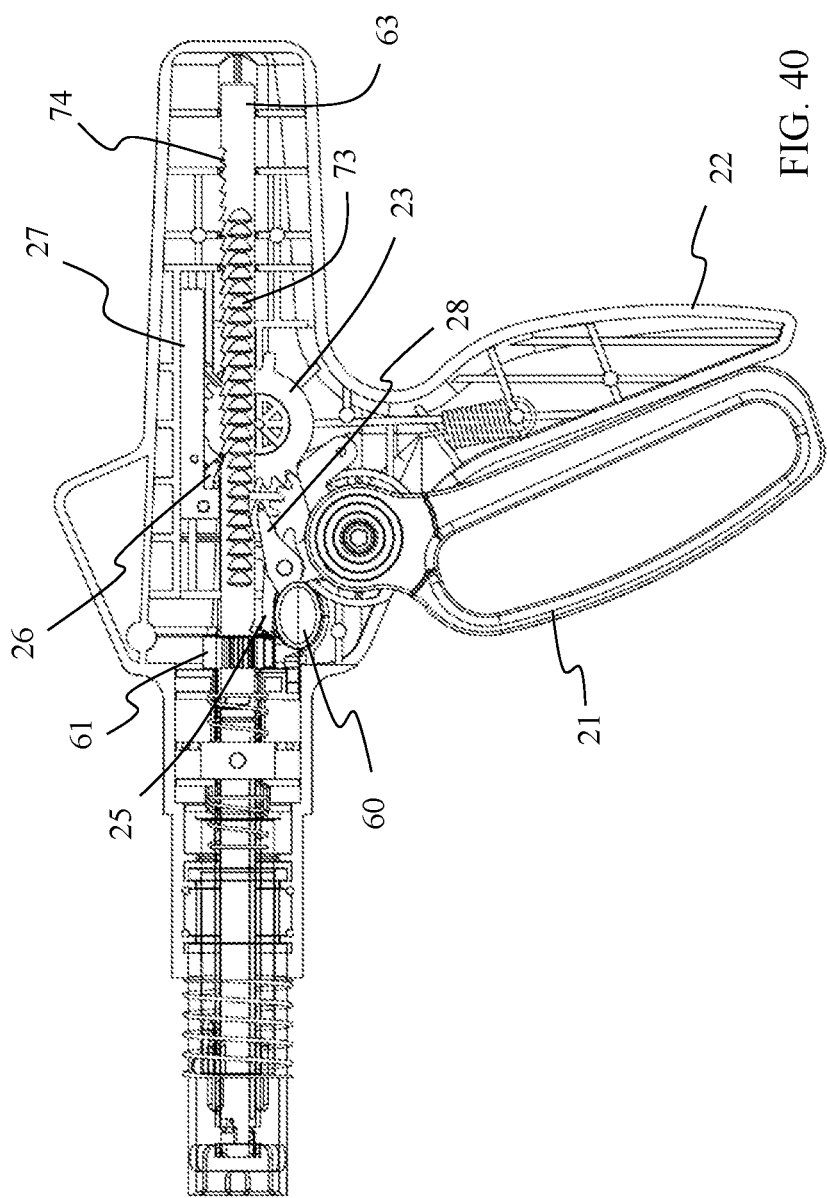
FIG. 40 is a side view of an actuator of a staple and transector receptacle of a surgical stapler in accordance with various embodiments of the present invention.
Figure 41:
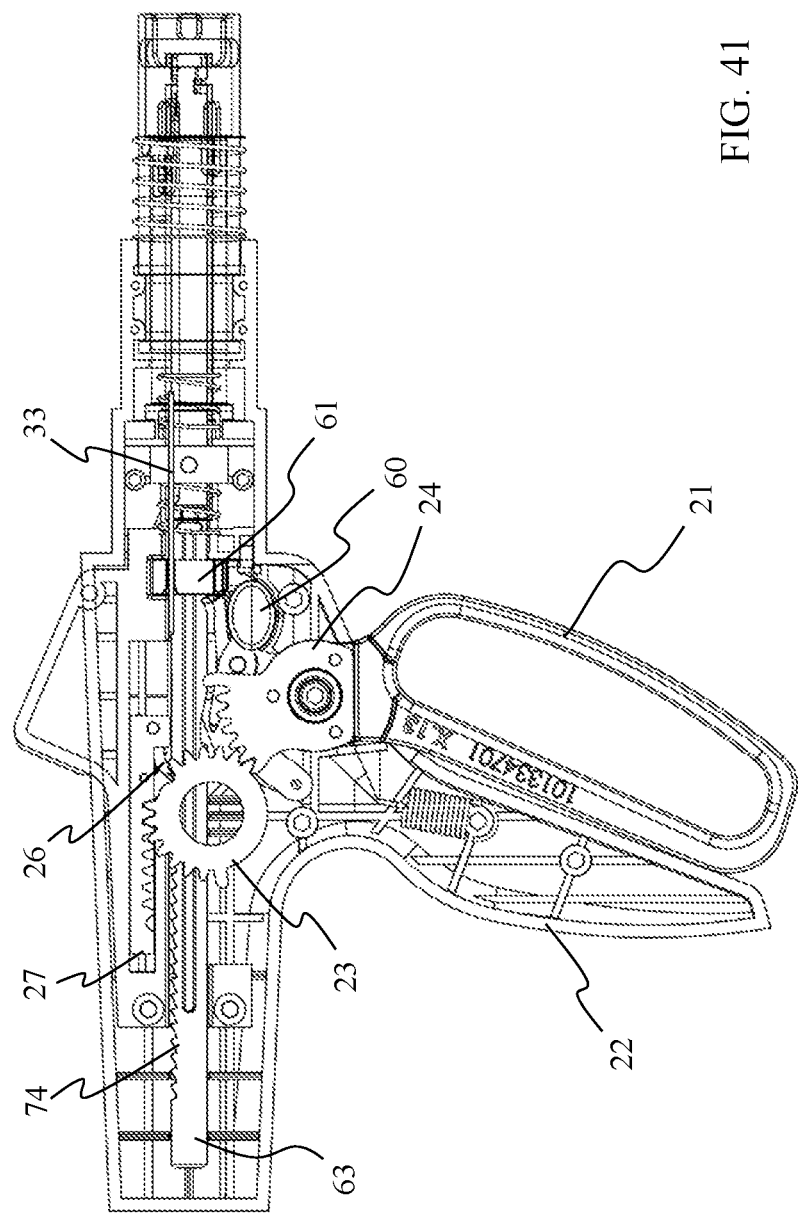
FIG. 41 is a side view of an actuator of a staple and transector receptacle of a surgical stapler in accordance with various embodiments of the present invention.
Figure 42:
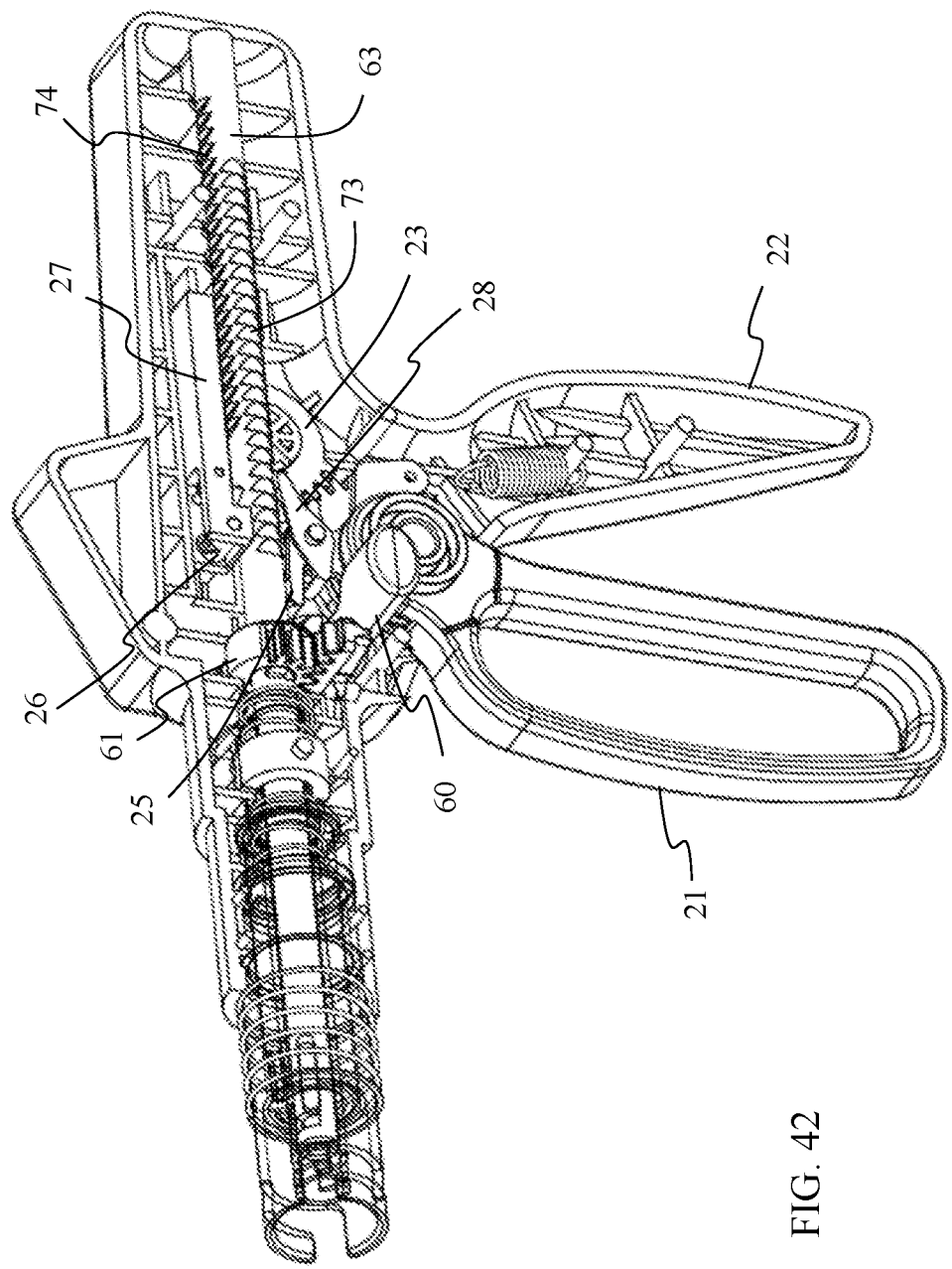
FIG. 42 is a perspective view of an actuator of a surgical stapler in accordance with various embodiments of the present invention.
Figure 43:
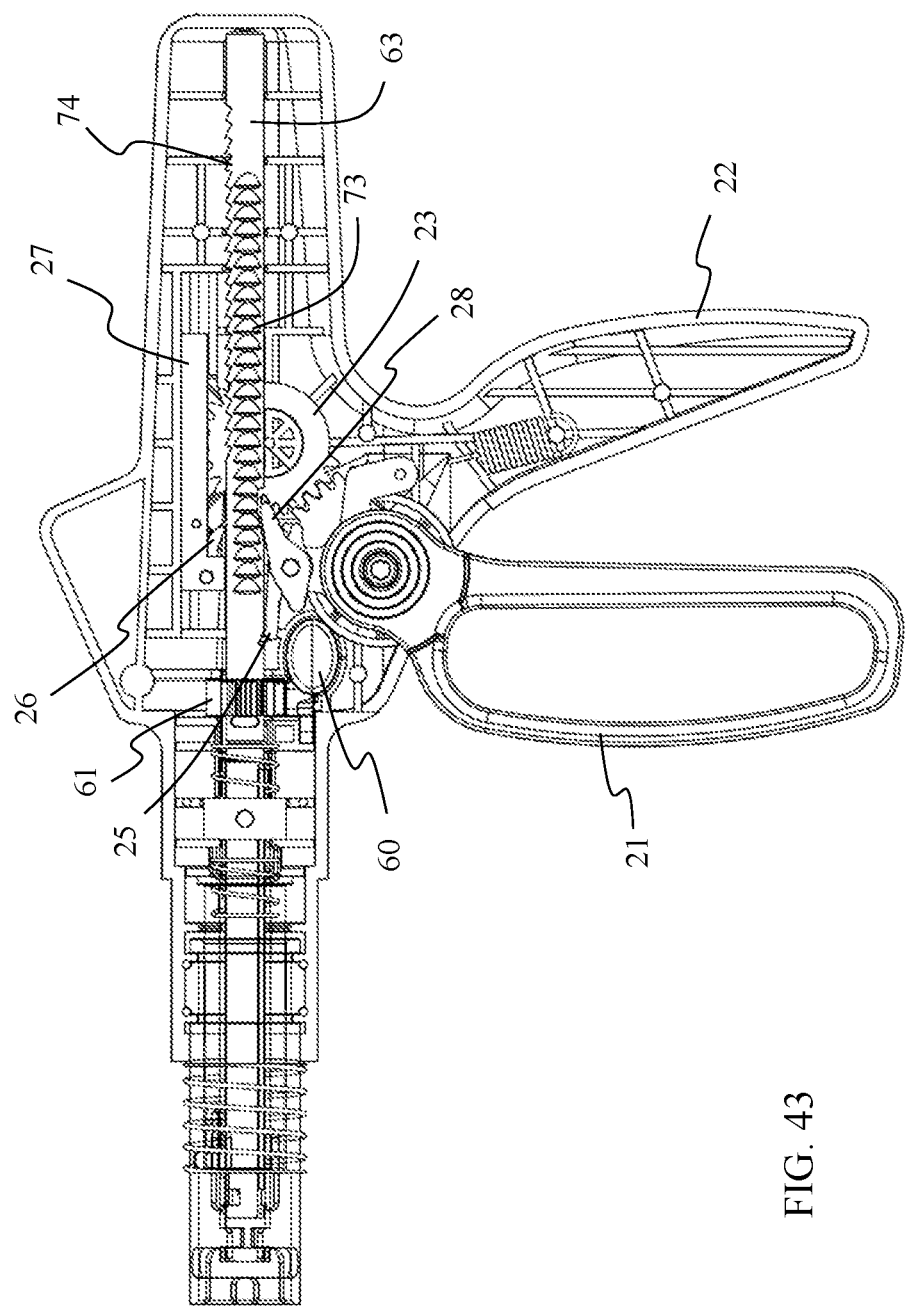
FIG. 43 is a side view of an actuator of a surgical stapler in accordance with various embodiments of the present invention.
Figure 44:
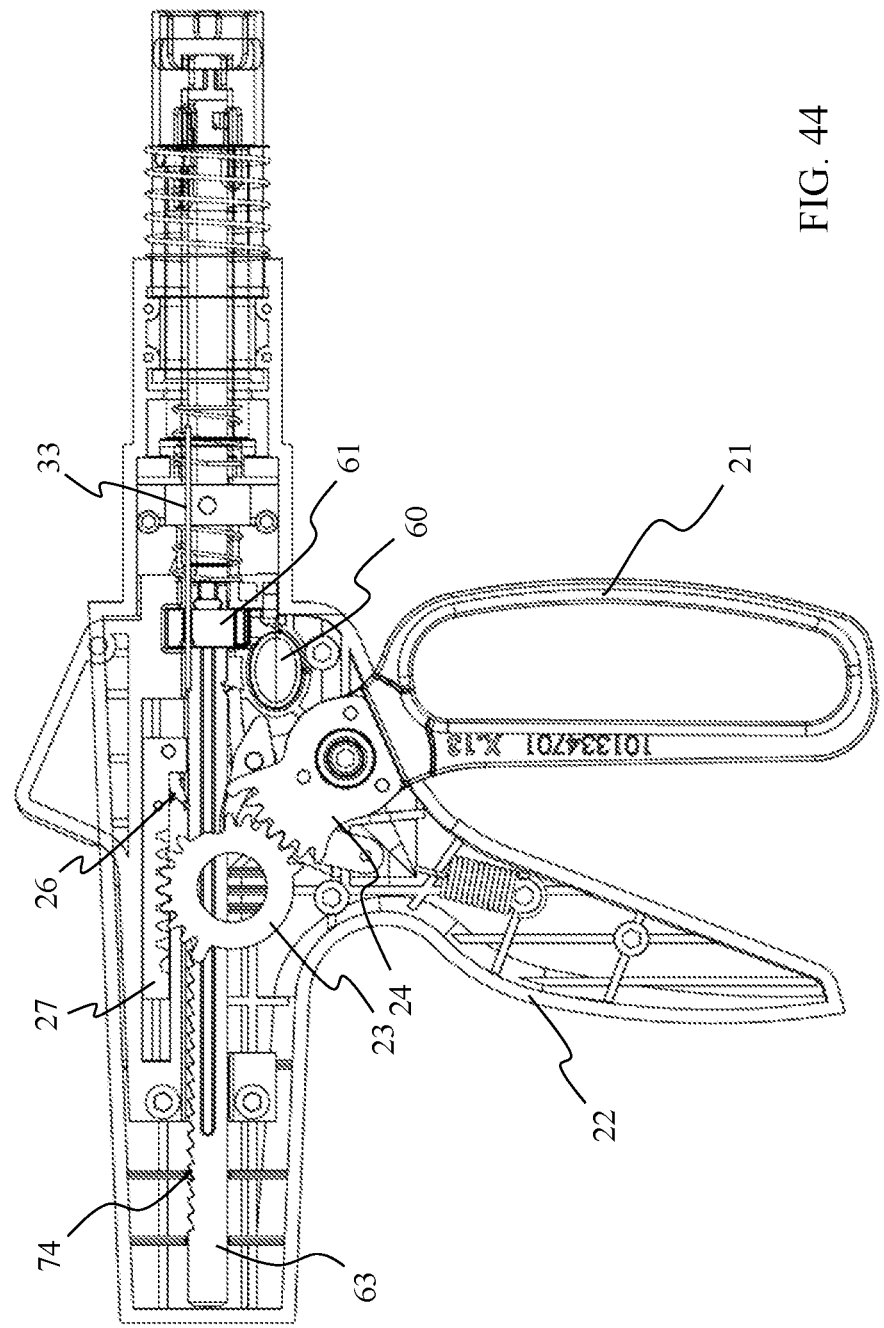
FIG. 44 is a side view of an actuator of a surgical stapler in accordance with various embodiments of the present invention.
Figure 46:
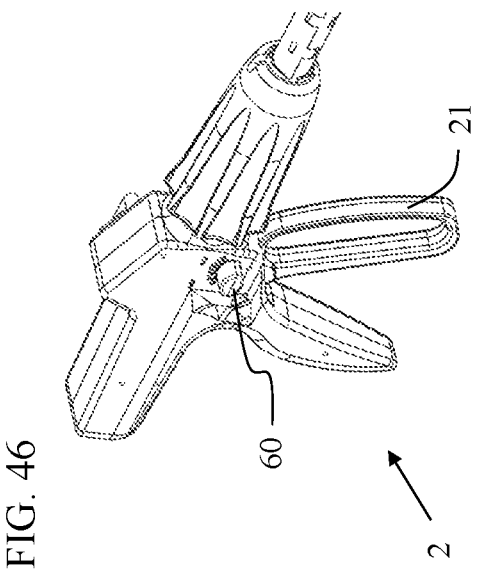
FIG. 46 is a perspective view of an actuator of a surgical stapler in accordance with various embodiments of the present invention.
Figure 47:
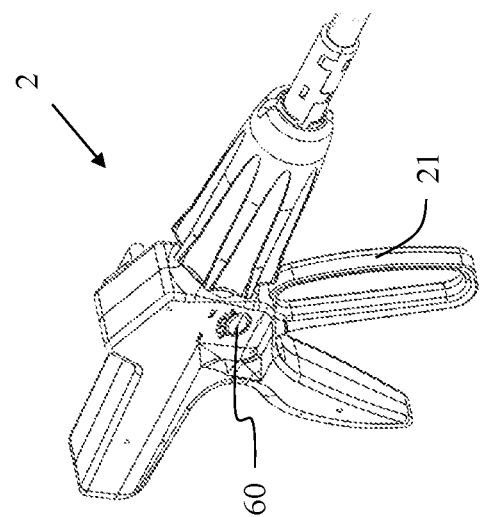
FIG. 47 is a perspective view of an actuator of a surgical stapler in accordance with various embodiments of the present invention.
Figure 48:
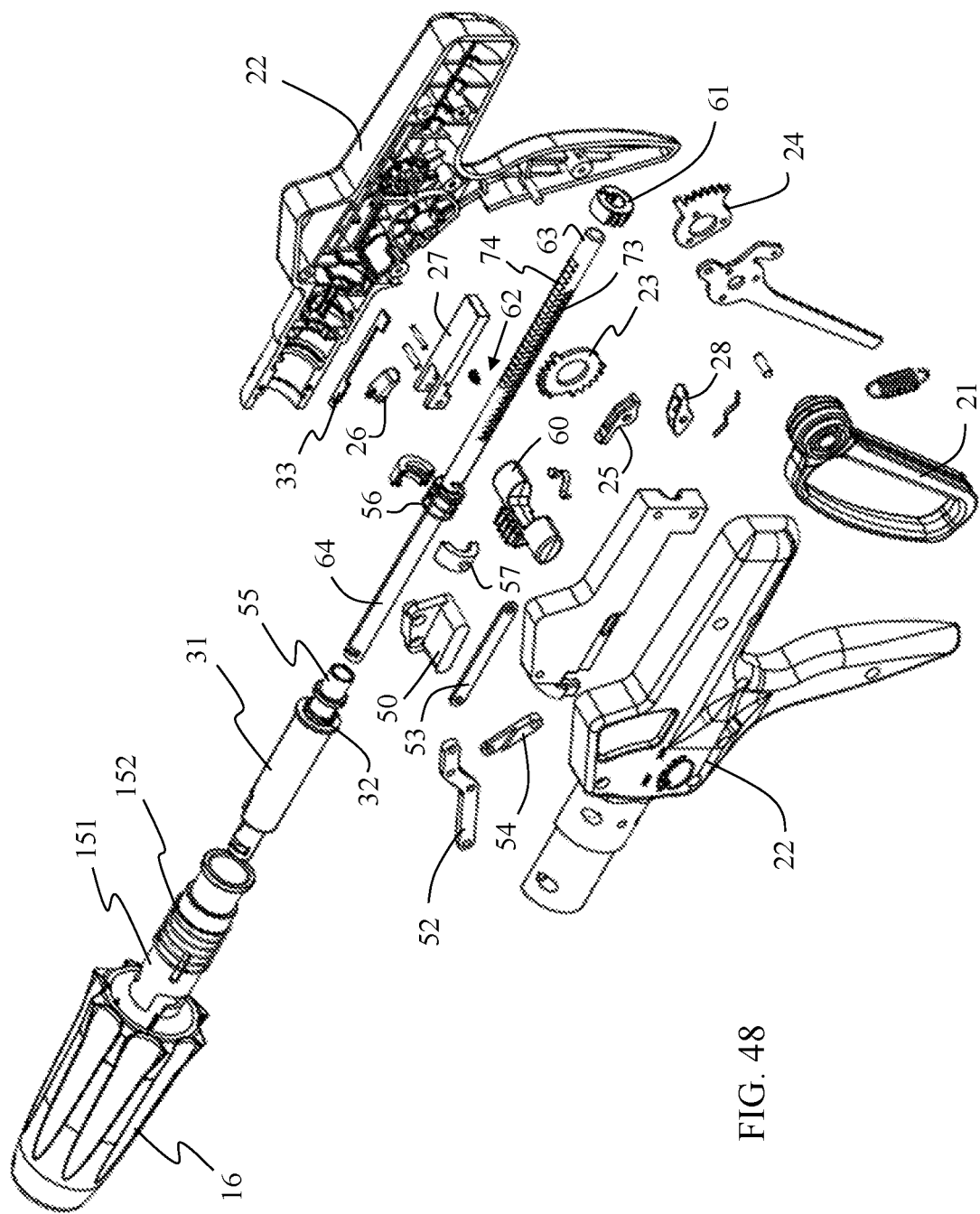
FIG. 48 is an exploded view of an actuator of a surgical stapler in accordance with various embodiments of the present invention.
Figure 49:
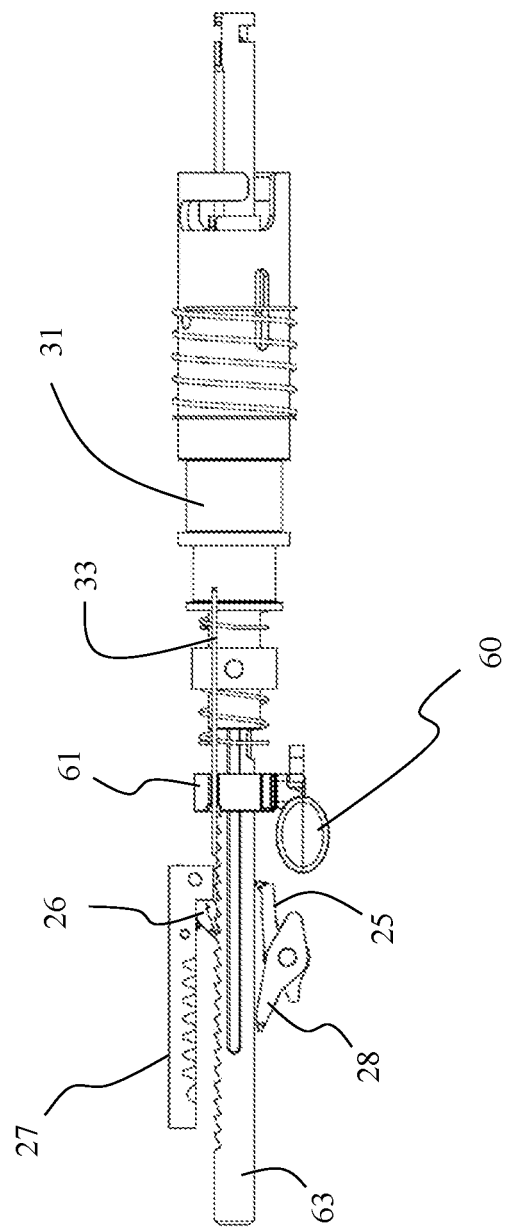
FIG. 49 is a side view of portions of an actuator of a surgical stapler in accordance with various embodiments of the present invention.

When the fire button 60 is engaged, as shown for example in FIGS. 30-32, the arming hub 61 rotates as the button translates in a direction perpendicular to the longitudinal axis 1. The arming hub 61 in one embodiment rotates in one direction, e.g., counter-clockwise, as the button translates in a linear direction and rotates in the opposite direction, e.g., clockwise, as the button translates in the opposite linear direction. The actuation rod 62 (and/or as illustrated proximal actuation rod 63) connected to the arming hub 61 also rotates clockwise as the arming hub rotates. Likewise, the actuation rod rotates counter-clockwise as the arming hub rotates in the same direction.

The arming hub 61 is circular in shape with a center opening through which the actuation rod extends there through. The outer portion of the arming hub has a slot or groove that operationally connects to a connecting arm. Along another portion of the outer portion are a series of teeth that operationally connects to or mates with a similar series of teeth of the firing button 60. The inner portion of arming hub has a protrusion or nub extending towards the center opening and mates with a longitudinal slot in the actuation rod.

With the fire or forward button engaged and the actuation rod rotated, a tip or tooth of the proximal pivot pawl 28 and distal pivot pawl 25 now operationally engage with a series of teeth 73 longitudinally disposed along the actuation rod 62 (and/or as illustrated proximal actuation rod 63). The trigger 21 when pivoted causes the proximal pivot pawl 28 and the distal pivot pawl 25 to translate distally along or relative to the actuation rod. Once the proximal pivot pawl 28 engages a tooth of the teeth 73 in or on the actuation rod, the actuation rod moves or translates distally as the trigger continues to pivot. Releasing of the trigger or moving it away from the handle base 22 causes the proximal pivot pawl 28 and the distal pivot pawl 25 to move back proximally along or relative to the actuation rod. However, the tip or tooth of the proximal pivot pawl 28 and distal pivot pawl 25 now operationally engage with a more proximal portion of the series of teeth 73 longitudinally disposed along the actuation rod 62. The distal pivot pawl 25 engaging a tooth of the series of teeth 73 prevents proximal movement of the actuation rod, the actuation slides and the opening of the jaws. The proximal pivot pawl engaging a tooth of the series of teeth 73 allows further distal movement of the actuation rod, the actuation slide, the actuation beam, continued firing of the staples and cutting of tissue between the jaws. As such, multiple strokes or squeezing and releasing of the trigger may be performed to fully move the proximal and distal pivot pawl to completely eject the staples and cut the tissue between the jaws. In one embodiment, only a single stroke is utilized to eject the staples and cut the tissue between the jaws. The actuator at its end of travel or complete firing of the staples is shown for example in FIGS. 33-35 and 45C-45D.

In accordance with various embodiments, the trigger 21 is coupled to an intermediate action gear 23 and a trigger action gear 24. The trigger action gear 24 in the illustrated embodiment has a center opening through which a pivot protrusion of the movable handle extends there through. The trigger action gear includes a series of teeth engaged or connected to a set of two sets of teeth on the intermediate action gear. Pivoting the trigger 21 rotates the trigger action gear that correspondingly rotates the intermediate action gear 23. In particular, squeezing the trigger 21 causes the trigger action gear 24 to rotate in one direction, e.g., counter-clockwise, that in turn causes the intermediate action gear 23 to rotate in the opposite direction, e.g., clockwise. The other set of teeth of the two sets of teeth of the intermediate action gear engage with teeth on a movable rack 27 and thereby moves the rack proximally. The movable rack in one embodiment is positioned parallel to the actuation rod. Moving the rack proximally also moves or translates a reverse pawl 26 proximally. In the firing configuration and during the firing of the staples, the tip of the reverse pawl sits and slides against an outer surface or slot in or on the actuation rod 62 (and/or as illustrated proximal actuation rod 63). As such, the rack is movable distally and proximally based on the actuation or pivoting of the trigger.

In one embodiment, when the tip of the reverse pawl 26 moves to a proximal or proximal most position it engages a wall in the slot of the actuation rod or a tooth along the actuation rod 62. The wall or tooth of the actuation rod 62 acts as a hard or additional stop preventing further distal movement of the actuation rod.

The rack 27 is disposed in a slot or channel in the handle base 22 and in one embodiment the rack 27 when moved to a proximal or proximal most position engages a wall or proximal end of the slot that prevents further proximal movement of the rack 27 and thus resists further rotation of the intermediate action gear 23 that resists further rotation of the trigger action gear 24 and thereby prevents further squeezing or closing of the trigger 21. Likewise, in one embodiment, the rack 27 when moved to a distal or distal most position it engages a wall or distal end of the slot that prevents further distal movement of the rack 27 and thus resists further rotation of the intermediate action gear 23 that resists further rotation of the trigger action gear 24 and thereby prevents further opening of the trigger 21 or movement of the trigger away from the handle base.

Accordingly, actuation of the trigger towards the handle base 22 rotates the intermediate action gear 23 in one direction, e.g., clockwise, which translates the rack 27 proximally and actuation of the trigger away from the handle base rotates the intermediate action gear in an opposite direction, e.g., counter-clockwise, which translates the rack distally. The reverse pawl 26 pivotable connected to a distal end of the movable rack 27 slides proximally and distally as the rack translates proximally and distally.

In accordance with various embodiments, the surgical stapler provides a one-way automatic vertical adjustment of the staple cartridge 5. The cartridge 5 is moved vertically within lower jaw 12 and, in one embodiment, the cartridge is movable vertically relative to a retainer 121 of the lower jaw 12. The cartridge in the lower jaw is movable vertically (e.g., as illustrated by arrow V) towards the anvil through the interaction of ramps 83 located on a bottom surface of a cartridge lift 82 with ramps 81 located on a rampway 80. The cartridge sits on an upper surface of the cartridge lift 82. The upper surface of the cartridge lift 82 is generally flat and/or devoid of any ramps. In one embodiment, the cartridge lift includes guides or ridges along the sides of the cartridge lift to ensure proper seating or assembly of the cartridge on the upper surface of the cartridge lift. The cartridge lift in one embodiment also includes a channel or slot there through to accommodate the blade and/or the upstanding edge of the actuation beam movable longitudinally there through. The cartridge in the illustrated embodiment is arranged to move only in one direction, vertically (e.g., as illustrated by arrow V). The cartridge lift is also positioned between the cartridge and the rampway. The rampway remains stationary and is not movable while the cartridge is movable in one direction, vertically, and away from the rampway. When the cartridge lift is moved longitudinally and proximally (e.g., as illustrated by arrow H), the ramps 83 of the cartridge lift slide along the ramps 81 of the rampway 80, which remains fixed within the lower jaw 12, and thereby raises the cartridge 5 vertically. As such, the surgical stapler includes a series of ramps to lift the cartridge vertically and allow for the adjustment of the formed staple heights to a plurality of intermediate points between upper and lower staple height and gap limits and along a slope of the ramps.

The cartridge lift 82 in one embodiment is also biased in the proximal longitudinal direction. Such biasing in one embodiment only occurs once the height adjustment mechanism has been activated or firing operation has been commenced, e.g., the actuation slide has traveled past a first predefined distance. In one particular embodiment, the cartridge lift 82 is biased or tensioned by a cartridge lift spring 87 pulling the cartridge lift in the proximal direction along or aligned with the longitudinal axis. The biased lift provides an active vertical force against the cartridge 5 forcing it against the tissue held between the jaws 11, 12.

In a further embodiment, initially, the spring 87 or tension mechanism is locked or inactivate and thus does not provide any tension or force pulling the cartridge lift in the proximal direction. As such, when inactive, the cartridge 5 and the associated cartridge lift 82 remains at its initial or lowest vertical position.

The cartridge lift 82 is biased or pulled in the proximal direction (e.g., as illustrated by arrow H) by the spring 87 when the lift is unlocked or the spring is released. Once unlocked, the cartridge lift is pulled or tensioned proximally and thus resists movement distally back to its original or initial position or simply cannot move freely distally. Likewise, the cartridge 5 is lifted vertically from its initial or lowest position. The amount or distance the cartridge travels vertically is based on the force applied by the spring, the amount of tissue between the jaws and the clamping or compression force applied by the jaws closed over the tissue. In accordance with various embodiments, the cartridge applies a uniform one-way constant vertical force as biased by the force applied by the spring. The cartridge lift and/or lift bias or spring (e.g., spring 87) in various embodiments is blocked by lift lock and in various embodiments the lift lock is not user accessible. Once the lift lock is displaced, the cartridge lift is pulled or tensioned and thus resists is unable to move back to its original or initial position.

In the illustrated embodiment, the cartridge lift 82 is connected to a cartridge lift beam 84 that is connected to a cartridge lift barrel 85. In one embodiment, the proximal end of the cartridge lift includes an opening for receiving a pin and a slot for receiving a flange connected to or extending from the distal end of the cartridge lift beam 84. The proximal end of the lift beam is connected, e.g., welded or riveted, to the distal end of the lift barrel 85. The lift barrel has a central opening and is disposed around or surrounds the actuation cover tube 185. The lift barrel is thus coaxial with the actuation cover tube 185, the actuation slide 180, the actuation rod 62 and the lift beam 84 and is likewise parallel to the actuation slide 180 and the actuation rod 62. The lift barrel is biased in the proximal direction (e.g., as illustrated by arrow H) by a cartridge lift spring 87. The cartridge lift spring also surrounds the actuation cover tube 185 and is positioned aligned and between the upper and lower outer covers 91, 92 and the lift barrel 85. In the illustrated embodiment, a cartridge lift spacer 86 is placed between the spring and the lift barrel (e.g., after/behind the spring) or in one embodiment between the upper and lower outer covers and the spring (e.g., before/in front of the spring) to accommodate tolerances in assembly or sizing of the spring and thus strength of the spring to ensure the appropriate compression force is applied for a given tissue grasped between the jaws. The lift barrel 85 remains blocked or is prevented from moving proximally until or just before the staples can be fired or the stapler is in a firing configuration or position. The lift barrel 85 in various embodiments is blocked by lift lock and in various embodiments the lift lock is not user accessible. In various embodiments, the lift lock is a reload or STR reuse lockout. In various embodiments, the STR reuse lockout 41 is biased to be aligned with the lift barrel 85 and thus in contact with the lift barrel to prevent longitudinal proximal movement of the lift barrel. Once the STR reuse lockout is misaligned or moved out of contact with the lift barrel, the lift spring 87 biases the lift barrel proximally. In various embodiments, the lift lock or the STR reuse lockout is in contact or coupled to the actuation slide and thus becomes misaligned once the actuation slide starts the firing operation or just before the staples can be fired or is ready to be fired.

In one embodiment, the lift barrel also slides over the STR reuse lockout preventing the alignment of the STR reuse lockout with the lift barrel. As such, once the lift barrel is activated, the lift barrel cannot be locked again or returned to its initial or proximal position. Likewise, the cartridge lift connected to the lift barrel by the lift beam cannot return to its initial or proximal position. Also, the cartridge lift under the influence of the spring and barrel movement, moves longitudinally and proximally (e.g., as illustrated by arrow H). The interaction of the ramps of the cartridge lift and ramps of the rampway as the cartridge lift moves proximally causes the cartridge lift to move the staple cartridge 5 uniformly vertically (e.g., as illustrated by arrow V). In accordance with various embodiments, slots or channels interacting with corresponding protrusions or detents on the cartridge, the retainer or both ensure or assist in a uniform and singular vertical movement of the cartridge. The interaction of the ramps and biasing of the lift barrel also act as an integrated height lockout for the staple cartridge allowing the stapler to fire at the adjusted staple height without being able to be forced back open or to a previous position.

The adjustment of the cartridge height occurs while the jaws are closed on a piece of tissue and is made automatically by the stapler. The surgeon/user does not choose the staple height or staple size. As such, staple height is set automatically by stapler based on thickness of tissue and the resistance it provides. The adjustment of the cartridge height also produces a movement of the cartridge with respect of the anvil while the top and bottom surfaces are parallel. During the adjustment, the top and bottom surfaces remain parallel and the surfaces remain parallel once the movement is complete.

As shown in FIG. 50A, a distal end of a STR reuse lockout 41 initially sits on a top outer surface of actuation slide 180 or in one embodiment, the proximate actuation slide 181. In one embodiment, a proximal end of the STR reuse lockout is connected to the actuation cover tube 185. A leaf spring sits on top of the STR reuse lockout and is coupled to the cover tube. The leaf spring biases or pivots the distal end of the STR reuse lockout against or down on the actuation slide. Referring now also to FIG. 51B, as the jaws are opened and closed, the distal end of the STR reuse lockout will remain on the top outer surface of the actuation slide and riding longitudinally proximally and distally as the slide moves and the jaws are opened and closed.

Once firing of the staples is initiated or activated, the actuation slide moves forward distally allowing the distal end of the STR reuse lockout 41 to fall within a slot or opening 187 in the actuation slide. As such, the distal end of the STR reuse lockout rides or sits on the outer surface of the slot within the actuation slide as shown in FIGS. 51A-C as the actuation slide travels longitudinally distally to eject the staples from the staple cartridge.

The top or outer surface of the distal end of the STR reuse lockout falls under a bottom surface of the outer cover tube, the lift barrel or both. Likewise, the bottom or lower surface of the distal end of the STR reuse lockout rides on top of the slot or lower distal surface of the actuation slide. As such, the distal end of the STR reuse lockout is disposed or trapped between the outer cover tube or lift barrel and the actuation slide. Additionally, the STR reuse lockout does not move longitudinally unlike the actuation slide but pivots or moves perpendicular or transverse to the longitudinal direction of the actuation slide.

As the actuation slide moves back, the distal end of the STR reuse lockout gets trapped within a distal slot in the actuation slide as shown in FIGS. 52A-B. As such, the STR reuse lockout prevents further movement of the actuation slide in either the proximal or distal longitudinal directions. As such, the STR is now unable to fire or eject any staples or move the knife blade or reset the cartridge lift. In accordance with various embodiments, the staple cartridge now raised may serve as an indicator that the STR and/or cartridge is now unable to fire, is devoid of staples, stapling or cutting operations are complete or any combination thereof.

In accordance with various embodiments, the staple cartridge 5 includes one or more detents or protrusions 551, 552 positioned and shaped to mate with and slide within slots or openings 1211, 1212 disposed on the lower jaw 12. The protrusions 551, 552 are positioned on the side walls of the staple cartridge and the slots 1211, 1212 are positioned on the side walls of a cartridge holder, retainer 121 or lower jaw 12 of the stapler. The engagement of the protrusions and slots ensures that the staple cartridge can move vertically but also ensures that the staple cartridge only moves vertically and not side to side or longitudinally distally or proximally. In various embodiments, protrusions or detents, e.g., protrusions 1211, restrict movement of the staple cartridge other than vertically and prevent removal of the staple cartridge from the lower jaw of the stapler. In various embodiments, the staple cartridge although movable vertically is permanently affixed to the jaw and thereby restricts reuse of the staple cartridge or inadvertent discharge or removal of the staple cartridge ensuring consistent stapler operations. In various embodiments, only a single protrusion or a set of protrusions, e.g., protrusions 1211, protrusions 1212, or combinations thereof, are disposed on the staple cartridge.

The staple cartridge in various embodiments is a single monolithic structure to assist in applying a uniform force to compress the tissue. Individual staple pushers are disposed in the stapler cartridge in individual pockets with individual staples in each pocket. Activation of a staple pusher ejects the associated staple out of the staple pocket and into the clamped tissue and an anvil forming or closing the staple.

In one embodiment, the fins of the slider 17 are longitudinally offset as such fins on one side, e.g., a right side relative to the blade, is set in a more distal position then the fins on the opposing side, e.g., a left side relative to the blade. The left side fins thus is placed in a more proximal position than the right side fins. The offset of the fins provides a distribution of force in ejecting of the staples and as such reduces potential excessive compression of the tissue and the amount of force required to sequentially eject the staples from the staple pockets via the staple pushers.

The stapler includes an articulation lever or switch 50 that toggles the jaws 11, 12 from a zero or initial position to an angled or 45 degrees position relative to the longitudinal axis along the elongate shaft and back again to the zero or initial position. When a surgeon activates the lever, the lever engages an articulation forward arm 52 and an articulation rear arm 54 that moves from a split or misaligned position to an aligned and linear position. One end of the rear arm is connected to the lever and the other end of the rear arm is connected to the housing base. One end of the forward arm is connected to the rear arm along its middle portion and the other end of the forward arm is connected to an articulation extension arm 53.

The other end of the articulation extension arm 53 is connected to an articulation hub 57 surrounding and connected to an articulation barrel 55. The articulation barrel has a bayonet coupling arranged to releasably connect to an articulation beam 51 with a distal end connected to a pivot post near a jaw pivot post that pivotally connects the jaws 11, 12. The pivot post is disposed perpendicular to the jaw pivot post and offset the center or longitudinal mid-line of the elongate shaft. Placing the articulation forward and rear arms in-line with each other pulls or slides the articulation extension arm 53 proximally that slides the articulation hub and barrel proximally pulling the articulation beam proximally. Proximal movement of the beam pulls on the pivot post causing the upper and outer covers 91, 92 connected to the jaws 11, 12 and connected to the pivot post to be pulled proximally. Since the pivot post is arranged offset the center of the shaft, the jaw covers moves in a direction towards the pivot post to place the jaws in an angled position. With the lever fully depressed, the forward and rear arms are aligned and set in place thereby holding the jaws in the angled position. When the lever is released or moved back to the original or initial position the forward and rear arms split or become misaligned causing the pulling of the articulation beam proximally to be released and thus the articulation beam is allowed to move distally. Movement of the articulation beam distally causes the upper and lower outer covers and thus the jaws 11, 12 to pivot back to an initial or zero position aligning the jaws to the longitudinal axis 1 of the stapler.

In one embodiment, the articulation barrel includes a bias component, e.g., an articulation barrel spring 56, surrounding the articulation barrel and positioned between the outer surface of the articulation barrel and the inner surface of the articulation hub. The spring biases the articulation barrel distally that also biases the articulation beam distally and thereby biases the jaws to the initial or zero position.

In accordance with various embodiments, the reverse button (or moving the fire button in the opposite direction) may the pressed at any time while the actuation rod 62 is translating distally. Engaging the reverse button reverses the operation of the stapler and thereby enables the longitudinal movement of the actuation rod back or proximally.

As shown for example in FIGS. 36-38 and 46-47, when the reverse button is pushed (the fire button 60 pushed again), the arming hub 61 rotates back to its initial position or in the opposite direction, e.g., clockwise, as the button translates in a linear direction. The actuation rod 62 (and/or as illustrated proximal actuation rod 63) connected to the arming hub also rotates back to its initial position or in the opposite direction, e.g., clockwise.

With the fire or reverse button engaged and the actuation rod rotated, the reverse pawl 26 connected to the movable slide or rack 27 becomes engaged or is engageable with a series of teeth 74 longitudinally disposed along or in the actuation rod 62. With the actuation rod 62 at a distal or distal most position, the teeth 74 become accessible or exposed to the reverse pawl 26.

Actuation or squeezing of the trigger 21 towards the handle base 22 rotates the trigger action gear 24 that rotates the intermediate action gear 23 which translates the rack 27 proximally. The reverse pawl 26 connected to the rack 27 also moves proximally and longitudinally. The reverse pawl 26 also being engaged with a tooth of the teeth 74 on the actuation rod 62 also moves the actuation rod 62 proximally and longitudinally.

Releasing of the trigger or moving it away from the handle base 22 causes the reverse pawl 26 and the rack to move back distally through the interaction and cooperation of the trigger and intermediate action gears. However, the tip or tooth of the reverse pawl 26 becomes operationally engage with a more distal portion of the series of teeth 74 longitudinally disposed along the actuation rod 62. Additionally, the engagement of the reverse pawl with the teeth 74 prevents or resists distal movement of the actuation rod 62. As such, multiple strokes or squeezing and releasing of the trigger may be performed to fully move the actuation rod 62 back to or nearly back to its initial or proximal most position and thereby fully open the jaws. Such strokes in one embodiment incrementally open the jaws and thus allow disengagement of the stapler from the stapled tissue. In one embodiment, only a single stroke is utilized to completely open the jaws. In various embodiments, actuation (e.g., closing/opening of the jaws and/or firing of the staples) or articulation of the stapler is assisted by one or more motors.

The forward proximal and distal pawls 28, 25 slide distally and proximally on an outer surface of the actuation rod 62 as the trigger is squeezed and released and as the rack moves proximally and distally. As such, multiple strokes or squeezing and releasing of the trigger may be performed to fully move the actuation rod 62 back to or nearly back to its initial or proximal most position and to place or position the forward proximal and distal pawls 28, 25 back to or nearly back to their initial position relative to the actuation rod 62 (e.g., the forward proximal pawl 28 engaging cut-out 72 and the forward distal pawl 25 engaging cut-out 71). The actuator at its end of its reverse travel is shown for example in FIGS. 39-44. In one embodiment, the final squeeze of the trigger while in the reverse configuration locks out the STR and resets the actuator 2 to an initial or open-close mode as shown for example in FIGS. 42-44.

In accordance with various embodiments, the jaws 11, 12 when closed and the elongate shaft defines an outer diameter that is at least as equal to or smaller than the inner diameter of the trocar cannula. A typical surgical procedure may include a single site surgical access device or multiple trocar cannulas placed on and through the patient's body. In one particular embodiment, the inner diameter of the trocar cannula corresponds to 12 mm and the make-up or components of the jaws includes upper and lower jaws, pushers, staples, cartridge, and a jaw gap height. The cartridge is a nest for the pushers and staples and in one embodiment the cartridge is fixed inside the lower jaw. Pushers reside below the staplers and push the staples fully out of cartridge pockets within the cartridge when the pushers are acted upon by a slider. When the staples are pushed out of the cartridge, the staples must pass through the tissue and deform by contact into their corresponding anvil pockets within the anvil on the upper jaw. The actuation beam is a high stress component as it performs the work of closing the hinged upper jaw while compressing tissue therebetween, deploying the pushers to fire the staples and cutting the tissue at the center of the jaws.

In accordance with various embodiments, e.g., a 3.5 mm stapler STR, the staples have a height of approximately 0.140 inches and the pusher is about ⅔ of the staple height to fully deploy the stapes out of the cartridge. For such a staple, the jaw gap height between the upper and lower jaws is about 0.036 inches. FIGS. 53A-B illustrate a 3.5 mm staple 6 formed and unformed condition in accordance with various embodiments. In the unformed condition, the staple 6 has a height of about 3.5 mm and a width of about 3.0 mm and in a formed condition, the staple has a height of about 1.5 mm. The formed height may vary based on tissue thickness and other conditions effecting staple formation. FIGS. 56A-C illustrate an exemplary staple 6 unformed, formed at minimum height and formed at maximum height.

In the illustrated embodiment, the lower jaw has a thickness of 0.030 inches in order to remain rigid when the jaws are clamped on tissue. The lower jaw has an increased strength in the vertical direction as the side wall bends and wraps around and up the side of the cartridge. The upper jaw is generally a flat piece of metal that can be susceptible to bending when clamped on tissue and thus is thick.

Overall, the dimensions of all the components inside the cross section of the distal portion of the STR can be altered slightly, but usually only slightly. It is thus a significant challenge to add additional functionality to the distal portion of the STR while working under these space restrictions and maintaining functionality/reliability.

FIG. 54 depicts the limited space requirements or confines in which a laparoscopic surgical stapler must conform to these dimensions. Otherwise, increase incision size causes increased recovery time and unwanted patient trauma. In particular embodiments, the outer diameter 541 of the stapler is about 0.5 mm. As such, the upper jaw 11 including the anvil 9 and an upper guide 183 of the beam 18 occupies about a third of that space. A gap between the jaws 11, 12 is maintained to allow for tissue to be grasped and staples 6 to be fired and formed along with staple pushers 7 partially ejected from the cartridge 5 to fire the staples. This gap can be about 0.036" in accordance with various embodiments. The lower guide 184 of the beam 18 and the lower jaw 12 that includes the cartridge 5 occupy the remaining space. The height or space occupied by the cartridge 5 is further limited by the height of the staples 6 and the pushers 7 used to eject the staples. The dimensions of the lower jaw 12 and lower guide 184 of the beam 18 are also restrained due to space constraints and the desired strength and durability to ensure proper staple firing. Likewise, the dimensions of the upper jaw 11 and the upper guide 183 of the beam 18 are also limited due to space constraints and the required strength and durability to ensure depth and shapes of the anvil pockets 99 in the anvil 9 and proper staple formation.

FIGS. 55A-B illustrate the jaws of the stapler in accordance with various embodiments providing a maximum jaw gap height 554 (e.g., 0.038") and minimum jaw gap height 553 (e.g., 0.018"). In the maximum jaw gap height or initial condition, the cartridge is at its lowest height with the protrusions 551, 552 of the cartridge 5 at its lowest position firmly seated in the slots 1211, 1212 in the lower jaw 12. In the minimum jaw gap height or unconstrained condition, the cartridge 5 is at its highest height with the protrusions of the cartridge at their highest position in the slots 1211, 1212 in the lower jaw 12. In accordance with various embodiments, the interaction of the protrusions, e.g., protrusions 551, and the slots, e.g., slots 1211, further limits or regulates the range between the maximum and minimal jaw gap heights.

Generally, the laparoscopic linear cutting surgical stapler comprises a series of opposing ramps at low angles to uniformly lift the staple cartridge and lock it in place. One set of ramps remains stationary while the second set is moved longitudinally relative to the stationary set of ramps driving the surfaces of the ramps to slide against each other. The series of ramps are located along the length of the cartridge and the interaction of ramps causes the cartridge to lift uniformly. The cartridge contains staples, pushers and a slider.

In an initial or default position, e.g., as shipped, the cartridge is at its lowest positional height and thus the largest gap distance between the jaws. In this initial configuration, the jaws of the stapler can freely open and close to grasp tissue therebetween while being gentle on the tissue. The jaws can also thus be gently positioned on the tissue and the tissue positioned into the desired firing position or location. Once the user has found the desired firing location, the cartridge lift is engaged or activated. In one embodiment, the cartridge lift is engaged automatically during the initial firing stroke to fire or eject the staples from the cartridge. By engaging the cartridge lift, the lift is moved longitudinally and an interaction of ramps on the lift and a rampway or retainer and the biased lift apply a vertical lifting force on the cartridge moving the cartridge vertically towards the anvil and delivering a pre-determined pressure on the tissue between the jaws.

The clamping force between the jaws, cartridge, and ramps is directed in a direction perpendicular to the longitudinal axis of the stapler. The force also presses the two sets of ramps together. Due to the low angle of the ramp surfaces with respect to each other and also largely slanting perpendicular to the force, the clamping force or reaction force or pressure is unable to drive the ramps and thus the lift back longitudinally back into its initial position. In accordance with various embodiments, even with the addition of high forces encountered during the staple firing/forming which is also in the same perpendicular direction or even unexpected high pressure forces, the ramps and other components will deform rather than move longitudinally back. The cartridge lift is thus able to lift the cartridge to an infinite number of intermediate heights between the lowest and highest points rather than set incremental points while simultaneously locking or preventing the cartridge from returning back down. This can also be done automatically, e.g., with no user interaction to set or determine a particular height and to adjust or set the stapler to that determined height.

Figure 69A:
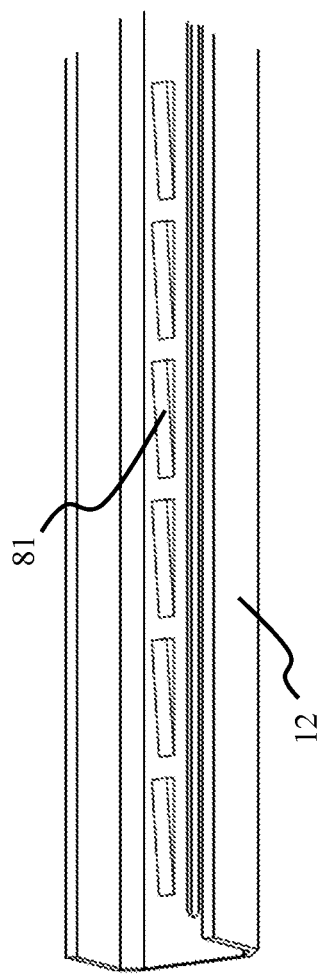
FIG. 69A is a bottom perspective view of portions of a staple and transector receptacle of a surgical stapler in accordance with various embodiments of the present invention.
Figure 69B:
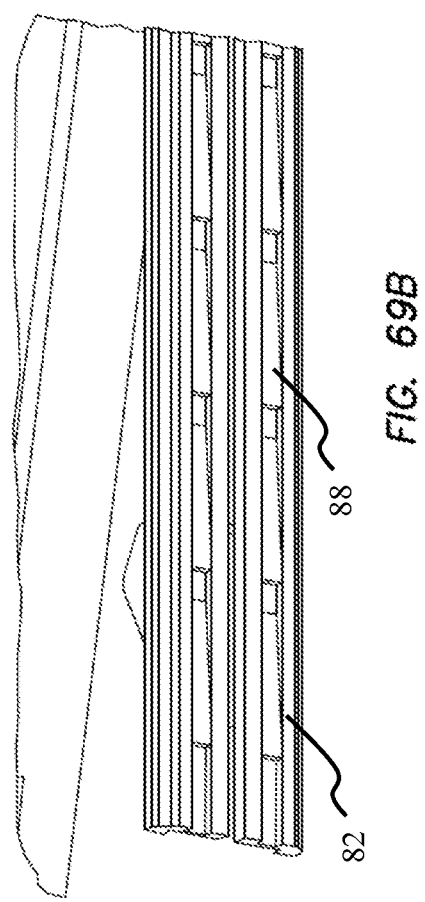
FIG. 69B is a bottom perspective view of portions of a staple and transector receptacle of a surgical stapler in accordance with various embodiments of the present invention.

In accordance with various embodiments, the ramps on the cartridge lift and the rampway have the same dimension and shape. In various embodiments, the ramps have different dimensions or shapes and the slope of the ramps defines or accounts for the compressive forces applied to tissue grasped between the jaws 11, 12. In accordance with various embodiments, the rampway 80 is built into or incorporated into the retainer or lower jaw 12 as shown for example in FIGS. 69-70. Also, as illustrated, the ramps 81 are slants of increasing slope extending proximally and the ramps 83 on the cartridge lift 82 are arranged as decreasing ramps slanting or extending proximally to mate and interact with each other to move the cartridge vertically as the cartridge lift is moved proximally.

The movable set of ramps is connected to a pre-loaded spring designed to apply the desired longitudinal force once released or engaged. The spring is also provided to apply a load on the ramps thereby moving the cartridge vertically to achieve a desired predetermined and optimal pressure on the tissue to produce the desired staple formation with minimal excessive pressure or trauma to the tissue and surrounding tissue.

By placing the biasing member or spring within the shaft or distally away from the jaws, allows for a larger biasing member (e.g., a spring without space constraints imposed by a jaw or jaws of the stapler), provides easier manufacturing, removes space constraints at the jaws and allows for a single force to be spread out and uniformly applied at the jaws. Such biasing members in the jaws are often impractical or inoperable as not effectively applying uniform forces against the cartridge to compress the tissue against the anvil. Appropriate compression of tissue and jaw gap height ensures proper staple formation. Proper staple formation ensures no leaking and reduced trauma to the tissue.

In accordance with various embodiments, the surgical stapler applies compression forces at three different intervals. The first compression can occur when the jaws are closed onto the tissue. The second compression occurs when the vertical adjustment driver is activated and the third compression occurs when the firing mechanism applies pressure on both jaws. By spreading out or sequencing the compression intervals, the tissue is allowed to compress further and resist less to the compression and thereby provide optimal staple formation and reduced tissue trauma.

The movable wedges can be biased by a cable or motors driven by pressure sensors. The stapler is a single use disposable device and as such the lift mechanism once initiated cannot be reset and thus the lift mechanism cannot be reused along with the associated cartridge. In accordance with various embodiments, the lift mechanism can be provided using ramps or wedges on the bottom of the cartridge, along the sides of the cartridge; ramps as separate inserts assembled or integrated in lower jaw or cartridge; and/or angled slots or channels instead of or in addition to wedges. In accordance with various embodiments, the cartridge lift could be biased distally instead of proximally to lift the cartridge and thus the direction or slope of the ramps would also be reversed. In accordance with various embodiments, a separate lockout or lift restraint is provided such as teeth or a ratchet like mechanisms on the cartridge lift, cartridge, lift barrel, lift beam or the like that provides only a one-way proximal or distal longitudinal and incremental movement of the cartridge lift or staple cartridge.

In various embodiments, a retainer includes a plurality of ramps that interact with a cartridge lift that is movable longitudinally and proximally and lifts the cartridge vertically. The cartridge lift in various embodiments has no ramps with smooth flat upper and lower surfaces but is attached to a ramp or protrusion like configuration and interaction as described throughout the description. In various embodiments, for example, as shown in FIGS. 60-65, the cartridge lift 8211 includes a plurality of ramps 8212 such that moving the cartridge lift distally (arrow D), e.g., away from the actuator, lifts the cartridge 5 vertically. The ramps on the cartridge lift decrease or slant down proximally and the ramps on the retainer slant up distally. As illustrated, the retainer is integrated or replaced by the lower jaw 12 in which the lower jaw 12 includes the corresponding ramps 1221. The staple cartridge 5 sits upon the cartridge lift and when the cartridge lift is moved distally, the ramps of the cartridge lift slide on the ramps of the lower jaw which moves the cartridge vertically. Additionally, as shown for example in FIGS. 62A-B, articulation is provided such that the jaws can pivot or be angled away from or out of alignment with the longitudinal axis without opening or closing of the jaws. The cartridge lift in various embodiments is biased in the distal direction. In accordance with various embodiments, spring 871 biases the cartridge lift distally. A proximal end of the cartridge lift extends vertically or includes an extended base 8213. The extended base is positioned between the 871 and an actuation beam 18. The spring applies a force in the distal direction against the extended base. However, the position of the actuation beam restrains or restricts distal movement of the extended base of the cartridge lift and thus the release of the spring 871.

In a fire activation configuration, the actuation beam is moved distally and thus allows the movement of the extended base and the release of the spring to apply a spring force against the cartridge lift. As such, the spring moves the cartridge lift distally causing the cartridge to lift up or move only vertically and self-adjust to the tissue in the jaws.

In various embodiments, as shown for example in FIGS. 68A-B, the cartridge lift 824 includes apertures 825 through which a plurality of ramps 503 on a cartridge platform 501 extends therethrough. Movement of the cartridge lift proximally lifts the cartridge platform or frame vertically. In particular, movement of the cartridge lift proximally causes the distal most ends or walls of the apertures to interact with the ramps on the cartridge platform that slant down proximally. As a result, the cartridge platform is moved vertically as the cartridge lift is moved longitudinally, e.g., proximally. In various embodiments, the cartridge is seated on the cartridge platform and as such the cartridge and cartridge platform only moves vertically or in a direction traverse to the longitudinal movement of the cartridge lift. In various embodiments, the cartridge and cartridge platform are integrated to form a monolithic structure.

Figure 71:
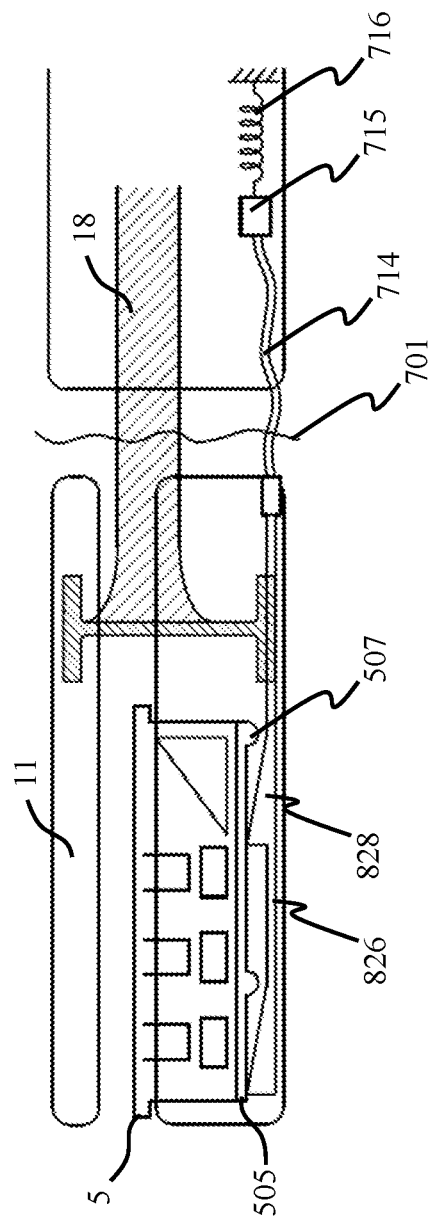
FIG. 71 is a side cross-sectional view of a staple and transector receptacle of a surgical stapler in accordance with various embodiments of the present invention.

In various embodiments, as shown for example in FIG. 71, a cartridge platform 505 includes a plurality of protrusion 507 (e.g., bumps) and a cartridge lift 826 includes a plurality of ramps 828 such that moving the cartridge lift 826 proximally causes the ramps of the cartridge lift to interact with the bumps of the cartridge platform to lift the cartridge 5 vertically.

In various embodiments, the cartridge lift is connected to a flexible pull cable, e.g., cable 714. The flexible pull cable includes a hold/release block 715 coupled to a tension spring 716. The flexibility of the pull cable assists in flexing or articulating of the jaws relative to the elongate shaft (e.g., at a flex point or joint denoted abstractly by curved line 701). The tension spring biases the cartridge lift proximally. The hold/release block limits or restricts movement of the pull cable and likewise the cartridge lift. Once activated, the hold/release block is released allowing the pull cable and the cartridge lift to be pulled proximally. As the cartridge lift is moved proximally, the cartridge moves vertically towards the upper jaw 11. In various embodiments, the cartridge is seated on the cartridge platform and as such the cartridge and cartridge platform only moves vertically or in a direction traverse to the longitudinal movement of the cartridge lift. In various embodiments, the cartridge and cartridge platform are integrated to form a monolithic structure.

Figure 66A:
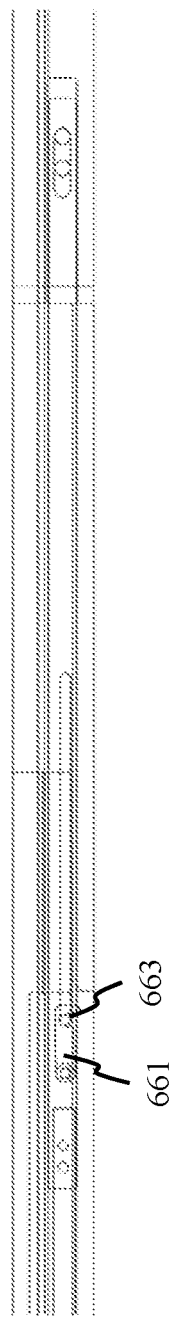
FIG. 66A is a side view of a portion of a staple and transector receptacle of a surgical stapler in accordance with various embodiments of the present invention.
Figure 66B:
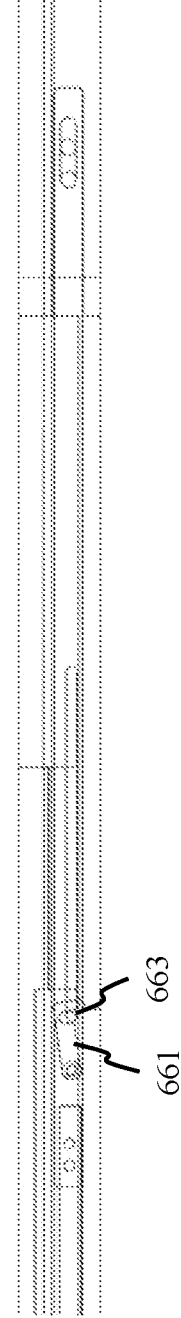
FIG. 66B is a side view of a portion of a staple and transector receptacle of a surgical stapler in accordance with various embodiments of the present invention.
Figure 67A:
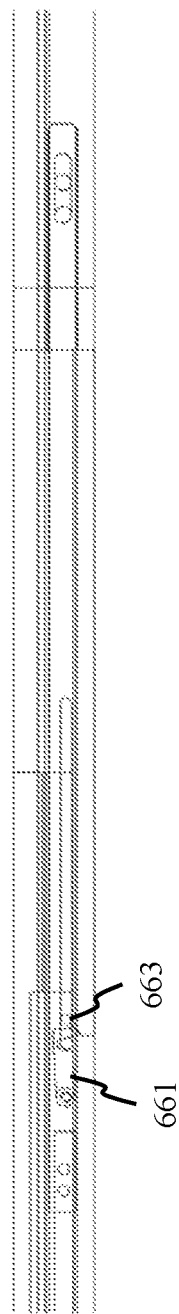
FIG. 67A is a side view of a portion of a staple and transector receptacle of a surgical stapler in accordance with various embodiments of the present invention.
Figure 67B:
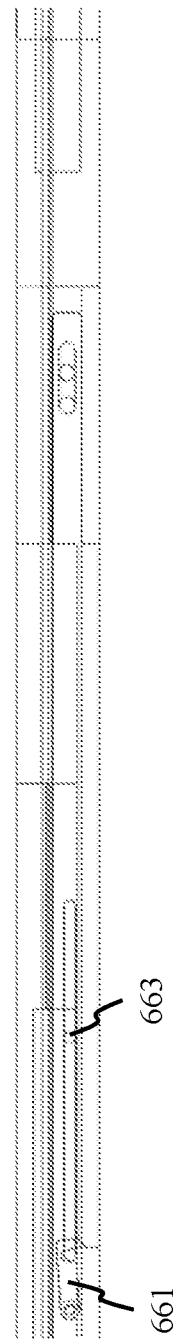
FIG. 67B is a side view of a portion of a staple and transector receptacle of a surgical stapler in accordance with various embodiments of the present invention.

In various embodiments, as shown for example in FIGS. 66-67, an actuation lock or link 661 is pivotably connected to the actuation rod or slides in which in one position the actuation link restricts the actuation rod or slides and prevents the firing of staples and cutting of tissue between the jaws. The actuation rod or slides operate as previously described in various embodiments. Initially, the actuation link 661 hooks onto an actuation pin 663 that is connected to an actuation rod. The actuation slide is connected to a trigger such that when the trigger is manipulated the actuation slide also moves but in an opposite direction. Thus, when the trigger is squeezed proximally, the actuation slide moves distally to ultimately close the jaws and eject the staples as shown for example in FIGS. 66A-66B. Moving the actuation slide back proximally opens the jaws. As shown in FIG. 66B, as the actuation slide is moved back, the actuation link is pivoted or rotated up to disconnect or unhook the link from the actuation pin 663. This disconnection disables the connection between the actuation slide and the distal working portions of the stapler, e.g., the firing of the staples or the movement of the jaws. As shown, in FIGS. 67A-B, the actuation pin 663 is free to move proximally and distally but is no longer connected to the actuation link. Any movement of the actuation pin thus does not move the distal working portions of the stapler and thus movement of the trigger also does not move the distal working portions of the stapler. In various embodiments, only the ability to fire staples is disconnected by the interaction of the actuation link and the actuation pin but the opening and closing of the jaws are still permitted. As such, the trigger can be moved to open and close the jaws while any movement or components to fire the staples are disengaged.

Figure 59A:
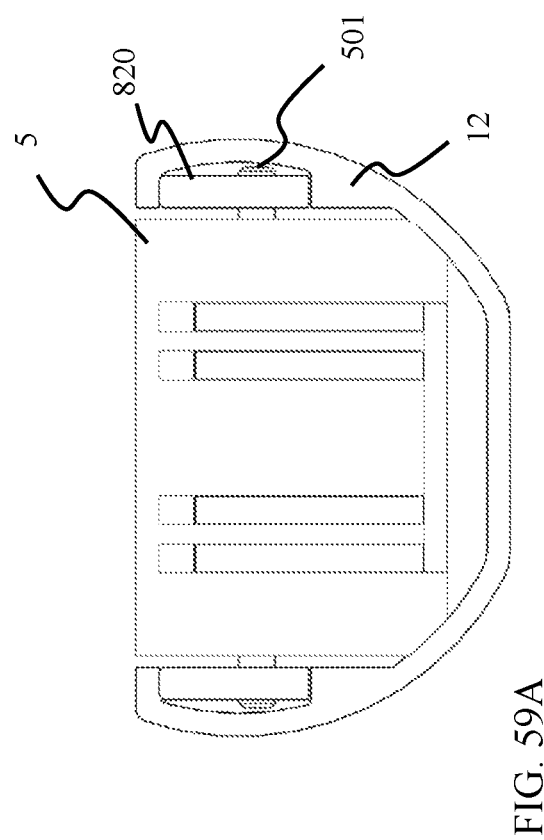
FIG. 59A is front cross-sectional view of portions of a staple and transector receptacle of a surgical stapler in accordance with various embodiments of the present invention.
Figure 59B:
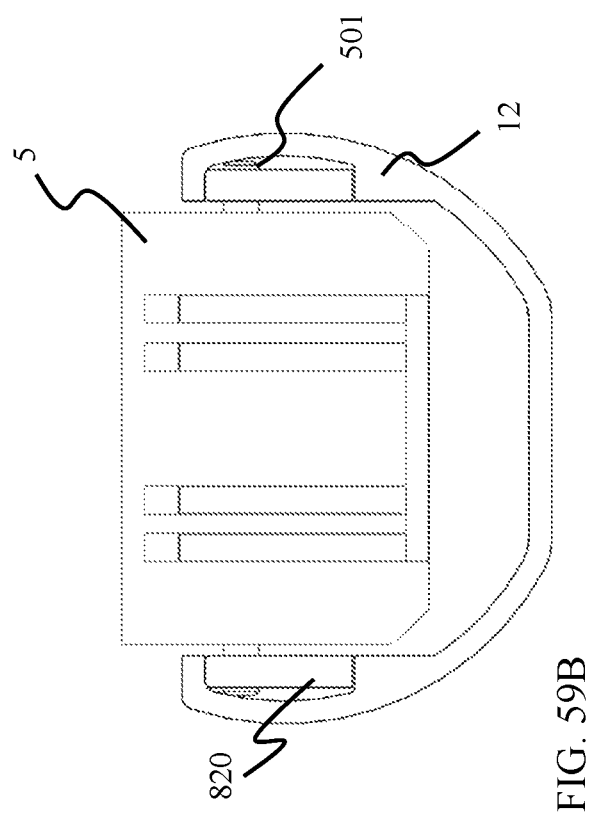
FIG. 59B is front cross-sectional view of portions of a staple and transector receptacle of a surgical stapler in accordance with various embodiments of the present invention.
Figure 60:
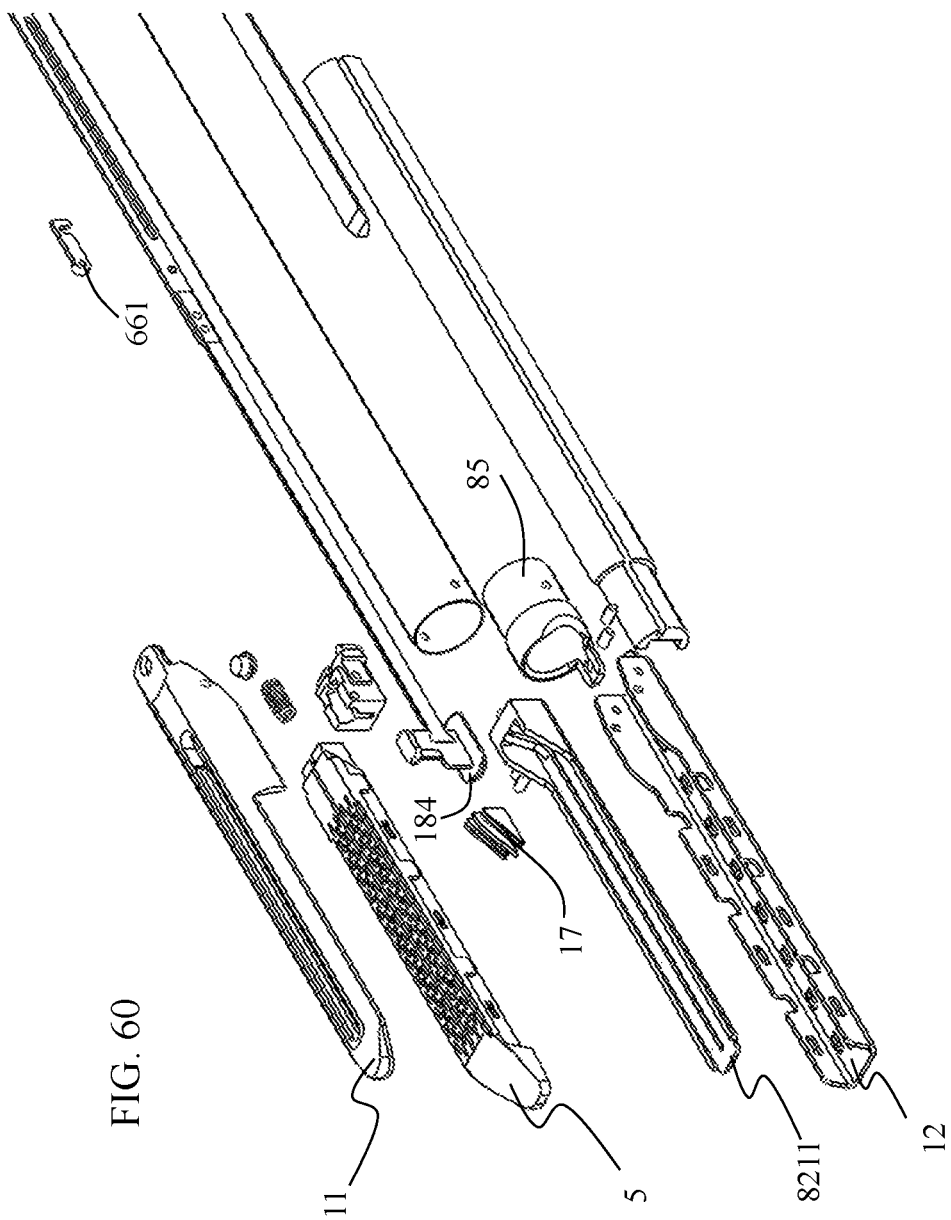
FIG. 60 is an exploded view of portions of a staple and transector receptacle of a surgical stapler in accordance with various embodiments of the present invention.
Figures 62A, 62B:
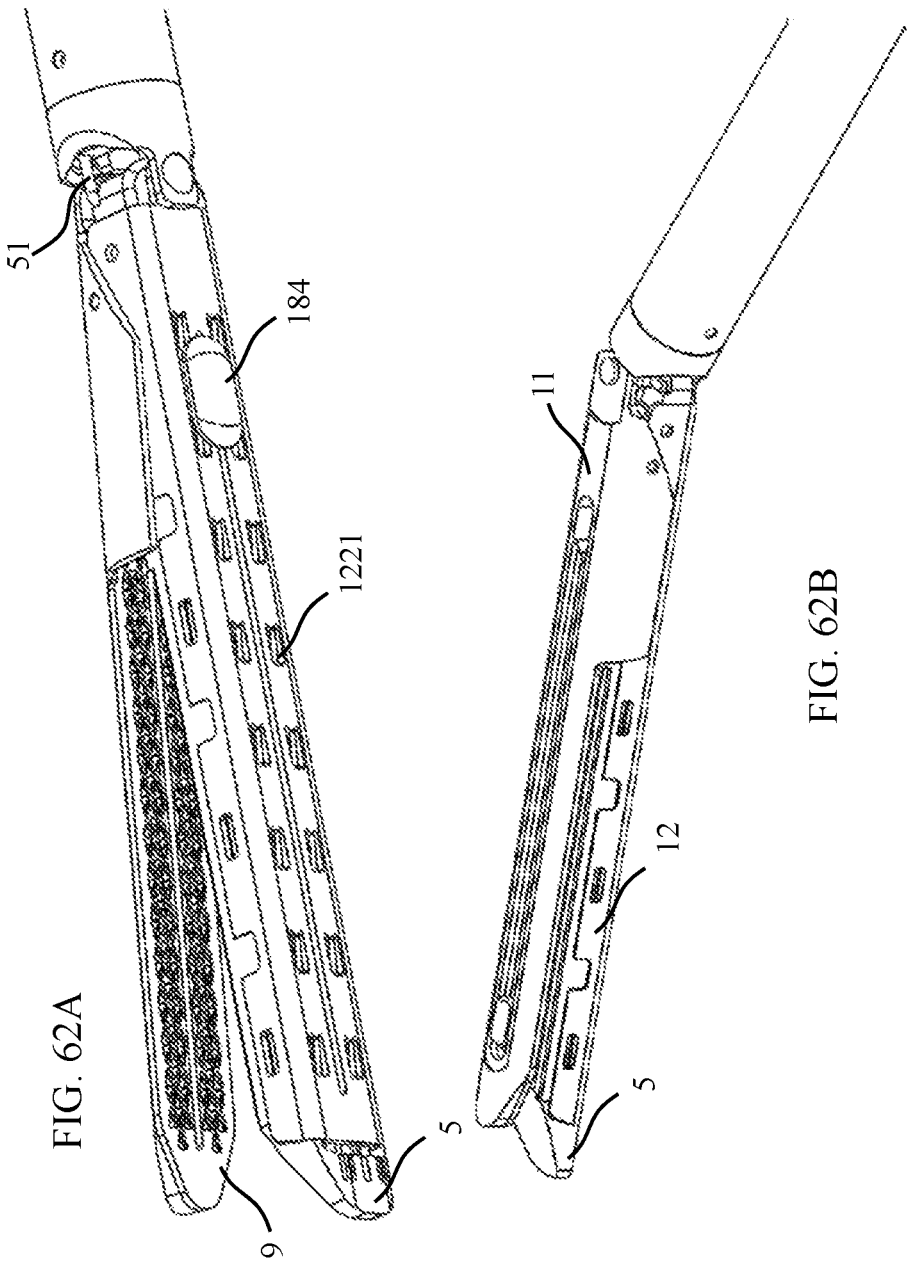
FIG. 62A is a bottom perspective view of a staple and transector receptacle of a surgical stapler in accordance with various embodiments of the present invention.
FIG. 62B is a perspective view of a staple and transector receptacle of a surgical stapler in accordance with various embodiments of the present invention.

In various embodiments, as shown for example in FIGS. 57-59, ramps or slots 821 are added along the sides of cartridge lifts 820 and corresponding protrusions or detents 501 extend from a cartridge retainer or a cartridge 5 instead of along the respective bottom and upper surfaces of the lift and jaw. The cartridge lifts 820 in accordance with various embodiments are similarly biased, e.g., in a proximal direction (arrow H), and once activated raises the cartridge vertically (arrow V) through the interaction of the protrusions of the cartridge and the slots of the lifts 820. In various embodiments, the protrusions are on the lifts and the slots are on the cartridge or in various embodiments, various combinations of protrusions and slots are provided with some on the cartridge and some on the cartridge lifts, e.g., a cartridge has proximal protrusions and distal slots and the cartridge lifts have corresponding proximal slots and distal protrusion. Protrusions may be desired extending from the cartridge to maximize the space within the cartridge for the staples and the ejection of staples. Portions of the lower jaw 12 and the cartridge 5 are removed from the illustrated embodiment to ease description of embodiment. Additionally, although shown separately the cartridge lifts in various embodiments are connected proximally in the shaft or actuator to form a single monolithic structure to further ensure uniform movement of the lifts.

In accordance with various embodiments, an actuation beam provides functional parallel jaws during closure, compression and high forces of staple firing/forming. As such, the actuation beam closes the jaws and maintains consistent parallel closure along the length of the jaw and in various embodiments the actuation beam is arranged to withstand significant firing/closure forces at a pre-determined height (height at which the actuation beam was manufactured). The actuation beam structural member is thus made from high grade stainless steels for example and thus strong and rigid. Making or providing an adjustable actuation beam can sacrifice or reduce inherent strength and rigidity of actuation beam.

In various embodiments, an adjustable actuation beam can provide an adjustable jaw gap and/or a low or reduced overall outer or body diameter. In various embodiments, such an adjustable actuation beam can cause width constraints, complex construction, e.g., actuation beam or jaw mechanisms, and/or reduce actuation beam strength.

In various embodiments, the actuation beam closes the top jaw to the bottom jaw when it is advanced. The actuation beam closes the jaws together at a fixed height or jaw gap. If the actuation beam was able to be adjusted in height, the user could then adjust the jaw gap appropriately for the desired tissue to use it on. In accordance with various embodiments, adjustable actuation beams 1800 are illustrated for example in FIGS. 72-74 and in which the actuation beams are split or forked at the distal end providing an upper arm 188 and a lower arm 189 with a space between the two and/or a middle portion removed. For example, in FIGS. 72A-B, the actuation beam 1800 includes an adjustable or stretchable material or web 1802 between upper and lower guides of the actuation beam and, in one embodiment, the material biases the guides together or stretchable or inherently biased to squeeze the guides together and thereby seek to reduce the staple height or jaw gap and/or to apply compressive forces on tissue between the jaws. In accordance with various embodiments, in FIG. 73, a ratchet 1803, e.g., teeth or racks, extend from either or both upper and lower arms of the actuation beam 185. In various embodiments, a perpendicular extension tab extends from the upper arm of the actuation beam and includes a plurality of projections and a perpendicular extension tab extends from the lower arm of the actuation beam and includes a plurality of projections arranged to interact with the plurality of projections of the perpendicular extension tab of the upper arm of the actuation beam. Such a ratchet or interaction of projections holds or biases the arms together and can be utilized to incrementally adjust the overall height of the beam or the spacing between the arms. In FIG. 74, in accordance with various embodiments, the cover tube or another actuation tube or cover 1805 is provided to force or bias the upper and lower arms of the actuation beam to together as the beam is squeezed into the tube or the tube is squeezed over the arms of the beam. These upper and lower guides may also include a material or ratchet between them to further assist in a uniform and consistent closure or pressure in bringing the guides together. Additionally, such forces or biasing material or mechanism in accordance with various embodiments may be one-way, e.g., moving to close the guides together and thus unable to open or release, and/or in one direction, e.g., towards each other or just towards the upper or lower guide, to maintain a parallel relationship of the guides with each other and the longitudinal axis. A separate release or disengagement component would be used to move the arms apart sufficiently to release the stapled tissue.

However such an adjustable actuation beam may still need to provide sufficient strength in order to close the jaw especially if the tissue between the jaws is thick. The adjustable actuation beam may also be very thin to leave room for multiple rows of staples in the cartridge. The jaws may also need to stay parallel to the cartridge during firing. As such, a mechanism may be needed to allow one or both of the jaws to realign the gap to match the adjustable actuation beam. The actuation beam may also need to be acted on by a separate biasing component or mechanism to adjust the height. The additional biasing component or mechanism may also have to articulate. The pivot joint between the top and bottom jaws may also have to adjust accordingly to match the actuation beam to maintain parallel jaws.

The ramp configuration as previously described in accordance with various embodiments as compared to the adjustable actuation beam embodiments may have fewer parts. The ramp configuration for example has a single location jaw pivot pin with a thin and simple or straight-forward actuation beam.

In various embodiments, for example, as shown in FIGS. 77-79, the stapler provides an adjustable top jaw or adjustable anvil surface that provides parallel jaws at various staple heights. However, given the limited space, the top jaw is usually not thick enough or does not have room enough for lift mechanisms especially relative to the size of bottom jaw and associated staples.

As shown in FIGS. 75A-75B, a gap 751 is present at the distal most portion of typical jaws 111, 112 and in various embodiments this gap is closed or reduced to a near zero configuration allowing the typical lost space to be better utilized to capture and compress tissue. As illustrated in FIGS. 75C-75D, the angled bottom jaw 754 reclaims some of the lost space. The gap 751 at the distal most portion of the jaws is reduced nearly to zero while the tissue gap at the proximal portion of the jaw remains unchanged. During firing of the staples, the top jaw 111 is opened or moved away from the bottom jaw 112 to position the top jaw in a parallel position relative to the bottom jaw to ensure a more uniform compression of tissue and staple formation.

Figure 77A:
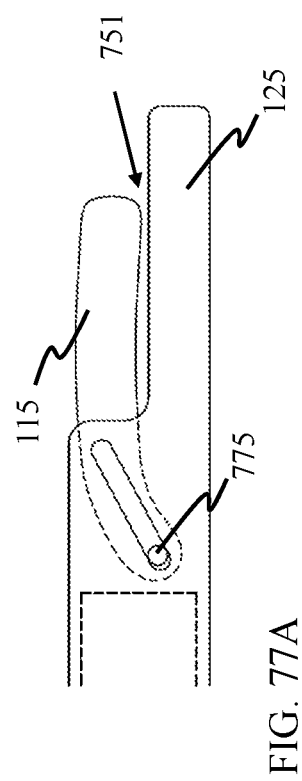
Figure 77B:
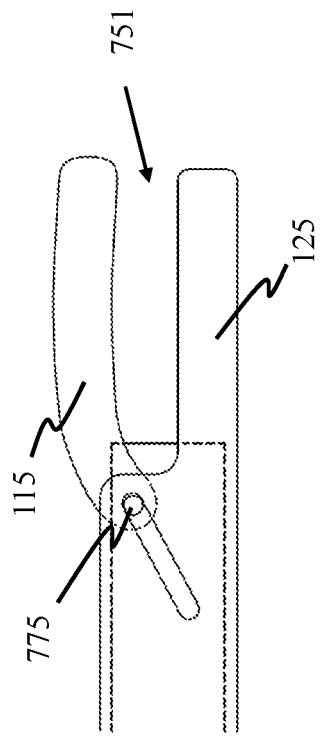

In FIGS. 77A-77B, the sliding top jaw 115 when closed is offset or positioned more proximally than the fixed bottom jaw 125. In such a position, a small gap or no gap 751 is disposed between the jaws and thereby defining or delimiting a small outer diameter to facilitate entering or exiting small diameter surgical access ports, such as 5 mm cannulas. The sliding top jaw when fully opened defines a large gap 751 between the jaws to increase the ability of the jaws to capture large portions of tissue between the jaws. However, the sliding pivot 775 of the sliding top jaw ensures that the jaws remain parallel relative to each other to ensure a more uniform compression of tissue and staple formation. In accordance with various embodiments, movement of the actuation beam distally moves the jaws from an open position and a closed position or a separate rod, cable or tube is utilized to move the jaws from an open and closed position and vice versa.

As illustrated in FIGS. 78A-79C, a toggle top jaw 116, 117 when closed provides a specific gap between the jaws. The specific gap can be small enough to facilitate placement through and withdrawal of the instrument from small diameter surgical access ports. The toggle top jaw when fully opened defines a large gap between the jaws to increase the ability of the jaws to capture large portions of tissue between the jaws. However, the toggle top jaw ensures that the jaws remain parallel relative to each other to ensure a more uniform compression of tissue and staple formation. In accordance with various embodiments, movement of the actuation beam 18 distally can move the jaws from an open position and a closed position. A proximal portion of the beam interacts with the toggle top jaw to prevent further rotation or pivoting of the jaw to further ensure that the jaws remain parallel relative to each other to ensure uniform compression of tissue and staple formation. In various embodiments, a slot 1174 of the toggle top jaw interacts with the actuation beam to rotate or pivot of the jaw. In various embodiments, feet or a proximal end 1173 of the toggle top jaw interacts with the shaft of the stapler to prevent further rotation or pivoting of the jaw. In accordance with various embodiments, the toggle top jaw comprises a top jaw toggle 1161, 1171 and a toggle link 1162, 1172 pivotably connected to the shaft and/or bottom jaw or bottom jaw support. The toggle link is also pivotably connected to top jaw toggle. The top jaw toggle remains parallel to the bottom jaw 125 and includes an anvil. The top jaw toggle in various embodiments is made of a material or comprising of materials stronger or firmer than the toggle link to withstand staple formation forces and facilitate staple formation.

The adjustable top jaw with an actuation beam 18 is similar to previously described embodiments. The actuation beam height remains the same height during use however the difference in staple heights is accommodated by a small shoe or spacer that resides in the top jaw or the lower jaw assembly. For example, if a small jaw gap is desired, a spacer would be added while if a large jaw gap is desired, the spacer would not be used. The decision to add a spacer may be left with the user. The engagement of the spacer as desired may be activated by the actuation beam or similar mechanisms used in the firing or pre-firing process. Such mechanism may also have to articulate. The top or bottom jaw may need to be thinner to provide space for the spacer which can reduce the jaws strength. The spacer's strength may also be enhanced to accommodate the reduced jaw strength and to withstand compressive forces in the staple formation process. A space may also be provided to accommodate storage of the spacer when not in use.

Relative to the various other embodiments previously described, the top jaw would likely be thicker in cross section. A strong top jaw that minimizes flexing is often desired for proper staple formation. As such, a single monolithic top jaw is often desired. The spacer provides a finite number of gap height changes and is not automatically-adjustable.

In accordance with various embodiments, an adjustable top jaw can provide an adjustable and comparable jaw gap and an overall low body diameter. However, the adjustable top jaw could also increase space between staple lines, increase complexity to the actuation beam or other components and/or reduce the top jaw strength.

In accordance with various embodiments, the cartridge is adjusted using springs or other similar biasing mechanisms. Such embodiments however can be difficult to lock the cartridge in place once an optimum spacing has been reached. For example, springs under the cartridge allows the cartridge to move or adjust due to the thickness of tissue. However, the cartridge would move again due to higher forces encountered during staple firing and forming. As such, the cartridge moves freely in response to the tissue thickness but may not be able to lock solidly in place once the optimum height has been found and all within the limited space of a linear laparoscopic cutting cartridge.

Figure 76:
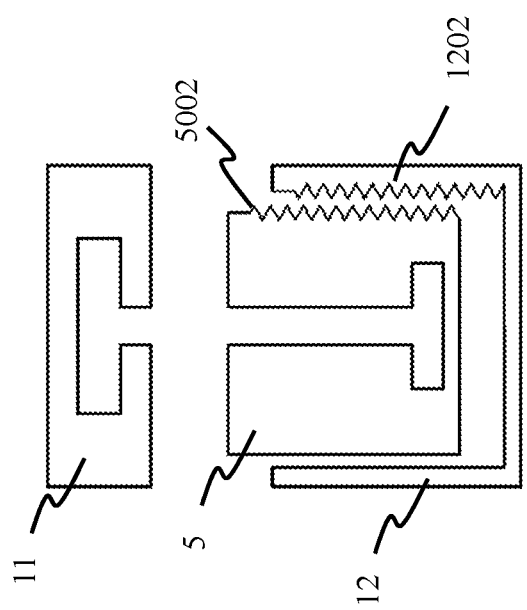

Referring to FIG. 76, in accordance with various embodiments, the cartridge 5 is floating or not directly coupled to the jaw of the stapler. Contact of the cartridge with the tissue causes the cartridge to re-size to an optimum tissue gap. The cartridge includes teeth 5002 that interlock with corresponding teeth 1202 on the jaw to lock the cartridge in place at the optimum tissue gap. In one embodiment, the bottom jaw clamps on the cartridge to interlock the teeth of the cartridge and the bottom jaw. In another embodiment, movement of the actuation beam slides the cartridge to the side to interlock the teeth of the cartridge and the bottom jaw. The teeth could be on both sides of the cartridge with corresponding interlocking teeth disposed on both sides of the bottom jaw.

In accordance with various embodiments, an adjustable top/bottom jaw is provided without the use of an actuation beam. Other mechanisms to open and close the jaws could provide parallel jaws during closing and staple formation and counteract or account for compressive forces encountered during closing and staple formation. Such mechanism may thus be thicker and stronger that may reduce the ability to articulate or space availability to accommodate the space limitations in laparoscopic procedures.

The top jaw would have to be much thicker than a normal jaw due to the lack of an actuation beam. The cartridge would need to house the cutting blade and protect it after the device is fired and the jaw opened.

In accordance with various embodiments, one or more ramps are placed along the sides of a cartridge or cartridge lift interacting with ramps on the sides of a rampway, retainer or lower jaw. An actuation beam is provided to close the jaw, fire the staples, release jaw gap spring, and cut the tissue. The jaw gap is set by the side ramps and in one embodiment the cartridge is held in place by a frame that is acted on by the cartridge lift. When the cartridge lift is activated, the frame and cartridge close the gap based on a biasing member, e.g., a spring and its spring rate, that has be predefined or predetermined to be optimal for tissue compression. The jaw gap change is done automatically.

In such embodiments, compressive forces are transmitted to the sides of the cartridge or cartridge lift rather than being distributed on a bottom flat surface as provided in various other embodiments previously described. Such side distribution may reduce the ability to accommodate such forces for proper staple formation or may require thicker or stronger wedges or sides of such components to account for the encountered forces. In accordance with various embodiments, side ramps can provide an adjustable and comparable jaw gap and an overall low body diameter. However, the side ramps may encounter width constraints. In various embodiments, the stapler includes a separate user-accessible switch or button to initiate, unlock or activate the biasing of the cartridge lift or the lift lock. In various embodiments, the separate switch may only become accessible once firing of the staples has activated or unlocked. The biasing of the cartridge in various embodiments may be by performed by one or more springs, elastic bands, cables, magnets, hydraulics or other similar biasing systems. The cartridge lift, biasing systems or both in various embodiments may be assisted by motors and/or sensors. In various embodiments, the lift lock cannot be relocked or the biasing systems reset or placed back to its initial position.

Additionally, although this application discloses certain embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. As such, it should be appreciated that although specific combinations of embodiments and features or aspects of various embodiments may not be explicitly described such combinations however are contemplated and within the scope of the present inventions. Thus, it is intended that the scope of the present inventions herein disclosed should not be limited by the particular disclosed embodiments described above.

The invention claimed is:

1. A surgical stapler comprising:
   a first jaw comprising an anvil;
   a second jaw comprising a cartridge having a plurality of staples, the first jaw movable towards and away from the second jaw;
   an actuator having an upper guide longitudinally slidable within the first jaw and a lower guide longitudinally slidable within the second jaw and longitudinally advanceable to move the first jaw towards the second jaw and deploy the plurality of staples from the cartridge; and
   a cartridge lift disposed between the second jaw and the cartridge, the cartridge lift arranged to move the cartridge towards the first jaw while the cartridge lift moves in a longitudinal direction, wherein the cartridge lift is activated by longitudinal advancement of the actuator to a predetermined position.

2. The stapler of claim 1 wherein the cartridge lift is movable only in the proximal direction.

3. The stapler of claim 1 wherein the cartridge is movable only in a direction towards the first jaw.

4. The stapler of claim 1 further comprising a spring connected to the cartridge lift.

5. The stapler of claim 4 wherein the spring is restrained.

6. The stapler of claim 5 further comprising an elongate shaft connected to the first and second jaws, the first and second jaws being pivotably connected to each other and the actuator being removably connected to the elongate shaft, the actuator configured to release the spring to activate the cartridge lift.

7. The stapler of claim 1 wherein the cartridge lift comprises ramps having lower surfaces facing a retainer, the retainer comprising ramps having upper surfaces facing the cartridge lift, the upper surfaces of the ramps of the retainer being shaped and positioned complementary to the lower surfaces of the ramps of the cartridge lift.

8. The stapler of claim 7 further comprising a lift lock blocking movement of the cartridge lift.

9. The stapler of claim 7 wherein the retainer and anvil remains stationary when the cartridge moves towards the first jaw.

10. A surgical stapler comprising:
    a first jaw comprising an anvil;
    a second jaw comprising a cartridge comprising a plurality of staples, the first jaw movable towards and away from the second jaw;
    a cartridge lift disposed between the second jaw and the cartridge, the cartridge lift arranged to move the cartridge towards the first jaw while the cartridge lift moves in a longitudinal direction; and
    a cartridge lift spring biasing the cartridge lift proximally in the longitudinal direction.

11. The stapler of claim 10 wherein the cartridge lift spring is initially locked and the cartridge lift remains at a lowest vertical position.

12. The stapler of claim 11 wherein the cartridge lift spring is unlocked once a firing operation has commenced.

13. The stapler of claim 12, wherein the cartridge moves towards the first jaw prior to firing of the staples.

14. The stapler of claim 10 wherein the cartridge lift provides an active vertical force against the cartridge.

15. The stapler of claim 10 further comprising an elongate shaft connected to the first and second jaws, the first and second jaws being pivotably connected to each other, and an actuator removably connected to the elongate shaft and arranged to move the first and second jaws.

16. A surgical stapler comprising:
a first jaw comprising an anvil;
a second jaw having a proximal end and a distal end and comprising a cartridge comprising a plurality of staples, the first jaw movable towards and away from the second jaw; and
a cartridge lift disposed between the second jaw and the cartridge and wherein the cartridge lift is biased by a lift spring in a proximal longitudinal direction away from the distal end of the second jaw.

17. The stapler of claim 16 wherein the cartridge is movable in only a single direction.

18. The stapler of claim 16 wherein the cartridge is movable in a single direction, the single direction being traverse to the proximal longitudinal direction in which the cartridge lift moves.

19. The stapler of claim 16 wherein the anvil is stationary.

20. The stapler of claim 16, further comprising a lift lock preventing the lift spring from moving, the lift lock being unlocked and releasing the lift spring once a firing operation has commenced.

21. The stapler of claim 20, wherein the lift lock is unable to be relocked.

* * * * *